(12) United States Patent
Scharf et al.

(10) Patent No.: US 11,364,285 B2
(45) Date of Patent: Jun. 21, 2022

(54) METHODS, COMPOSITIONS, AND MOLECULAR TARGETS THAT EXPLOIT SYNERGIES AND SYMBIOSES IN THE TERMITE GUT

(71) Applicant: Purdue Research Foundation, West Lafayette, IN (US)

(72) Inventors: Michael E. Scharf, Battle Ground, IN (US); Brittany F. Peterson, Mascoutah, IL (US)

(73) Assignee: Purdue Research Foundation, West Lafayette, IN (US)

( * ) Notice: Subject to any disclaimer, the term of this patent is extended or adjusted under 35 U.S.C. 154(b) by 652 days.

Patent file contains an affidavit/declaration under 37 CFR 1.130(b).

(21) Appl. No.: 15/476,523

(22) Filed: Mar. 31, 2017

(65) Prior Publication Data

US 2018/0020678 A1 Jan. 25, 2018

Related U.S. Application Data

(60) Provisional application No. 62/316,781, filed on Apr. 1, 2016.

(51) Int. Cl.
| | | |
|---|---|---|
| A01N 65/00 | (2009.01) | |
| A01N 43/16 | (2006.01) | |
| A61K 38/47 | (2006.01) | |
| A01N 43/50 | (2006.01) | |
| A01N 57/16 | (2006.01) | |
| A01N 51/00 | (2006.01) | |

(52) U.S. Cl.
CPC .............. *A61K 38/47* (2013.01); *A01N 51/00* (2013.01); *C12Y 302/01* (2013.01)

(58) Field of Classification Search
None
See application file for complete search history.

(56) References Cited

U.S. PATENT DOCUMENTS

| | | | | |
|---|---|---|---|---|
| 7,968,525 B1 * | 6/2011 | Scharf | .................. | C12N 15/113 |
| | | | | 514/44 A |
| 8,445,240 B2 * | 5/2013 | Scharf | ..................... | C12N 9/16 |
| | | | | 435/105 |
| 2010/0011654 A1 * | 1/2010 | Kaletta | .................. | A01N 63/00 |
| | | | | 43/107 |
| 2013/0058890 A1 * | 3/2013 | Raemaekers | .......... | A01N 63/60 |
| | | | | 424/84 |
| 2014/0026468 A1 * | 1/2014 | Henderson | ........... | A01M 1/2011 |
| | | | | 43/131 |

FOREIGN PATENT DOCUMENTS

AU 2009267007 B2 * 2/2016 ........... C12N 15/111

OTHER PUBLICATIONS

Sen (Molecular Signatures of Nicotinoid-Pathogen Synergy in the Termite Gut, 2016). (Year: 2016).*
Peterson, Brittany. (Quantification of symbiotic contributions to lower termite lignocellulose digestion using antimicrobial treatments, 2015). (Year: 2015).*
Konig, Helmut and Varma, Ajit. Intestinal Microorganisms of Termites and Other Invertebrates. Springer. 2006. Page 90. (Year: 2006).*
Boucias, D.G. The Effects of Imidacloprid on the Termite Reticulitermes flavipes and its Interactions with the Mycopathogen Beauveria bassiana. Pflanzenschutz-Nachrichten Bayer 49/1996, 2. pp. 103-144. (Year: 1996).*
Sethi, Amit et. al. A GHF7 Cellulase from the Protist Symbiont Community of Reticulitermes flavipes Enables more Efficient Lignocellulose Processing by Host Enzymes. Wiley Online Library (wileyonlinelibrary.com). Archives of Insect Biochemistry and Physiology, vol. 84, No. 4, pp. 175-193 (Year: 2013).*

* cited by examiner

*Primary Examiner* — Nghi V Nguyen
(74) *Attorney, Agent, or Firm* — Reichel Stohry Dean LLP; Natalie J. Dean; Mark C. Reichel

(57) ABSTRACT

Methods and compositions for controlling termite populations by leveraging newly discovered mechanisms for symbiont- and host mediated anti-fungal defenses in the termite hind-gut. Such methods may include administering a composition to a termite, the composition formulated to promote protist dysbiosis in the gut of the termite, or silencing specific host or symbiont genes by RNA interference, and exposing the termite to a pathogen, where the composition increases the susceptibility of the termite to the pathogen. Compositions are also provided for the treatment of fungal infections, the composition comprising a medically effective amount of recombinant glycosyl hydrolase family 7 cellulase, as well as methods for utilizing the same.

16 Claims, 17 Drawing Sheets

Specification includes a Sequence Listing.

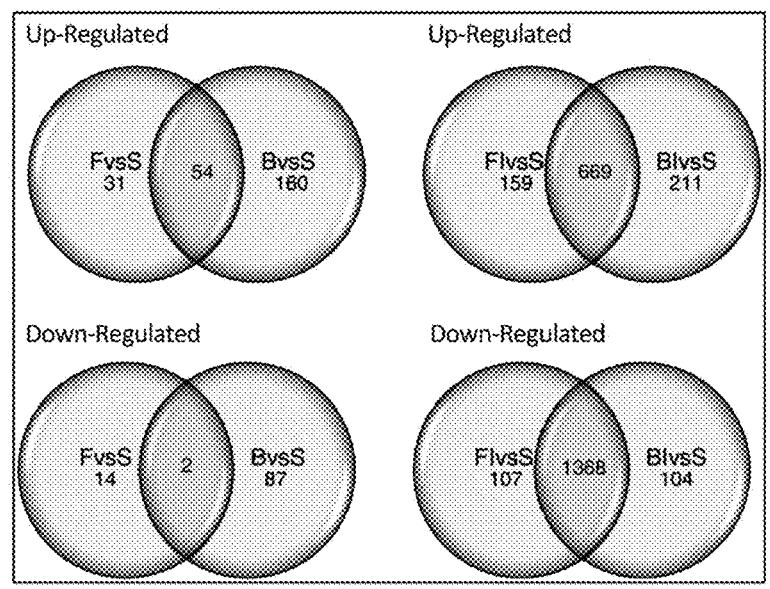
FIGURE 13A
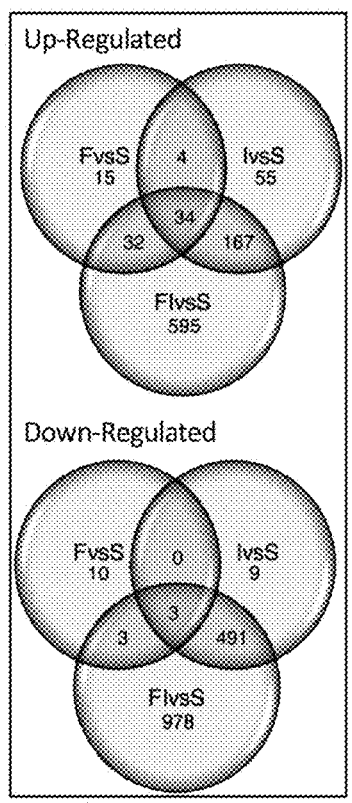 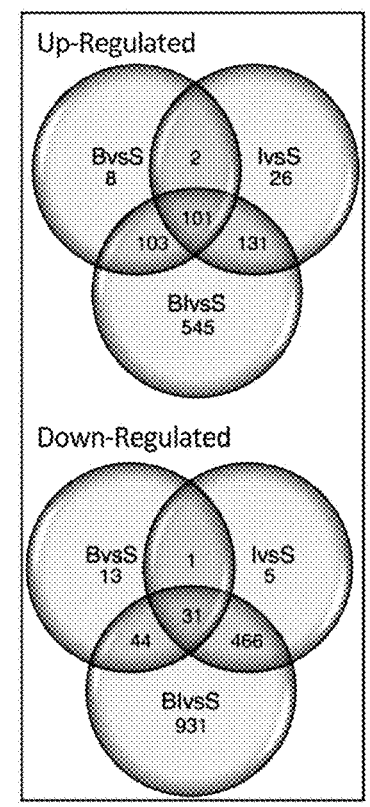
FIGURE 13B        FIGURE 13C

Amidohydrolase gene expression

FIGURE 19A

T-test
p = 0.024

Y-axis: Fold Change Relative to Respective Controls
X-axis: Control, 5% Kan

Susceptibility to *B. bassiana*

FIGURE 19B

T-test
p = 0.009

Y-axis: Normalized Mortality 7DPI (%)
X-axis: Treatments — Control, 5% Kan

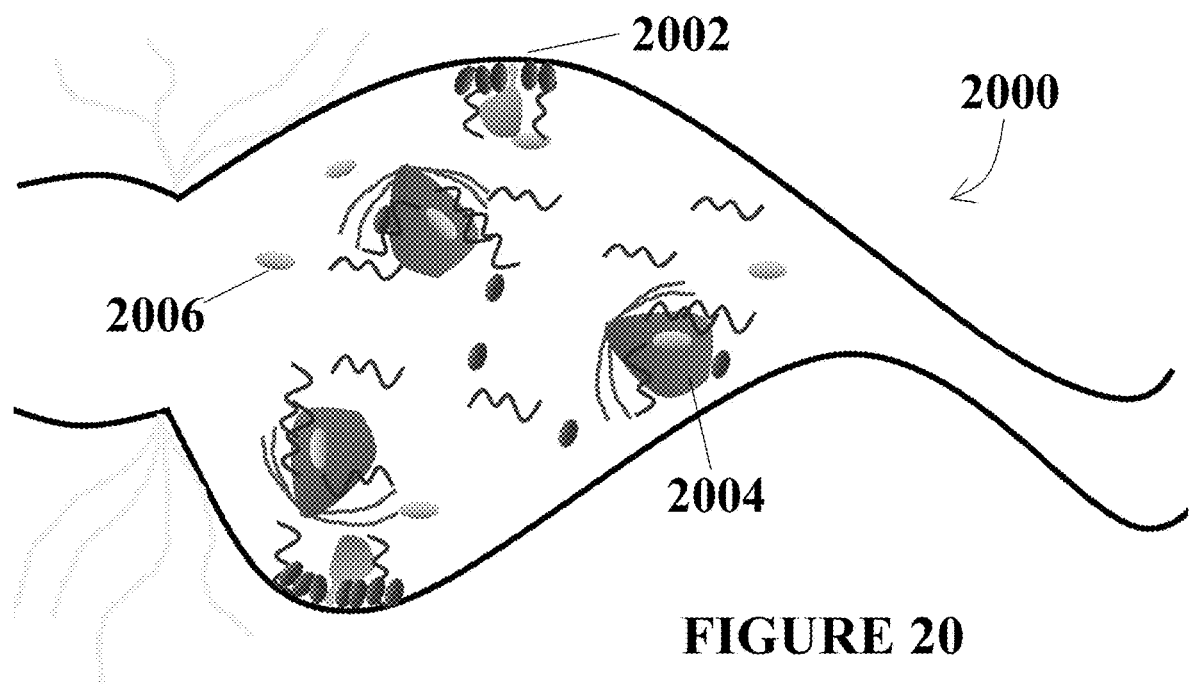
FIGURE 20
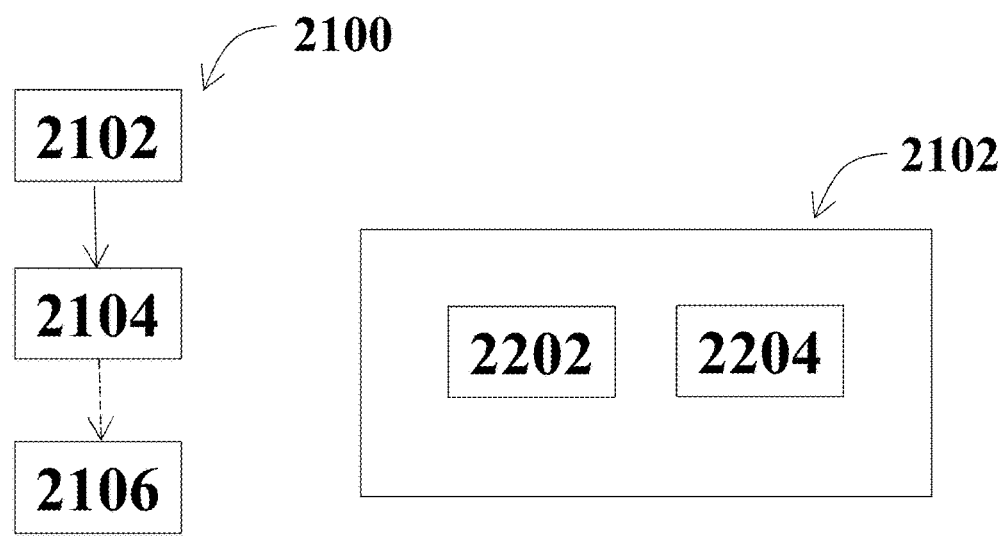
FIGURE 21
FIGURE 22

SEQUENCE LISTING

```
<160> NUMBER OF SEQ ID NOS: 19

<210> SEQ ID NO 1
<211> LENGTH: 1471
<212> TYPE: DNA
<213> ORGANISM: Unknown
<220> FEATURE:
<223> OTHER INFORMATION: unknown protist symbiont species present within
      hindgut of termite Reticulitermes flavipes
<220> FEATURE:
<221> NAME/KEY: misc_feature
<222> LOCATION: (1028)..(1028)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1118)..(1118)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t
<300> PUBLICATION INFORMATION:
<308> DATABASE ACCESSION NUMBER: Genbank / KC751535
<309> DATABASE ENTRY DATE: 2014-04-15
<313> RELEVANT RESIDUES IN SEQ ID NO: (1)..(1471)

<400> SEQUENCE: 1
ttttcatttt ctgaatcatg ctgacttttg tggttgtgtt gctttcattg gttgtgtctc      60
ttgagattgg gactcaacaa acggagactc atcctaaatt gacgtggcag aatggatcaa     120
gttcagtgtc agggtctatt gttcttgatt cgaattggag atgggttcat gacagcggga     180
cgactaattg ttatgatggg aatctgtgga gcagtgatct ttgtccaagt tcagatacat     240
gcacacagaa atgttatatt gagggagcag attattcggg aacttacgga attacgacga     300
gtggttcaaa gttgacgctg aaatttgtta cgaaaggatc gtattcaaca acatcggaa      360 gtcgtgttta cttgttgaaa gatgacaaca cttatgaaac attcaaattg aagaataagg     420
aatttacatt tacggtggat gattctcaac ttgattgcgg actgaatggg gcattgtatt     480
ttgttgcgat ggatgcagat ggtggaaaag caaaatattc agctttcaag ccaggggcta     540
aatatggaat gggatattgt gatgcacagt gcccacatga catgaagttt atcagtggaa     600
aggctaatgt tgatgactgg aaaccacaag acaatgatga aaattcagga aatgggaaac     660
ttggaacatg ctgttcggaa atggatattt gggagggaaa tgcaaagtca caggcatata     720
cagtgcacgc ttgcacgaaa agtggacaat atgaatgtac gggaactgct tgcggagact     780
cagataacag gtatggggga acttgcgaca aagatggatg cgactatgct tcatatagat     840
ggggagacca ctcgttctat ggtgagggta agactgtgga cacgaaacag ccagttacag     900
ttgtcactca gtttatcgga gatccgttga cagaaatcag acgggtttat gttcaaggtg     960
ggaaagtgat tgagaactcg aaaacatcga acttggcttc aacatatgat tcgatcaccg    1020
atgcattntg cgacgcgacg aaagcagcga gtggcgatac taacgatttt aaggcgaaag    1080
gaggcatggc gggattcagt aagaatctgg acnctccnca agtattggtt ttgtcattgt    1140
gggatgatca cncagcgaat atgttgtggc ttgattcgac gtatccaact gattccagtg    1200
```

-continued

```
atccaacagc agcacgtgga ccttgtgcga catcatcagg tgttccaaaa gacgttgaaa      1260
gcgcgcaagc caatgctcaa gttgtatttt cggacattaa gtttgggcc atcaactcga      1320 cttataaagc caattaaaaa ccctttttga gagctcaatt tgggtaagat ttttctttt      1380 tatttgagag tcattcattg tgttttttta aaaagtggtg tttaattatt tttttttttt     1440
tggaagaatt gtttatttgg gaattgatta a                                    1471
```

<210> SEQ ID NO 2
<211> LENGTH: 1482
<212> TYPE: DNA
<213> ORGANISM: Unknown
<220> FEATURE:
<223> OTHER INFORMATION: unknown protist symbiont species present within
      a hindgut of a termite Reticulitermes flavipes
<300> PUBLICATION INFORMATION:
<308> DATABASE ACCESSION NUMBER: Genbank / KC751536
<309> DATABASE ENTRY DATE: 2014-04-15
<313> RELEVANT RESIDUES IN SEQ ID NO: (1)..(1482)

<400> SEQUENCE: 2

```
atgctgaagt ttgtgattgc tttgctttca ttgattgtgt ctctggagat tgggactcag      60
cagacagagc aacatccttc gctaagctgg caacaatgtt cgagtggtgg atcatgcagt     120
tcgaaacagg gttctgttgt tcttgactcg aactggaggt gggttcatga cagcgggaca     180
acaaattgct atgatggaaa cttgtggagc aaagatctgt gcgggagtgc aagcacatgt     240
gattcgaaat gttacattga gggagcagac tactcgggaa cttatggaat tcagagcagt     300
ggatcaaagc tgacgctgaa atttgttacg aagggatcat attcgacaaa catcggcagt     360
cgtgtgtact tgttgaaaga tgagaacacg tatgaaacgt tcaaattgaa gaacaacgag     420
ttcacgttca cagtggatga ttctcaactt gattgtggat tgaatggtgc gttgtacttt     480
gttgctatgg atgcagatgg tggaaaacag aaatattcca acttcaaacc aggggcaaaa     540 tatgaatgg gatattgcga tgcgcagtgc ccacatgaca tgaaattcat cagtggaaaa     600
gcaaatgttg aagactggaa accacaggac aatgatgaaa attcaggaga tgggaaactt     660
ggaacatgct gttcggaaat ggatatttgg gagggaaaca agattgccca ggcatatact     720
gtgcatgctt gcacgaagag tggacaatac gaatgcacgg ggactgcgtg tggagactcg     780
aataatggtg ctaacaacag atatggagga acttgcgaca agacggatg cgactttgct     840 tcgtacagat ggggtgcccg cgatttctat ggtccaggtc tgactgttaa cactcaacaa     900
ccagttacag ttgtgactca gttcattgga gatccgttga cagaaatcaa acgtttctat     960
gttcaaggag gtaaggtgat taataactcg aaaactcaaa acttggcttc atcgtacgat   1020
tcaattactg atgcattctg tgatgctacg aaggtggcaa gtggtgatac taatgatttc   1080
aaagcgaaag gaagcatgtc aggattcagt cagcggttag acactccaca ggttctggtt   1140
ttgtcattgt gggatgacca taccgcgaac atgttgtggc tcgattcgac gtatccaacg   1200
gattcaaagg atgatacagc gaaacgtggg acatgcgcta catcgtcagg tgttccgaaa   1260
gatgttgaaa gccagcaagc aaacgcccaa gttgtatttt cagacatcaa gtttggaccc   1320
atcaactcca cgttcaaatt taattaatct ggccaggaaa tttgatttat tgggttggaa   1380 aagattttt tgagtgttgc attcacttct tttttttttc tttaaagtt gtttattgtg    1440 gtatttggga ggaagaaacc gttcattggt gtgtgcaaaa aa                      1482
```

<210> SEQ ID NO 3
<211> LENGTH: 1967

```
<212> TYPE: DNA
<213> ORGANISM: Unknown
<220> FEATURE:
<223> OTHER INFORMATION: unknown bacterial symbiont species present
      within a hindgut of a termite Reticulitermes flavipes
<300> PUBLICATION INFORMATION:
<308> DATABASE ACCESSION NUMBER: Genbank / GEWY01020352
<309> DATABASE ENTRY DATE: 2016-09-13
<313> RELEVANT RESIDUES IN SEQ ID NO: (1)..(1967)

<400> SEQUENCE: 3
```

| | | | | | |
|---|---|---|---|---|---|
| aattaaaacg | aaaatagtat | ggagctgatg | ccaatacagg | cagaggtata | ttttgccgca | 60 |
| acgaaaaaat | gtcattagac | ttagaggaca | attatcttaa | gattacataa | tttgttaaaa | 120 |
| aaatcaaaac | agtcaaaaca | atactgtttt | gaaagaagac | actaaaaaaa | gggagtaaag | 180 |
| aaatgaaaaa | gttgacttgc | tattgtttaa | tgttgtgcct | tacggttttt | tgttttgttg | 240 |
| gttgtaagga | taaaaaaacc | gctgatgaaa | ccaaaacagg | aaccggatca | gcaggagccg | 300 |
| accagcagaa | taatcagagt | aaataaaaag | gacagaattc | tcgaaagata | cagagaacaa | 360 |
| acacggcaaa | aacaatttaa | tccaccatac | tttgaaaagc | agagtatttt | aatttggctt | 420 |
| ccttattatt | ggattatttg | ttttttgccgg | aaatagagaa | tattatttct | gatattaaaa | 480 |
| accggaaaac | gaatatgtaa | gcaaaaagta | ggaatataag | tttatatatc | tcacaattaa | 540 |
| gcccgaccaa | aaattactga | aatgcaaaag | aaaaatgttg | aaagataaat | taaagagcgt | 600 |
| taaaaaact | tactctttaa | ggaatattga | tagcgtttga | aaagtataag | gcggtaagct | 660 |
| gattgagggg | ggcatctatt | tttttatca | caagaaatgc | agaaagcaaa | agtacatcat | 720 |
| actactataa | agcaacataa | aaaattttaa | ctttactatt | gcttttcta | cttttttcta | 780 |
| tattttactt | atctaattag | agagcaataa | aacctgcaat | ttaatgaaaa | tccggtttat | 840 |
| gacaatactg | aggtaaactc | tctatttttt | agccttaaaa | gattctctta | ctaatttcac | 900 |
| attccattag | atagtttaat | taattgctta | attcgcacat | ttatttagtt | gttcttgaac | 960 |
| atcttgcata | atattttttc | acatttaaag | ttttctttt | ttgcttctttt | tatttaaata | 1020 |
| atccattcgt | atcaacttat | attaagtaaa | ctctttatat | taaaagagag | aattttttcgt | 1080 |
| ttatttttctt | cggatatatt | taaagatttt | ataaaaccaa | cttcttttttc | tggatttcca | 1140 |
| aaaggaaaat | ctgaaccata | aactattta | tcaaacgtgt | gtttattaaa | cagcttgtca | 1200 |
| agcagttctc | ttttcataac | tcttatgcta | tcggaggtgt | caaaatacaa | attttttaccc | 1260 |
| gcaagttttt | ccaaaacttc | tttccatatt | agaaaaccgc | ccatatgagc | gccaataact | 1320 |
| ttaagttccg | aaaattttttc | aagaatttttt | ataatccttt | cgggagaaga | gcgaatttca | 1380 |
| cctgtagaac | tcaattctgc | tccacaatgg | aataacacag | gaattctaaa | ttttttcaagc | 1440 |
| tcttcataaa | gggcgaaagc | tctctcgtcg | tcaacgtaaa | aattctgaaa | ttcaggttgc | 1500 |
| aatttgatac | cggacgcacc | gtcttttatt | ctctttaatt | cttccttaaa | tccctccaag | 1560 |
| aatggatgca | ttgaagcaaa | gagaacaaat | ctttcttctt | tcagcgaaaa | aagccagttg | 1620 |
| tttattggaa | ttacttgctc | ggtatgcgaa | gcaactgatg | atataacgct | ttttgagatt | 1680 |
| tcagctttat | ccatatatgc | caacagatta | tctgcaacag | gcagcgccat | cattttataa | 1740 |
| ttaaaaactt | tttcaagata | atttcttgcc | ttacaagcta | cttctctcagg | ccagatgtga | 1800 |
| ttgtgtgcgt | caatgatatc | cataaatagt | acggggcgct | ccttacttca | aaagcataat | 1860 |
| tgcacagata | agacagatat | catcggcgct | agcacctctg | cttaaatcgc | ttacaggaag | 1920 |
| agcaagtccc | tgaattatag | gacctaagcc | tgaaatccgc | cgtatct | | 1967 |

-continued

```
<210> SEQ ID NO 4
<211> LENGTH: 793
<212> TYPE: DNA
<213> ORGANISM: Reticulitermes flavipes
<300> PUBLICATION INFORMATION:
<308> DATABASE ACCESSION NUMBER: Genbank / GEWY01022384
<309> DATABASE ENTRY DATE: 2016-09-13
<313> RELEVANT RESIDUES IN SEQ ID NO: (1)..(793)

<400> SEQUENCE: 4
aggacaatgc tcaaatttct atcacagcct tatattttat tatacaaaag caacaaattt      60
aataagtctt gaccaatgca agtctgtgca acttattgta atgtacttca caagaattta    120
cagttcttcc tagcagtata ttgtttgaat ttttcattta caacattatc aggaggtaaa    180
tctaaaaatt atagtggcga cttttacat ctgctgatga cctttattaa tgtagcaact     240
tataatgcaa tgtattaaaa cccattgact aaacatcaa agacaatcat aaatgtctgg     300
aagcatttag acatccaaat taatttttc agccagtgaa catgttagtc ctgtgccatc     360
aggttccaca ttgatggact tcacaatgcc atcttcaacc accatcgagt atcgctttga    420
tcgaattcca cccaatggtg gcaaatcagt tgtcagatcc acagcctttg taaatgcagc    480
actgggatca gcaagcattc gaattttccc ttccacttca tatttttac cccaggcttc     540 cataacaaat ggatcgttga cagaaacaca gacaatttca ttcacgcctt tctgtttcag    600
ctcatctgcc ttgcctacat atcctgggag gtgagtcttg gagcagccag gcgtgaaggc    660
tccagggaca gcaaaaatca aactttctt tcccttagtg aggtctgaaa ggtttacttt     720
attggttgga gtattctcat agagctccac acttggaagc ttgtcaccaa cctgcaatac    780
agacacactt cat                                                        793

<210> SEQ ID NO 5
<211> LENGTH: 1313
<212> TYPE: DNA
<213> ORGANISM: Reticulitermes flavipes
<300> PUBLICATION INFORMATION:
<308> DATABASE ACCESSION NUMBER: Genbank / GEWY01022883
<309> DATABASE ENTRY DATE: 2016-09-13
<313> RELEVANT RESIDUES IN SEQ ID NO: (1)..(1313)

<400> SEQUENCE: 5
taccgaggtc gacttagata agaatcaagc tatggtatat attttgcata atactgatac      60
gtcatcttta ttatgcagtt ccaatgttat ttcaaataca ttagacagaa aagtcactat    120
gtgtgactgt gtctggcctt cccatactgc aattattcag cattctacac acatacgtca    180
gaggtagata taactcttgt atctgtgaca gcagttgggg agtcagttac ataatgcgtg    240
acgctagaga tcctctaggt gttattagct actttttcc agcttttgaa tcatacattt     300
ccttaaattt caaacaacct gcatggttca attcttcgta tttaggaatt gtcttctttg    360
cctttgcaag ccacttggag acatttggat actttgcaat gtcaaatcca actacttcaa    420
tggtggatac tgaagccaca agtgaaaaat cagcgatggt gagttggtca ccagcggccc    480
aagcctgatc ctctagatac ttgtcaagaa tttgataccc caactccagt tttgaatact    540
tggctgggtc tggctcggct ccgtcgaaga cgattggtac gtaatagtta atggtccttt    600
gccacaaagt tgtggcatcg aagtacagca tttggttaac cacagcacgc ttctttggat    660
ccttcggata cagagagtca tctttagcat atcgttccac caagtaggct aggatggcac    720
gactttcact tagatgaaat ccattgtcgt ccagggttgg cacgctgtgt tgtgggttaa    780
tcttaaggaa gtctggcgtc agttgttccc cttttagcag attcaagagc ttcaaattca    840
```

| | |
|---|---|
| acttcactcc aacagcattg gctgcgagca gaactgatcg gcacggagca ctggcgggaa | 900 |
| catagtagag atcgacggac atcttgtttg tagcttctca aatccaacag cgtggtactt | 960 |
| cgccagacgt gatatcctat tccactggca gagctgttcg ttttctatca acacatctta | 1020 |
| ttgaggaaca gattaccaca gggtcacgtg acagtgacaa agcaaattcg cttcagaagg | 1080 |
| gttacgtaac acgtttgttc tgccatctgg taggaacgta ggaaactctg cctgcgcctc | 1140 |
| tgctgggaag accttgtcgc gccaccactt tttatgtgct gctaattgtt tatgctttaa | 1200 |
| acttcctgct tctttgttct gtctgcctag cctgcagatg tgtagaaaat tgtgtattgt | 1260 |
| acgcattggc tgcaagattt caaggcgcgt tcgcacgtgc atagtgcaaa ttc | 1313 |

<210> SEQ ID NO 6
<211> LENGTH: 1721
<212> TYPE: DNA
<213> ORGANISM: Reticulitermes flavipes
<300> PUBLICATION INFORMATION:
<308> DATABASE ACCESSION NUMBER: Genbank / GEWY01020528
<309> DATABASE ENTRY DATE: 2016-09-13
<313> RELEVANT RESIDUES IN SEQ ID NO: (1)..(1721)

<400> SEQUENCE: 6

| | |
|---|---|
| tgcattaaac tgtactataa cagaatctgt tcatgcaagt agtaatgaca tatccctggc | 60 |
| agtttcagac aatactttg tcataacagc gttctggtac ctgtcattcc aacaccagac | 120 |
| acaacctacc tacgctaaca atatatgcat acagtacgcg ttttccttt tttttttttt | 180 |
| taaccaccaa ttaaaattct gtattatcct tttattgct tttctttaac agacacaata | 240 |
| aagatcacac attgcccaat acatatatga acatctgaaa cttcaaaggt gttgagagtg | 300 |
| atggaatgaa cagcctcttg gcgtatgtat gtcatattgt tctctgttcc acatatacta | 360 |
| agtgcgcacac tgacacatca gaatgccatc aaataacact acaagaaaaa taatcacata | 420 |
| ctccaatctt ccacactgct ctcattactg taaaaattta cctcttagtc aaatattgca | 480 |
| tacaatttct gaatactaac aaaagacaac cagctgtata attatgtgat actaacttcc | 540 |
| tttagagaaa tttcaaaatt agaatatacc gacagtaatc agttaccacc gctaagtaaa | 600 |
| actaccagct gctctgtgta acacagaact ccaatgcctt gtttaattac aattccccat | 660 |
| tgagcagctt cttgtcaaac agaaattctc caagggttcc ataatagtcc agcatcttgc | 720 |
| ccagtgttga tatcttacca gcaaggtctg attgaccttt gtactgctcc tctaggaaat | 780 |
| cgccgctgag ataatcaacc agatggtaat cattgaaacc cttttccatca tcagatggat | 840 |
| tctcacaagc aatgatgatg tcacgtatct tgcgagtaac atgtgcctcc agtttcaatg | 900 |
| cgtccttcag ggcatcgata ccagattccc agctctcgtt gagggcatt gggttctgaa | 960 |
| tgagtttgct gatttcagat gtaagttcac cacgcatgag caagtatgaa attattttta | 1020 |
| tggcgtgctg acgttcttca cttgcagcct caaagaacag cttggcaaaa ccaggtctgt | 1080 |
| ttattgtgtc ccttgaaaag tgagcgccca ttgccatgta agtaagcgca gctagcagct | 1140 |
| cctcttgcac ctgttccctc atttttcaggg tgcaaggctc caccatggtg atccagtcct | 1200 |
| ttggaatttc aactggaggc agcgtacatg tcaatttgc agtcacagca tgtgcacaga | 1260 |
| ttgcaactac gacaaaaatt attgcttgca cggatttcat tgttgaagaa tacttttcctt | 1320 |
| ccaacggaaa cgagtgtcac ggtttagtta ggttatttca attgtcttac acacaaattc | 1380 |
| agtgaaaacg actggaaaat tgtgaaaatg taacaacagg caaaggcaaa tactagtata | 1440 |
| ttttacaaac acttgatctt ttgtcaacct ttacacacac tggcgtagaa ggcgacacaa | 1500 |
| cctatcaccc gcgatatatc ttagctaatg cctacgacga actcatccgt ccaatcgcac | 1560 |

```
ctaattatac atgtactcat ggatcagagt atggcgtcat gctcatttcc ctattgcgca    1620
gtttcatgct gcgtgcgcac ttggcacgtg atgtggaagt gccctatcga tgatggtgca    1680
atattctgca tcacaaaggt cttaaagagc atcaaagatt t                        1721
```

<210> SEQ ID NO 7
<211> LENGTH: 351
<212> TYPE: DNA
<213> ORGANISM: Reticulitermes flavipes
<300> PUBLICATION INFORMATION:
<308> DATABASE ACCESSION NUMBER: Genbank / GEWY01027696
<309> DATABASE ENTRY DATE: 2016-09-13
<313> RELEVANT RESIDUES IN SEQ ID NO: (1)..(351)

<400> SEQUENCE: 7

```
caacacttgg tccccaactc tcacagacag tgggacatgt tcaccattct gatttctaga     60
accaggtcca acagcaacca ctgttccacg caacaccttg gcctgggctt tttcggaat     120 aacaataccc ccctttgtct tgttacagc ttcagctctc tgaatcagaa ctctatcaaa    180
aagaggaatc aatcgcttag ccacattagt agctgcatgt gttgccattt taattaatga    240
aaactgtacg acaccgacta atacacaaca aacttagctt ccgtattcgt atctagcacc    300
ctcaccaaac cttgcacgaa acttctagac ttacacaccg gccatctaca c             351
```

<210> SEQ ID NO 8
<211> LENGTH: 319
<212> TYPE: DNA
<213> ORGANISM: Reticulitermes flavipes
<300> PUBLICATION INFORMATION:
<308> DATABASE ACCESSION NUMBER: Genbank / GEWY01028178
<309> DATABASE ENTRY DATE: 2016-09-13
<313> RELEVANT RESIDUES IN SEQ ID NO: (1)..(319)

<400> SEQUENCE: 8

```
taaattttcc gctataaaat ggtacatatt ggagtactgc ctgccagtcc gtaaaatata     60
aaaatccaag acttccagct gctccaaatg ttgccaaaga aggtgcccag taactcgcta    120
gttcaaaatg ccttttccct atctgccgca acagcgacat gactgttatt atactctccg    180
cgaagcaaat acagacacac cgacttcgta gccactaatg gtacttcgct ggctatcact    240
cacaaccagc aacaaaatca caaccacagg tcgggtcaca cagaggccag agataaccca    300
catcaaagag aatcaatcc                                                 319
```

<210> SEQ ID NO 9
<211> LENGTH: 421
<212> TYPE: DNA
<213> ORGANISM: Reticulitermes flavipes
<300> PUBLICATION INFORMATION:
<308> DATABASE ACCESSION NUMBER: Genbank / GEWY01006445
<309> DATABASE ENTRY DATE: 2016-09-13
<313> RELEVANT RESIDUES IN SEQ ID NO: (1)..(421)

<400> SEQUENCE: 9

```
cttcttcttc ttcttttct tgtcgctccc tagttacttc ttcaaggtat ggctttaagt     60
atttgttatc ttcctcaaat tttacccact cttcttttgg caatatggtc ttctggattg    120
acaactgcat ggcacgcata atccgaaagt tacgttcatc taccaaatgt gctggcaatc    180
gtcttaaagc ttcctttaca tctggtatat cctcatcata acagtcatca tggtgaaggc    240
cgtatttatt gaagccagac agattgtatg cccaccttct gatcgcaacc gcaaatcctg    300
aagctttcga cacggacatt tcctgccgca gaataggcaa atttattctt cttctcttcc    360
```

| | |
|---|---|
| aacttgtgca gcctgcgaaa cccaagaact caccacagat gatctcgagc aacccggtga | 420 |
| a | 421 |

<210> SEQ ID NO 10
<211> LENGTH: 478
<212> TYPE: DNA
<213> ORGANISM: Reticulitermes flavipes
<300> PUBLICATION INFORMATION:
<308> DATABASE ACCESSION NUMBER: Genbank / GEWY01004504
<309> DATABASE ENTRY DATE: 2016-09-13
<313> RELEVANT RESIDUES IN SEQ ID NO: (1)..(478)

<400> SEQUENCE: 10

| | |
|---|---|
| tcaaaagttt caggaaaatc ctaacattac aaactctaat tacaaaaatt gttacaggaa | 60 |
| cagggcataa tacagtcaac cttggaaggt gcttttaaac aactgtgcca ggtctttaag | 120 |
| ttaaaaaatt ggcccacttt catcttacca gttaatataa agaggaacat tattaacggt | 180 |
| attgatttat tacacaataa gagctacgta catctgtcta ttacgatccg tacgatgtta | 240 |
| tttggtaatc tcggccagtt tcggcacctc acttcattca taattatgtt tgatgtgctt | 300 |
| ccataatttc ccacgattga ttgagtcaaa aatgtactcc gacgttacat caaaagtacg | 360 |
| ctcgaaacaa aatgccccca acattattgt tgctgcaaaa gttgatgttc ttctgaaaag | 420 |
| agcattatac actttctgtg ctactccagc cattttacca ccaccacgaa tgagaacc | 478 |

<210> SEQ ID NO 11
<211> LENGTH: 255
<212> TYPE: DNA
<213> ORGANISM: Reticulitermes flavipes
<300> PUBLICATION INFORMATION:
<308> DATABASE ACCESSION NUMBER: Genbank / GEWY01020290
<309> DATABASE ENTRY DATE: 2016-09-13
<313> RELEVANT RESIDUES IN SEQ ID NO: (1)..(255)

<400> SEQUENCE: 11

| | |
|---|---|
| tgtgtcccta ttccaagtga taccctttgga cttattggca tctgtgtaaa caaaccctga | 60 |
| tgcctgccca gttttttcgtc caattagccc atgcagattg gggccagttt tgtgcttgcc | 120 |
| acctgttttct acagtatggc actgggcaca cctctgaacg aaaaccttct ttccctttc | 180 |
| tgcatcaccg tctggaactc ccatctttcg gcgcttctgg aaaggtacct caccgatctg | 240 |
| accccctagcc ttgcc | 255 |

<210> SEQ ID NO 12
<211> LENGTH: 563
<212> TYPE: DNA
<213> ORGANISM: Reticulitermes flavipes
<300> PUBLICATION INFORMATION:
<308> DATABASE ACCESSION NUMBER: Genbank / GEWY01020030
<309> DATABASE ENTRY DATE: 2016-09-13
<313> RELEVANT RESIDUES IN SEQ ID NO: (1)..(563)

<400> SEQUENCE: 12

| | |
|---|---|
| cccatttcat ttcatttcac aaggaacaaa caaaaaatta aatttaccttt tacctcagaa | 60 |
| gtcactactc cgatggcacg gccaccggct gttaactaaa actgtcccag ctatcaaatt | 120 |
| tgaagtcaag tctgcatata caacactgct atgcatggcg actttaaatt tttcctggga | 180 |
| atcggttttc ttcacgttgt gtgtcccatt tttcaaccca ggcaaatggg caaagacttt | 240 |
| cgtagcattt acggaaataa ttgcatggtt catattttc tcccttcagt ttgcggcacc | 300 |
| ggtgatagtc aacatagctc tgccagcagt accgagtctg gttctgattt gggaatcgtg | 360 |
| gatcaaaagg agcagtagag aattcaaact ttggttcttc cttcttgcca gccatgacag | 420 |

```
caagagaggg cattgcaagt gaaattactc tcttgtaact gaataaaatg gccgacaacc    480
gtaagagaag gttatttcat tgtaaataga ttgcactgcg atctgacggt aaacgagaaa    540
gttacgccct gaccaacagt act                                            563
```

<210> SEQ ID NO 13
<211> LENGTH: 468
<212> TYPE: DNA
<213> ORGANISM: Reticulitermes flavipes
<300> PUBLICATION INFORMATION:
<308> DATABASE ACCESSION NUMBER: Genbank / GEWY01011866
<309> DATABASE ENTRY DATE: 2016-09-13
<313> RELEVANT RESIDUES IN SEQ ID NO: (1)..(468)

<400> SEQUENCE: 13

```
atcataatta cacaaaatga aaatgttttt tcagcattcc aaacacttat aaaactttc      60 agttcacttt tccggtgcac tacaacatac ctacaaaata tctattcaca acatattgtg    120
attcattaga tcaacagctc ttgaatacac cagcttttct catcctttca aaatccttct    180
ctgcatcata attcttgtag aattctgcgt atctagcttt ccgggcatcc acccagaata    240
tcttgaataa aactgtagca acagcactaa ggctaagtgc tacaggaaga tggaacttca    300
cattagatgc aagtaatcct ctcaactggg gcttgggtat cttttgcaca gacttttcag    360
ccatcttcga ttatcaagct ctatttctta caaaagaga gcaagaatta tacaacacaa    420
tttacggttt cacggagtgc acagacgata acagatgtga ggcaaaac                468
```

<210> SEQ ID NO 14
<211> LENGTH: 718
<212> TYPE: DNA
<213> ORGANISM: Reticulitermes flavipes
<300> PUBLICATION INFORMATION:
<308> DATABASE ACCESSION NUMBER: Genbank / GEWY01005545
<309> DATABASE ENTRY DATE: 2016-09-13
<313> RELEVANT RESIDUES IN SEQ ID NO: (1)..(718)

<400> SEQUENCE: 14

```
atctattacc atctgagcca actctggtat cacggattca gaaaaatgga aaaatcacag     60
gtctctatta agaacagaag tagattctca aaacaacttg acaacattta tgtactgtac    120 aaatttatt ctatttgtct gttaaacaat aaacatgtga gcaaataact catttaccat    180
tcccacaaca tgtgaaaaaa gaaaattctc atgtcagttg taatgtagtg ttcattacta    240 gcttttcct aaatttctgc agactaaatg caacactta cttcttcaat agctgatgcc    300
tcagtacaaa gaatggagca gccagtccac ttccaaagaa aactatgaac agtgctgtca    360
gtttatagcg gtttgtgatg tcaaatggaa ggttccctcc aggaattcca ccatgatcat    420
gtccaccact tcgcctgatg gctgaagtaa cgaaatttct tgcaaactga aaacccttc    480 cagacatatt cggtctctat aattaccagc tgaacaggca ggaagttcaa cctacaacgc    540
agttagtcaa cccaaagaat gtaacgaatc gcagacgata tgttacgact cgtataacaa    600
tgtttctttt tatgtaaatg ttaattcaag gcagtataag tttcagtgga gatcgacgta    660
tgaataactg acaagaatgt cattattggt ttgaccatat tatatggttg cttgaaat     718
```

<210> SEQ ID NO 15
<211> LENGTH: 333
<212> TYPE: DNA
<213> ORGANISM: Reticulitermes flavipes
<300> PUBLICATION INFORMATION:
<308> DATABASE ACCESSION NUMBER: Genbank / GEWY01029399
<309> DATABASE ENTRY DATE: 2016-09-13

<313> RELEVANT RESIDUES IN SEQ ID NO: (1)..(333)

<400> SEQUENCE: 15

```
atatctggca gaaagactta tatccaaaac tggaagttta ctcttcgttt gtattcactc    60
tgaggaccat gggcataaaa ttcactcatg tggggtgtaa ccaatgtatc tggaggaagc   120
gttttgtata ctggctcccc ataccatgtg ccaactaccc aacctggtac actgccatc   180
aacttagctt cttcatcgcg attacgacgt aactgcttca agtactctct gtctcgctcc   240
gccataagca gtggcgttaa cgcaagttta gcacttctca tttcaattga atcttgccta   300
accttcttcc aagtgaggta atacacataa ccg                                333
```

<210> SEQ ID NO 16
<211> LENGTH: 329
<212> TYPE: DNA
<213> ORGANISM: Unknown
<220> FEATURE:
<223> OTHER INFORMATION: unknown protist symbiont species present within a hindgut of a termite Reticulitermes flavipes
<300> PUBLICATION INFORMATION:
<308> DATABASE ACCESSION NUMBER: Genbank / GEWY01018124
<309> DATABASE ENTRY DATE: 2016-09-13
<313> RELEVANT RESIDUES IN SEQ ID NO: (1)..(329)

<400> SEQUENCE: 16

```
cacggtcacg aacgcgtcca ccttcagctc gatgtccgcg agacgaggta cgaacacctt    60
gtagtcgtcc gggttcagct tcagcgcacg cactaactgt cctatgcgct tgttcttgtc   120
cgccacctcc tgctccgtcc gtcgtttccg ctccagcatc tgatcgaaga aagtgttaaa   180
ctcggtcgcc tcgcgtcgca cggcatcgcg cagcagccag acctgcgtca cgcgccggtt   240
cccagactga agctccagcc cctcgtacaa gagcgtctca ggcgtcggct gcccgagcgc   300
agccagctcc gtcctacgaa gcatcgaca                                     329
```

<210> SEQ ID NO 17
<211> LENGTH: 501
<212> TYPE: DNA
<213> ORGANISM: Unknown
<220> FEATURE:
<223> OTHER INFORMATION: unknown protist symbiont species present within a hindgut of a termite Reticulitermes flavipes
<300> PUBLICATION INFORMATION:
<308> DATABASE ACCESSION NUMBER: Genbank / GEWY01027694
<309> DATABASE ENTRY DATE: 2016-09-13
<313> RELEVANT RESIDUES IN SEQ ID NO: (1)..(501)

<400> SEQUENCE: 17

```
ttttttttt aaaagaagtc aattttttaat tagcttcgtc ataaccttgt tcatcagtcc    60
agagttgaac attatctttc aaagttgga gaatcaaagt ggcctcagaa tattcatctt   120
ctggaaggtc gtcaagaaga tcgacagcgt ttttgaatgt tttatcagct aattgaatgg   180
cttcagtttt catgccatcg atttcataca aaaatacaga atagttaaga gcaagaccca   240
aaaactgggg gttagctttt gtcaattgtt cttgagcaat ttccattgca gattcataag   300
attgtttagc tttgtcacta cctgactttc ttgcatcacc ttccttaaat tcaacgctat   360
aacggtagta atcagctttg agcttttcgt aaaaaacttt gttagcagct tcagttgaag   420
atggaagaag tttagaatca acaagctcaa caatttcatt acaataatca tcaagctctt   480
tcaataagac acttcggaga t                                             501
```

<210> SEQ ID NO 18
<211> LENGTH: 297

```
<212> TYPE: DNA
<213> ORGANISM: Unknown
<220> FEATURE:
<223> OTHER INFORMATION: unknown protist symbiont species present within
      a hindgut of a termite Reticulitermes flavipes
<300> PUBLICATION INFORMATION:
<308> DATABASE ACCESSION NUMBER: Genbank / GEWY01004795
<309> DATABASE ENTRY DATE: 2016-09-13
<313> RELEVANT RESIDUES IN SEQ ID NO: (1)..(297)

<400> SEQUENCE: 18 tttttttttgg gaaaacaaaa aagtttattt acccacactt ccaaagttga actgcaactt      60
gaccaatata aaagtaaatg aaatgtttgg tttcatgggt aacaaaagaa ccaaacgatc     120
ttccaacaac ggcatgccat gttgggttat atttcttatc aaattccttt ttgatatatg     180
aggcaatatc tttttcgata ttgaacctat ctaaagcttg agttgcaata tcgattgcat     240
cagtttgcat ttcttcggac atatcaacat tcttgataac agcacgctta tcttgag       297

<210> SEQ ID NO 19
<211> LENGTH: 379
<212> TYPE: DNA
<213> ORGANISM: Unknown
<220> FEATURE:
<223> OTHER INFORMATION: unknown protist symbiont species present within
      a hindgut of a termite Reticulitermes flavipes
<300> PUBLICATION INFORMATION:
<308> DATABASE ACCESSION NUMBER: Genbank / GEWY01009874
<309> DATABASE ENTRY DATE: 2016-09-13
<313> RELEVANT RESIDUES IN SEQ ID NO: (1)..(379)

<400> SEQUENCE: 19
tggatatctg catcatcatt agcttgaagt tccaatgcaa ctcctgttaa cgcattcttg      60
attgaagctt ttgatccagt aataagcatc tttctcttag gaggtgcaac atctggtgcc     120
catacaacaa aaacaatttt gtttctttca gttccatctt caaccttgaa ttcataatca     180
tagatagcat atctcacatc ttttggtgga agagaatcca agaaattgtc ataagttgct     240
gtaactggag ctttcttgtc aataacaatt tctctaaggt catttgagaa ggtaaaagta     300
acataacgat acttgtgacc aattttgaat tcgttccaaa gctgaattgc ttcatcagca     360
acagcgatac cagtcatag                                                  379
```

METHODS, COMPOSITIONS, AND MOLECULAR TARGETS THAT EXPLOIT SYNERGIES AND SYMBIOSES IN THE TERMITE GUT

PRIORITY

The present application is related to and claims the priority benefit of U.S. Provisional Patent Application Ser. No. 62/316,781 to Scharf et al., filed Apr. 1, 2016. The disclosure of the aforementioned patent application is hereby incorporated by reference in its entirety into this disclosure.

STATEMENT REGARDING FEDERALLY SPONSORED RESEARCH

This invention was made with government support under 2010-65106-30727 awarded by the USDA NIFA National Institute of Food and Agriculture. The United States Government has certain rights in the invention.

BACKGROUND

Subterranean termites have lifestyles that are ideal for disease development. They live in moist, protected environments that are well suited for microbial growth and, because they are eusocial, colony members are in constant close contact. Despite these conditions that are favorable for the transmission of disease, termite epizootics are uncommon; to date, very few entomopathogens have been discovered in nature that infect these insects. This observed disease resistance is thought to be attributed, at least in part, to the social behaviors of these insects that facilitate pathogen removal and transfer of resistance factors among nestmates.

As do solitary insects, termites respond at the individual level to microbial pathogens by eliciting innate defense responses involving both cellular and humoral reactions. Exposure of termites to sublethal pathogen challenges has been found to trigger a defense reaction that produces sustained resistance to subsequent pathogen exposure. In fact, the presence of various pathogen-recognition proteins (PRPs) and the transcription factor relish has been reported in various termite species. Both relish and PRPs appear to undergo positive selection, suggesting a molecular arms race between pathogens and termite innate immune systems. In addition to the inducible innate response, certain termite species constitutively express antimicrobial peptides (AMPS) that display potent antifungal activity. Analysis of gut transcriptome databases further suggests that termites have a functional innate immune response complete with a complex of recognition components, transcription factors, and AMPS. Additionally, certain components of the innate defense system may have multifunctional roles. For example, lysozyme—a known AMP and digestive enzyme—can serve as an egg recognition pheromone in termite colonies and gram-negative bacteria-binding proteins (GNBPs) are structurally homologous to cellulases used by termites and other organisms for digesting their principal dietary component lignocellulose. Likewise, endogenous endoglucanases (well known for cellulose depolymerization) have been found to be inducible by pathogen challenge.

Another pertinent characteristic of termites is the presence of commensalistic microbiota in their digestive tracts that assist in lignocellulose digestion, nitrogen fixation, and intermediary metabolism. How these commensals survive, multiply, and cycle through the termite gut via trophallaxis without triggering an antimicrobial response in the alimentary tract remains unclear. The lower termites, in particular, host diverse gut microbial communities consisting of both eukaryotes (protists) and prokaryotes (bacteria and archaea). Recent analyses of lower termites indicate that they can contain more than 12 protist species and more than 5,000 species-level bacterial phylotypes. Historically, the role of these symbionts has been attributed to the nutritional welfare of the host.

Because termites are structural pests, lower termites are the intended targets of many soil insecticides. One important group of soil termiticides is the nicotinoid class. While effective for pest management and ectoparasite control, soil insecticides such as nicotinoids can have deleterious impacts on non-target species—in particular, honey bees. Accordingly, compositions and methods for increasing the efficacy of conventional soil termiticides—and, in particular, nicotinoids—are needed.

BRIEF DESCRIPTION OF THE SEQUENCE LISTINGS

SEQ ID NO. 1 is a cDNA nucleic acid sequence from an unknown protist symbiont species that can be translated into recombinant GHF7-5 cellulase which, according to the subject disclosure, exhibits antifungal properties.

SEQ ID NO. 2 is a cDNA nucleic acid sequence from an unknown protist symbiont species that can be translated into recombinant GHF7-6 cellulase mRNA which, according to the subject disclosure, exhibits antifungal properties.

SEQ ID NO. 3 is a cDNA nucleic acid sequence from an unknown bacterial symbiont species that can be translated into the gene that encodes amidohydrolase 2 which, according to the present disclosure, is upregulated in response to *B. bassiana* challenge.

SEQ ID NO. 4 is a cDNA nucleic acid sequence from the termite *R. flavipes* that can be translated into the gene that encodes peroxiredoxin-mitochondrial which, according to the present disclosure, is upregulated in response to *B. bassiana* challenge.

SEQ ID NO. 5 is a cDNA nucleic acid sequence from the termite *R. flavipes* that can be translated into the gene that encodes glutathione s-transferase which, according to the present disclosure, is upregulated in response to *B. bassiana* challenge.

SEQ ID NO. 6 is a cDNA nucleic acid sequence from the termite *R. flavipes* that can be translated into the gene that encodes ferritin which, according to the present disclosure, is upregulated in response to *B. bassiana* challenge.

SEQ ID NO. 7 is a cDNA nucleic acid sequence from the termite *R. flavipes* that can be translated into the gene that encodes heat shock protein which, according to the present disclosure, is upregulated in response to *B. bassiana* challenge.

SEQ ID NO. 8 is a cDNA nucleic acid sequence from the termite *R. flavipes* that can be translated into the gene that encodes cytochrome b-c1 subunit 10 which, according to the present disclosure, is upregulated in response to *B. bassiana* challenge.

SEQ ID NO. 9 is a cDNA nucleic acid sequence from the termite *R. flavipes* that can be translated into the gene that encodes cytochrome b-c1 subunit 7 which, according to the present disclosure, is upregulated in response to *B. bassiana* challenge.

SEQ ID NO. 10 is a cDNA nucleic acid sequence from the termite *R. flavipes* that can be translated into the gene that encodes cytochrome b-c1 subunit 9 which, according to the present disclosure, is upregulated in response to *B. bassiana* challenge.

SEQ ID NO. 11 is a cDNA nucleic acid sequence from the termite *R. flavipes* that can be translated into the gene that encodes cytochrome c which, according to the present disclosure, is upregulated in response to *B. bassiana* challenge.

SEQ ID NO. 12 is a cDNA nucleic acid sequence from the termite *R. flavipes* that can be translated into the gene that encodes cytochrome c oxidase subunit 6B which, according to the present disclosure, is upregulated in response to *B. bassiana* challenge.

SEQ ID NO. 13 is a cDNA nucleic acid sequence from the termite *R. flavipes* that can be translated into the gene that encodes cytochrome c oxidase subunit 6C which, according to the present disclosure, is upregulated in response to *B. bassiana* challenge.

SEQ ID NO. 14 is a cDNA nucleic acid sequence from the termite *R. flavipes* that can be translated into the gene that encodes cytochrome c oxidase subunit 7C which, according to the present disclosure, is upregulated in response to *B. bassiana* challenge.

SEQ ID NO. 15 is a cDNA nucleic acid sequence from the termite *R. flavipes* that can be translated into the gene that encodes NADH dehydrogenase 1 alpha subunit which, according to the present disclosure, is upregulated in response to *B. bassiana* challenge.

SEQ ID NO. 16 is a cDNA nucleic acid sequence from an unknown protist symbiont species that can be translated into the gene that encodes 3'-5' exonuclease which, according to the present disclosure, is upregulated in response to *B. bassiana* challenge.

SEQ ID NO. 17 is a cDNA nucleic acid sequence from an unknown protist symbiont species that can be translated into the gene that encodes 3'-5' exonuclease-DNA polymerase I which, according to the present disclosure, is upregulated in response to *B. bassiana* challenge.

SEQ ID NO. 18 is a cDNA nucleic acid sequence from an unknown protist symbiont species that can be translated into the gene that encodes calcium-calmodulin dependent kinase II (CAMKII) which, according to the present disclosure, is upregulated in response to *B. bassiana* challenge.

SEQ ID NO. 19 is a cDNA nucleic acid sequence from an unknown protist symbiont species that can be translated into the gene that encodes mitogen-activated protein kinase 1 (MAPKI) which, according to the present disclosure, is upregulated in response to *B. bassiana* challenge.

In addition to the foregoing, written Sequence Listings for the above-identified sequences are appended hereto and the same Sequence Listings are provided in computer readable form encoded in a file filed herewith and herein incorporated by reference. The information recorded in computer readable form is identical to the written Sequence Listing provided herein, pursuant to 37 C.F.R. § 1.821(f).

BRIEF SUMMARY

Embodiments of the present disclosure provide methods for controlling termite populations that involve attenuating a host termite's innate responses to increase pathogen virulence. In at least one exemplary embodiment, a method for controlling termite populations comprises the steps of: administering a composition to a termite, the composition formulated to promote symbiont dysbiosis in a gut of the termite; and exposing the termite to a pathogen. In such methods, administering the composition increases the susceptibility of the termite to the pathogen which, for example and without limitation, may comprise an entomopathogenic fungi. The composition to be administered may be formulated to alter antimicrobial transcripts present within the gut of the termite. Additionally or alternatively, the composition may be formulated to eliminate one or more symbionts present within the gut of the termite that induce upregulation of an antimicrobial host gene.

Additional embodiments of the method further comprise the step of compromising immune-related behaviors of the termite by administering a neonicotinoid. Such neonicotinoid may comprise impidacloprid, for example, in an amount equivalent to a nonlethal dosage. Still further, the method may also comprise the step of downregulating at least one symbiont gene present within the termite. There, the step of exposing the termite to a pathogen may upregulate at least one antimicrobial host gene of the termite and the expression of a protein encoded by such at least one antimicrobial host gene. The at least one downregulated symbiont gene may comprise a gene that encodes a protist glycosyl hydrolase family 7 cellulase, wherein beta 1, 3-glycosidase activity is reduced by such downregulation. Additionally or alternatively, the protein is selected from the group consisting of: allatostatin, neuropeptide F, lysozyme, pathogen-recognition proteins, termicin, leucine-rich repeat proteins, and/or transferrins. In at least one exemplary embodiment, the method may also further comprise the step of decreasing expression of one or more transcripts that encode the protein using an RNA interference technique.

Methods for treating a fungal infection using glycosyl hydrolase family 7 cellulase are also provided. In at least one exemplary embodiment, a method for treating a fungal infection comprises the step of administering a composition to a patient, the composition comprising a medically-effective amount of recombinant glycosyl hydrolase family 7 cellulase. In at least one embodiment, the recombinant glycosyl hydrolase family 7 cellulase is translated from SEQ. ID No. 1 or SEQ. ID No. 2. The patient may comprise a mammal (such as a human or animal).

Methods are also provided for controlling termite populations comprising the steps of: manipulating expression of a targeted gene to compromise one or more defense mechanisms of a termite; and exposing the termite to at least one pathogen; wherein manipulating the expression of the targeted gene increases the susceptibility of the termite to one or more of the at least one pathogens. At least one of the one or more defense mechanisms of the termite may comprise a social behavior of the termite. Additionally, at least one of the at least one or more defense mechanisms of the termite may comprise a protist symbiont population or a bacteria symbiont population present within a gut of the termite. Where a defense mechanism comprises a protist symbiont population present within the gut (for example, a gene that encodes a protist glycosyl hydrolase family 7 cellulase), the step of manipulating the expression of a targeted gene may comprise downregulating at least one symbiont gene of a protist present within the protist symbiont population. Still further, the step of downregulating the expression of at least one symbiont gene may further comprise using RNA interference techniques or inhibiting the at least one symbiont gene with one or more pharmaceutical agents. In such embodiments, the at least one pathogen may comprise an entomopathogenic fungi and/or a bacteria.

In certain embodiments of the methods for controlling termite populations of the present disclosure, the at least one of the one or more defense mechanisms may comprise a bacteria symbiont population present within the gut of the termite. In such embodiments, the at least one pathogen may comprise a bacteria and a fungi and the targeted gene may comprise a gene that encodes a protein selected from a group consisting of: amidohydrolase 2, peroxiredoxin-mitochondrial, glutathione s-transferase, ferritin, heat shock protein, cytochrome b-c1 subunits 7, 9, and 10, cytochrome c, cytochrome c oxidase subunits 6B, 6C, and 7C, NADH dehydrogenase 1 alpha subunit, 3'-5' exonuclease, 3'-5' exonuclease-DNA polymerase I, $Ca^{2+}$-calmodulin dependent kinase II (CAMKII), and mitogen-activated protein kinase 1 (MAPKI). In at least one exemplary embodiment, the step of manipulating the expression of a targeted gene further comprises downregulating the expression of the targeted gene (for example, by administering a therapeutically-effective amount of kanamycin to the termite or through other available means).

BRIEF DESCRIPTION OF THE DRAWINGS

FIGS. 13A-13C show Venn diagrams illustrating common array positions in 2-way (FIG. 13A) and 3-way comparisons involving FI (FIG. 13B) and BI (FIG. 13C) treatments, with paired FI and BI treatments having many more positions in common than did single F, B, or I treatments;

FIGS. 19A and 19B are bar graphs of results of post-hoc investigations of bacterial Amidohydrolase 2 gene expression and *B. bassiana* susceptibility following treatment with the antimicrobial drug kanamycin (Kan), with FIG. 19A showing relative Amidohydrolase 2 expression following *B. bassiana* pathogen challenge with and without 48-h 5% Kan treatment (control group represents the fold-change in Amidohydrolase 2 gene expression in pathogen challenged termites relative to the unchallenged, water-treated controls; the 5% Kan group represents the fold-change in Amidohydrolase 2 gene expression in 5% Kan-treated, pathogen challenged termites relative to unchallenged, Kan-treated controls) and FIG. 19B showing normalized mortality at 7-days post inoculation with *B. bassiana*, following either water (control) or 5% Kan treatments (bars represent normalized mortality to the respective controls of each group, i.e. water treated, unchallenged controls or 5% Kan-treated, unchallenged controls); error bars representative of standard error of the means across 3 biological replicates;

FIG. 20 shows a model of at least one exemplary embodiment of collaborative immune physiology as provided in the present disclosure, with protists, bacteria and termite host all contributing to neutralizing fungal invaders within the termite hind-gut;

FIG. 21 shows a flow-chart representative of at least one exemplary embodiment of a method of the present disclosure for controlling termite populations; and FIG. 22 shows a representation of a step of the method shown in FIG. 21.

DETAILED DESCRIPTION

Figure 1:
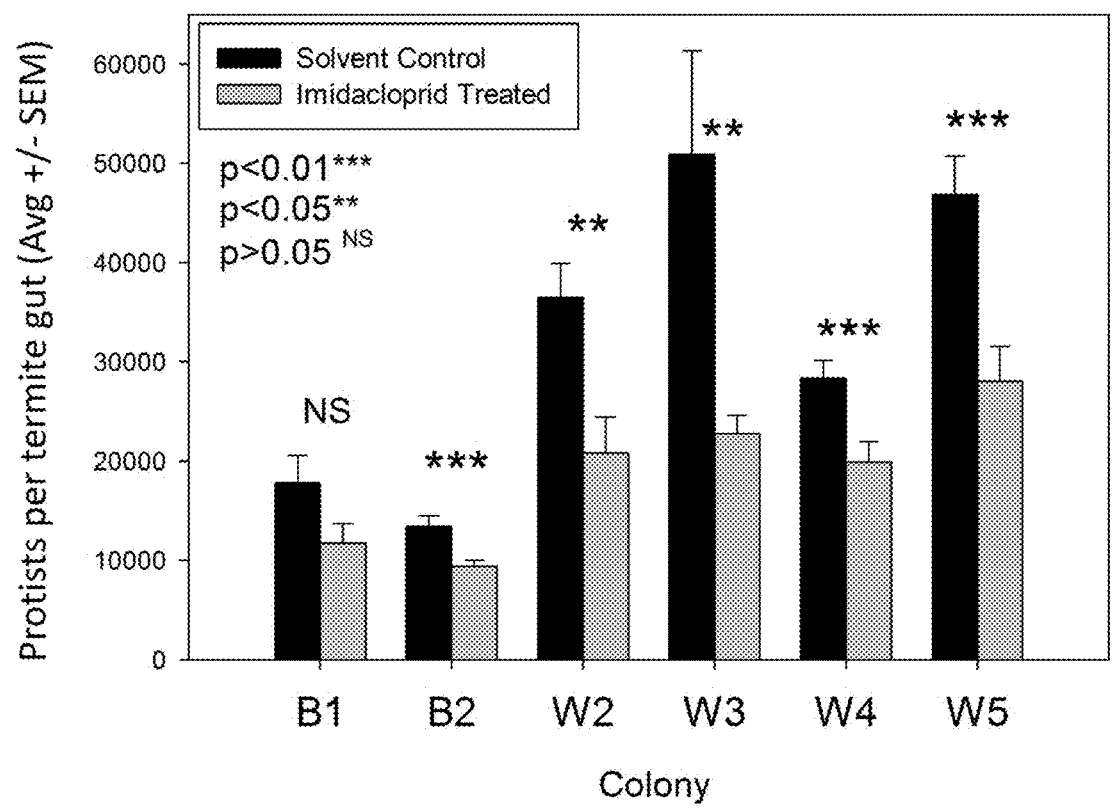
FIG. 1 illustrates a graphical representation of protist survival counts 2 days (48 hr) after imidacloprid treatments in five separate termite colonies (B1, B2, W2, W3, W4, and W5), with black bars representing DMSO solvent controls and gray bars representing imidacloprid treatments (paired bars with asterisks (*) are not different by Mann-Whitney U-tests at the different significance levels shown)

The disclosure of the present application provides molecular-level insight into the mechanisms of general pathogen defense and nicotinoid-pathogen synergy as applied to social insect colonies. Perhaps more specifically, the present disclosure provides novel treatment compositions and methods that exploit the newly discovered mechanistic underpinnings of nicotinoid-pathogen synergy including, without limitation, compromising social behaviors of the targeted insects and reducing protist symbiont populations present within the insects' hind gut.

For the purposes of promoting an understanding of the principles of the present disclosure, reference will now be made to several experimental studies and the results thereof illustrated in the figures and specific language will be used to describe the same. It will nevertheless be understood that no limitation of the scope of the present disclosure is intended by the description of these studies and/or results. Indeed, the materials and methods of the present disclosure may be embodied in many different forms and should not be construed as being limited by way of the language, results, and/or any embodiments expressly set forth herein.

Likewise, many modifications and other embodiments of the materials and methods set forth herein will come to mind to one of skill in the relevant arts having the benefit of the teachings presented herein. Therefore, it is to be understood that such alternatives, modifications, embodiments, and further applications of the principles of the present disclosure are intended to be included within the scope of the appended claims. Although specific terms may be employed, they are used in a generic and descriptive sense only and not for purposes of limitation. Furthermore, termites are the relevant model used in the studies described herein because they are eusocial insects that maintain complex microbial symbioses and they are purposely targeted by nicotinoid soil termiticides. However, it will be appreciated that the concepts and embodiments described herein are not limited in application to termites and may be applied to other categories of insects (e.g., any insects that form social insect colonies), as appropriate. Additionally, in the following description, well known methodologies and scientific techniques have not been described in detail so as to not unnecessarily obscure the present disclosure. Unless defined otherwise, all technical and scientific terms used herein have the same meaning as commonly understood by one of ordinary skill in the relevant arts.

As used in the present disclosure, "holobiont" means a fully functional multifaceted ecosystem composed of a host organism (i.e., termite) and its collective symbiota.

As used in the present disclosure, "dysbiosis" means a microbial imbalance or maladaption on or inside the body, such as in gut flora, which includes, but is not limited to, protists and bacteria.

As used herein, the phrase "reactive oxygen species" or "ROS" refers to chemically reactive chemical species that contain oxygen. Examples of ROS include, without limitation, peroxides, superoxide, hydroxyl radical, and singlet oxygen.

As used herein, the term "contig" refers to a set of overlapping DNA segments that, when taken together, represent a consensus region of DNA.

As used herein, "ABC" means ATP-binding cassette, "CAMKII" means $Ca^{2+}$/calmodulin dependent kinase II, "CDNB" means 1-chloro-2,4-dinitrobenzene, "CPM" means counts per million, "CT" means cycle threshold, "DNA Pol I" means DNA polymerase I, "GST" means glutathione S-transferase, "MAPK1" means mitogen-activated protein kinase 1, "OXPHOS" means oxidative phosphorylation, "PDA" means potato dextrose agar, "PPO" means prophenoloxidase, and "PUGC" means Purdue University genomic core.

As used herein, "upregulation" is the increase in expression (or quantity) from a baseline level of a cellular component, such as RNA or a protein, in response to a variable, and "downregulation" is the decrease in expression (or quantity synthesized) from a baseline level of a cellular component in response to a variable. Upregulation and downregulation are commonly measured in fold-change.

Symbioses throughout the animal kingdom are known to extend physiological and ecological capabilities to hosts. Insect-microbe associations are extremely common and often related to novel niche exploitation, fitness advantages, and even speciation events. These phenomena may include, without limitation, expansions in host diet, detoxification of insecticides and toxins, and increased defense against pathogens. Indeed, while the traditional, intuitive role for gut bacteria may be nutritional, gut microbiota can have profound impacts on their insect hosts.

Termites, in particular, have numerous significant symbiotic relationships. The protist-produced cellulases present in lower termites enable these insects to thrive on their nitrogen poor, recalcitrant wood diet. For decades termites were thought to rely entirely on symbiota for the digestion of their food. However, the identification of a highly-active, highly-expressed, endogenous β-1, 4-endoglucanase in a lower termite species shifted the perspective of this symbiosis from unidirectional to collaborative. As tools in molecular biology has advanced, more and more cellulytic enzymes have been identified from the symbiotic partners and hosts in all termite symbioses. Additionally, bacteria present in the lower termite gut are also known to play important roles in nitrogen cycling, hemicellulose and aromatic compound degradation, and acetate metabolism, all of which likely contribute to the maintenance of efficient cellulose digestion therein.

Along these lines, lower termite symbionts have been credited with contributing important anti-fungal enzymes that extend pathogen defense to their insect hosts and, in particular, beta-1, 3-glucanases from protist symbionts have been identified as a source of fungal deactivation in lower termites. However, while symbiotic actinobacteria provide anti-fungal functions within the nest walls of some subterranean termites and bacteria play important roles in termite and ant fungus farming mutualisms, there has been no mechanistic link identified between gut bacteria and pathogen defense in lower termites. This supports that lower termite-associated gut bacteria contribute to host physiology in more ways than solely nutrition and digestion.

The idea of "collaborative physiology" represents a joint effort by the members of the holobiont to accomplish basic physiological tasks such as digestion and immunity. Steps in assessing the extent and mechanisms of these collaborations require approaches that encompass the entire micro-ecosystem that is the termite gut. Assessing the holobiont allows for a more complete picture of functional capacity of individual members of the consortium, but also sheds light on interspecific collaborations.

As described in detail below, various methods were used to explore the contributions and potential collaborations of the termite host and its hind-gut consortium. Through these inquiries, novel insights into the mechanisms of nicotinoid-pathogen synergy and bacterial-derived anti-fungal defense in termites were identified and, based on such findings, novel compositions, molecular targets, and methods for social insect colony treatment are provided. Furthermore, the present disclosure provides an abundance of transcripts that encode bacterial nutrient and metabolite transporters, amino acid synthetic enzymes, and carbohydrate metabolism, as well as identifies differentially expressed transcripts between fungal infected and uninfected termites. Perhaps more specifically, the present disclosure identifies at least one novel amidohydrolase mechanism of symbiont-mediated defense and in at least one exemplary embodiment, identifies several candidate genes—including, but not limited to, amidohydrolase 2, peroxiredoxin, glutathione s-transferase, ferritin, heat shock protein, cytochrome b-c1 subunits 79, and 10, cytochrome c, cytochrome c oxidase subunits 6B, 6C, and 7C, NADH dehydrogenase 1 alpha subunit, 3'-5' exonuclease, 3'-5' exonuclease-DNA polymerase I, calcium-calmodulin dependent kinase II CAMKII, and mitogen-activated protein kinase 1 MAPKI—the expression of which can be manipulated to undermine termites' natural defense mechanisms present within the hind-gut. SEQ ID Nos.: 3-19 provide sequence information to allow for contigs of the above-described genes (or portions thereof) to be obtained readily by straightforward application of routine techniques.

To promote ease of understanding, the results and novel implications of the experimental studies on which this disclosure is based will first be discussed along with the novel materials and methods derived therefrom, followed by detailed descriptions of the underlying experimental studies themselves.

Nicotinoid-Pathogen Synergy in the Termite Gut

Nicotinoids (such as imidacloprid) disrupt the insect nervous system by agonizing nicotinic acetylcholine receptors, which leads to excessive neuroexcitation and, eventually, irreversible neurological disruption. As a soil termiticide, imidacloprid has unique physical properties that allow it to be acquired and moved among individual termites via trophallaxis and contact. In this manner, imidacloprid can eventually affect colonies at substantial distances away from treated structures.

Nicotinoids taken up by termites are rapidly metabolized to a mix of active and inactive metabolites, most notably, glucuronic acid conjugates. Their formation is noteworthy because of the availability of both glucose and glucuronic acid in termite food (i.e. cellulose and hemicellulose) and the potential for such conjugate formation to be mediated by hindgut symbiont action. Glucuronic acid conjugates are also highly water-soluble and susceptible to transfer by trophallaxis and allogrooming. Imidacloprid toxicokinetics, transfer, and its potential for neurological disruption were all considered with respect to the key findings disclosed herein.

Previous studies in lower termites have identified unexpected synergies between nicotinoid insecticides and fungal entomopathogens. To identify and better understand the molecular mechanisms of nicotinoid-pathogen synergy in the lower termite *Reticulitermes flavipes* and as described in additional detail below, termite colonies were treated with the nicotinoid imidacloprid in combination with fungal and bacterial entomopathogens to investigate nutritional, hormonal, and social impacts on gut metatranscriptome composition. Gut microbiota composition was also characterized, as well as its recalcitrance to dietary changes. Perhaps more specifically, the studies comprised exposing five groups of termites to differing treatments—namely, single challenges with sublethal doses of fungi (*Metharizium anisopliae*) (F), bacteria (*Serratia marcescens*) (B), or imidacloprid (I), and dual challenges with fungi+imidacloprid (F+I) or bacteria+imidacloprid (B+I). The various groups were then observed and tested and the results were recorded and compared. Generally, the experimental studies comprised exposing five groups of termites to differing treatments—namely, single challenges with sublethal doses of fungi (*Metharizium anisopliae*) (F), bacteria (*Serratia marcescens*) (B), or imidacloprid (I), and dual challenges with fungi+imidacloprid (F+I) or bacteria+imidacloprid (B+I).

The various groups were then observed and tested and the results were recorded and compared.

In sum, the disclosure hereof identifies multiple modes of action through which insecticide-pathogen synergy occurs, as well as novel routes through which nicotinoid insecticides and pathogens interact thus causing the resultant deleterious impacts on social insect colonies. Namely, protist dysbiosis and compromised social behavior have been identified as two dominant factors underlying nicotinoid-pathogen synergy in termites, rather than suppression of stereotypical immune defense mechanisms as conventionally thought. The greater impacts observed in connection with the fungal pathogen as compared to the bacterial pathogen suggest that the rich bacterial symbiont community in the R. flavipes' gut (>5000 species-level phylotypes) exists in an ecological balance that effectively excludes exogenous bacterial pathogens.

Additionally, numerous gene targets (both host and symbiont) are identified that are associated with nicotinoid-pathogen synergy and/or innate defense mechanism present within insects and termites, specifically. Applications of the present disclosure manipulate the identified gene targets of the present disclosure (through either up- or down-regulation) to promote or suppress the same. These findings significantly advance conventional understanding of antimicrobial defenses in this important eusocial insect group, as well as providing novel insights into how nicotinoids can be used to exert deleterious effects on social insect colonies by, at least in part, dismantling such insects' natural defenses. Furthermore, two enzymes in the symbiont glycosyl hydrolase family 7 (GHF7)—namely, GHF7-5 and GHF7-6—are identified as having antifungal activity and a related role in termites' antifungal defense mechanisms. This is particularly noteworthy in light of their significant down-regulation identified herein following a F+I treatment (1000-fold) and the resulting effect on termite mortality rates.

Additionally, because the data supports that these newly identified protist symbiont enzymes play a central role in protecting termites from fungal entomopathogens, novel compositions containing recombinant forms of these enzymes can provide an effective and protein-based enzymatic (i.e. more "organic") approach to fighting fungal infections in both plants and animals. For example, in at least one exemplary embodiment, such composition may comprise a recombinant form of an enzyme in the symbiont GHF7 family that is engineered to cure or attenuate fungal infections by degrading the cell walls of invading fungal pathogens.

Effects at the Organismal and Sub-Organismal Levels

Notably, the addition of sub-lethal concentrations of imidacloprid in all treatments suppressed many of the termites' social behaviors that protect these soil-dwelling insects from disease (grooming, trophallaxis, and tunnel formation). The impacts of sub-lethal imidacloprid concentrations (I, B+I, and F+I) on termite tunneling and grooming behaviors were observed at least within 24 hours post-exposure. In fungi treatments (F and F+I), grooming of colony conspecifics resulted in the near-complete removal of conidiospores attached to the cuticle within 24 hours; the ingestion of these conidiospores by groomers places the fungal propagules in contact with a gut microbiota that is highly antagonistic/suppressive to potential pathogens. By way of example, tunnel formation by termites is highly antagonistic to microbial growth—termites coat their tunnels with gut microflora and metabolites that presumably suppress or outcompete pathogens for available resources. As such, a reduction in termite tunneling behavior can have a negative effect on overall termite health as it results in a higher degree of exposure to harmful pathogens.

In addition to social behaviors, the termites were also assessed with respect to their innate immune response following imidacloprid treatment. Recently, nicotinoids have been reported to suppress the innate immune response in several insects. For example, it has been reported in honey bees that the neonicotinoid clothianidin upregulates a leucine-rich peptide that is a negative modulator of the nuclear factor-$k\beta$ signaling. The result of this immunosuppression is increased replication of the deformed wing virus in covertly infected honeybees. The downregulation of nuclear factor-$k\beta$ signaling may also influence gut microbiota homeostasis as observed in Drosophila and, therefore, disrupt nutrient digestion and nutrient assimilation. However, per the results of the examinations described herein, while imidacloprid treatment upregulated a transcript that was annotated as a host cell membrane leucine-rich peptide in termites, it failed to substantially alter expression of other genes stereotypically associated with the innate immune response (see Table 2 below). This finding aligns with the previous finding in R. flavipes that exposure to sublethal doses of imidacloprid failed to alter its phagocytic response to non-self.

Figure 2A:
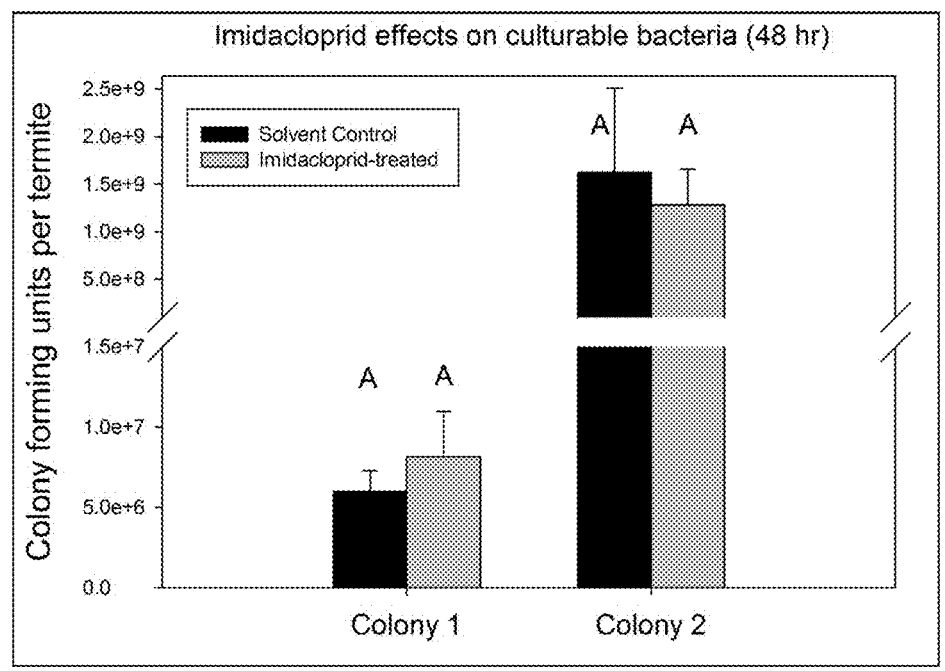
FIGS. 2A and 2B show the results of two assessments of imidacloprid impacts on gut bacteria after 48 hours, with FIG. 2A illustrating the results of aerobic culturing and FIG. 2B illustrating 16S real-time quantitative PCR results to estimate relative bacterial DNA abundance; two colonies were used for both assessment methods, one in the lab for >2 years (colony 1) and one in the lab for <2 months (colony 2); bars with same letters for each colony within graphs are not significantly different by Mann-Whitney U-tests ($p>0.05$)

An additional, unexpected consequence of imidacloprid treatment in termites was a decrease in hindgut protist symbiont populations (see FIG. 1). In general, termites have symbiont-rich guts that house a diverse mix of protists and bacteria. While there are no prior reports of imidacloprid being active against eukaryotic protists, nicotine-like substances and their analogues are known to have antibacterial activity in other systems. Here, notably, assays testing imidacloprid-impregnated paper discs at concentrations of 1-1000-fold higher than used in the disclosed feeding assays failed to suppress the growth of the aerobic, culturable bacterial community from the R. flavipes digestive tract (see FIG. 2A). Indeed, investigation of total bacterial DNA abundance using 16S PCR signals as a proxy did not detect any impact on the hindgut microbial dynamics in imidacloprid-treated individuals (see FIG. 2B).

Accordingly, it appears that sub-lethal concentrations of imidacloprid indirectly alter bacteria-host associations through a reduction in feeding or trophallaxis, as well as by modifying the suitability of the hindgut as a protozoan microhabitat. The protists that remained in the gut following imidacloprid treatment, although significantly fewer in number, were observed to be alive. The reduction in protist numbers is reflected in the selective downregulation of symbiont genes in all treatments that included imidacloprid. For example, exposure to imidacloprid (I) alone upregulated a majority of host transcripts (177 host vs. 19 symbiont), but downregulated a majority of protist symbiont transcripts (205 symbiont vs. 8 host). Also, protist GHF7 cellulases were substantially downregulated in the F+I treatment, supporting important digestion-immunity tradeoffs (discussed in additional detail below).

Immune Gene Expression

Cuticular exposure or ingestion of fungi (F) or bacteria (B) did not infect or cause a lethal mycosis or sepsis in treated R. flavipes. Unlike the I treatment, exposure to fungal and bacterial entomopathogens alone did not alter the termite eusocial behaviors that underlie pathogen resistance. In fact, the presence of the fungus on the cuticle and then in the gut (via grooming) induced the lowest number of transcript changes seen in the study. Cuticular exposure to a high concentration of conidiospores upregulated significantly more host (56) than symbiont transcripts (12), but downregulated low numbers of both symbiont (8) and host (6)

transcripts. Accordingly, ingestion of fungal spores via grooming elicited only minor changes in gut symbiont populations.

Overall, both treatments resulted in minor fold changes in both upregulated (69) and downregulated (14) host and symbiont transcripts. Ingestion of bacteria stimulated more transcripts to be altered at a greater fold change than the F treatment, and like the F treatment, more transcripts were upregulated in the B treatment (142 host, 13 symbiont) than were downregulated (6 host, 34 symbiont).

As such, elicitors associated with the ingested bacteria, although capable of upregulating host transcripts, are not antagonistic to gut protists that co-inhabit the hindgut with a complex high-density bacterial community. Microarrays included~40 antimicrobial host genes that were annotated as components of the phenoloxidase cascade, various non-self recognition proteins (for example, lectins, GNBPs, and chitin-, LPS- and glycan-binding peptides), cationic peptides, programmed cell death proteins, and enzymes (serpins). Treating termites orally with bacterial cells or topically with fungal conidiospores did not result in a significant alteration in the transcription of these defense-related genes. At least with respect to the bacterial challenges, this lack of detectable upregulation of gut-associated innate defense genes was unexpected. Indeed, it is well-known that *Serratia marcescens* is an opportunistic insect pathogen and, like other Gram-negative opportunistic bacteria, is conventionally recognized to elicit insect gut innate defenses.

As observed previously, the consequence of exposure to sublethal imidacloprid concentrations is the rapid onset and complete mycosis by normally ineffective entomopathogenic fungi. Termites exposed to the F+I treatment at two days were presumed to contain replicating vegetative *M. anisopliae* cells at the time of sampling, as more than 70% of the insects alive at 2 days (i.e. the point of RNA extraction for gene expression studies) succumbed to mycosis by 3 days post-challenge. The combination of B+I also led to increased (but not synergistic) levels of sepsis. Unlike the F or B treatments, the F+I treatment (which resulted in lethal mycosis) upregulated several antimicrobial host genes, including lysozyme, PRPs, termicin, and transferrins. These findings support that imidacloprid, rather than suppressing physiological immune mechanisms as conventionally thought, instead blocks immune-related behaviors and allows the fungus to invade the host. The ensuing pathogen ingress then elicits the termite's innate defense response, which is incapable of preventing a lethal mycosis.

Similarly, the B+I treatment resulted in 50% lethal sepsis and also upregulated two symbiont heat-shock proteins. However, like the B treatment, the B+I treatment caused no significant alterations in termite gut antimicrobial transcripts. Conversely, in the termite *Coptotermes formosanus*, subtracted mRNA libraries from whole insects revealed that microbial challenge (topical exposure) upregulated a cascade of immune-associated genes. Another study in *C. formosanus* comparing candidate gene expression responses to xenobiotic and bacterial challenges similarly identified an induction of immune and xenobiotic response genes.

While the inability of sepsis to induce gut innate defenses as seen here may be attributed to a number of study-related causes (such as, for example, a lack of inducible genes present on the microarray or improper timing in the sampling of gut mRNA), it is likely that they are due to these social insects having weak innate defenses. Here, the arrayed target genes were all derived from ESTs generated from gut mRNA of healthy workers. The termites sampled in the present study were orally challenged with a single bacterial strain and only gut mRNAs (not fat body) were sampled at a single interval. Possibly, using different bacteria, cell concentrations, or sampling different tissues at additional time intervals would have shown upregulation of the antimicrobial genes. However, previous research on *R. flavipes* has shown that injection of LPS, a universal elicitor of insect innate defense pathways, also fails to induce the synthesis of cationic peptides, thus supporting the idea that this species possesses a weak innate defense system. Accordingly, the present disclosure supports that *R. flavipes* relies on a combination of hygienic behaviors and gut microbial ecology to create a microclimate that is antagonistic to potential entomopathogens.

Expression of Non-Immune Genes

In terms of non-immune-related genes, many carbohydrate-active genes were differentially expressed among treatments. Most notably, the symbiont GHF7 cellulases were all significantly downregulated in the F+I treatment, including one isoform that was downregulated over 1000×. Conversely, several GHF7s that downregulated in the F+I treatment were upregulated with the less-lethal B+I treatment. None of the GHF7s identified herein were responsive in preceding diet or hormonal microarray studies. Additionally, several chemosensory-related genes from the takeout family were upregulated with various treatments, particularly F+I. These genes are relevant to chemical communication that likely directs eusocial disease management.

Two additional inter-related categories are detoxification and P450 genes. Key responsive detoxification genes included ABC transporters, catalase, epoxide hydrolase, and P450s. In particular, two ABC transporters were downregulated in F+I and upregulated in B+I treatments. Nine P450s from the CYP4, 6, 9, 15, and 304 families were all upregulated in response to various treatments, but mainly to F+I. Similar CYP15 responses were also documented in *C. formosanus* workers in response to bacterial and xenobiotic challenges. Also, several genes occurring in the juvenile hormone (JH)-responsive category were initially identified in a prior study specifically investigating JH impacts on caste differentiation and gut gene expression: 50 kDa Midgut protein, insulin receptor, nli phosphatase, tyramine beta hydroxylase, and arylsulfatase. Of these, the 50 kDa gene was the most JH-responsive, but it has no GO terms and few homologues in other insects. Most of these genes were upregulated in the various treatments, supporting parallels between JH-induced morphogenesis and gut restructuring as a mechanism of pathogen defense.

Two neuropeptide-encoding genes also were most highly upregulated in the F+I treatment: allatostatin and neuropeptide F. Allatostatins regulate JH biosynthesis and neuropeptide F controls gut peristalsis; both processes potentially mediate pathogen defense. Three transcription factors were all upregulated with I, F+I and/or B+I treatments; one (EF Hand family protein) having been previously associated with dietary phenolics and potentially phenolic-mediated melanization processes. Lastly, in the "other" category, a protist cysteine synthase, a gene that was significantly downregulated in the I and F+I treatments, was previously upregulated by cellulose feeding (the substrate used in the current study).

The results of the examinations of select candidate genes described herein support the existence of digestion-immunity tradeoffs. Furthermore, gut remodeling, gut physiology, and social behavior are hallmarks and likely mechanisms of nicotinoid-pathogen synergy. Particularly important driving factors appear to be the significant degree of symbiosis occurring in the *R. flavipes* gut (i.e.

11 protists and >5000 bacterial OTUs), the susceptibility of protists to imidacloprid (see FIG. 7), and the suppression of the host immune response in favor of bacterial symbiont populations and to preserve an appropriate ecological balance in the hindgut.

In at least one exemplary embodiment, these findings can be exploited to increase termite susceptibility to pathogens in furtherance of termite population control. While conventional compositions and methods are directed towards non-specific chemical insecticides that attempt to brute force their way through termite defenses, providing compositions and methods targeting the specific genes and proteins identified herein (see Table 2 below) enables a targeted approach to dismantling termite defenses outright. Perhaps more specifically, in at least one exemplary embodiment or a method for controlling a population of termites, a composition may be administered that suppresses the expression of the targeted genes, thereby increasing the termites' susceptibility to pathogens. In at least one example, such a composition may comprise double-stranded RNAs for silencing expression of specific defense genes (in the host termite, its gut symbiota, or both). Additionally, antibacterial and/or anti-protozoal drugs designed to reduce symbiont populations may also be included. Not only is such an exemplary composition more efficient than those conventionally employed, but the novel compositions and methods hereof are also significantly more biorational and environmentally friendly than the chemical insecticides currently used.

GHF7 Proteins as Potential Symbiont-Derived, Anti Fungal Enzymes

Generally, β-1, 3-glucanases are enzymes known for breaking down β-1, 3-glucans, which are the main component of fungal cell walls. Lower termites have two β-1, 3-glucanases in their body and multiple additional, symbiont-derived, β-1, 3-glucanases in their gut. It is known that the symbiont-derived β-1, 3-glucanase activity is a means of anti-fungal defense in lower termites, which may translate into lower susceptibility to mycosis for their termite hosts. This, combined with the novel finding hereof that the combination treatment of F+I affects termite survival and results in the down-regulation of GHF7-5 1000-fold, led to an inquiry into the role of two protist GHF7s in anti-fungal defense—GHF7-5 and GHF7-6.

These two particular enzymes have conventionally been characterized as having weak β-1, 4-glucanase activity and, as such, relegated as being of little importance for lignocellulose digestion. To test the efficacy of recombinant GHF7-5 and GHF7-6 as antifungal enzymes (the nucleotide sequences of which are set forth below with respect to SEQ ID No. 1 and SEQ ID No. 2, respectively), these enzymes were evaluated against a variety of substrates containing β-1, 3 and β-1, 6 glycosidic bonds, which are present in fungal cells walls. Perhaps more specifically, GHF7-5 and GHF7-6 activity was tested on a variety of substrates with varying incubation times and buffers. These recombinant enzymes were also tested for activity against four nitrophenol model substrates and against a laminarin assay. Additionally, the capacity of these enzymes with respect to their ability to impede fungal development and, in turn, confer fungal protection to their host termites was evaluated, as well as the effect of pre-treatment of fungal conidia with GHF7s on subsequent termite survival. All tests utilized pure recombinant enzymes.

Figure 8:
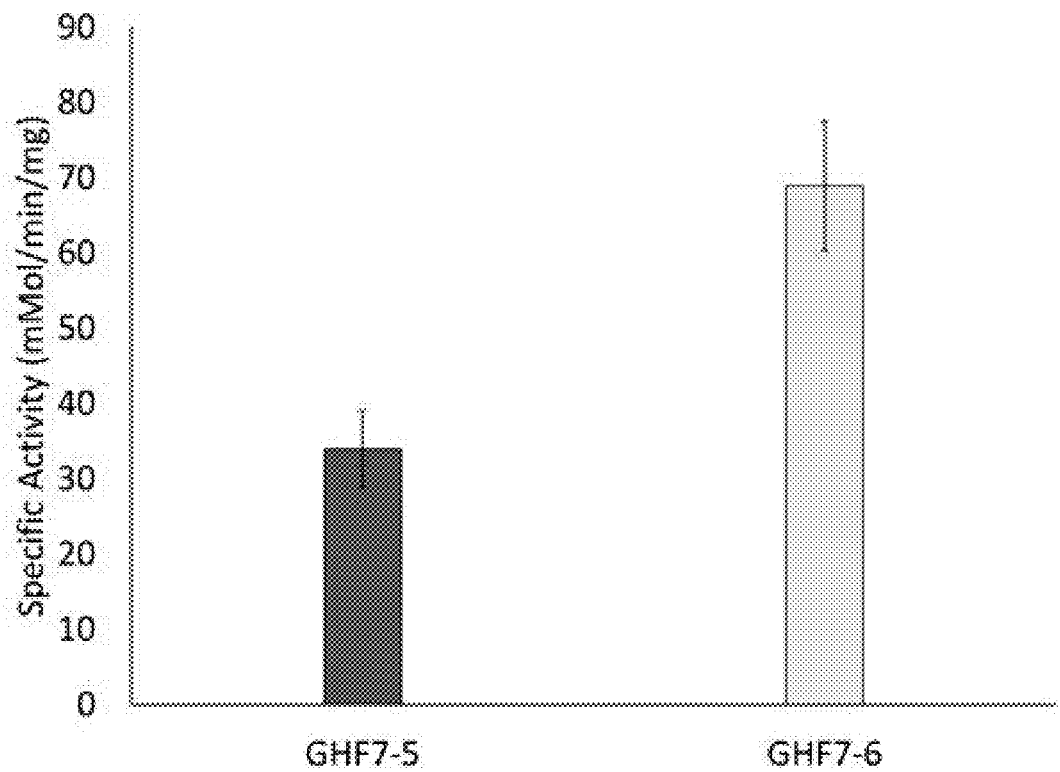
FIG. 8 is a bar graph representative of GHF7-5 and GHF7-6 activity on 0.75% laminarin producing reducing sugars detected by DNSA, with the activity of GHF7-5 represented by the dark bar and the activity of GHF7-6 represented by the light bar (error bars represent standard error across six technical replicates)
Figure 9:
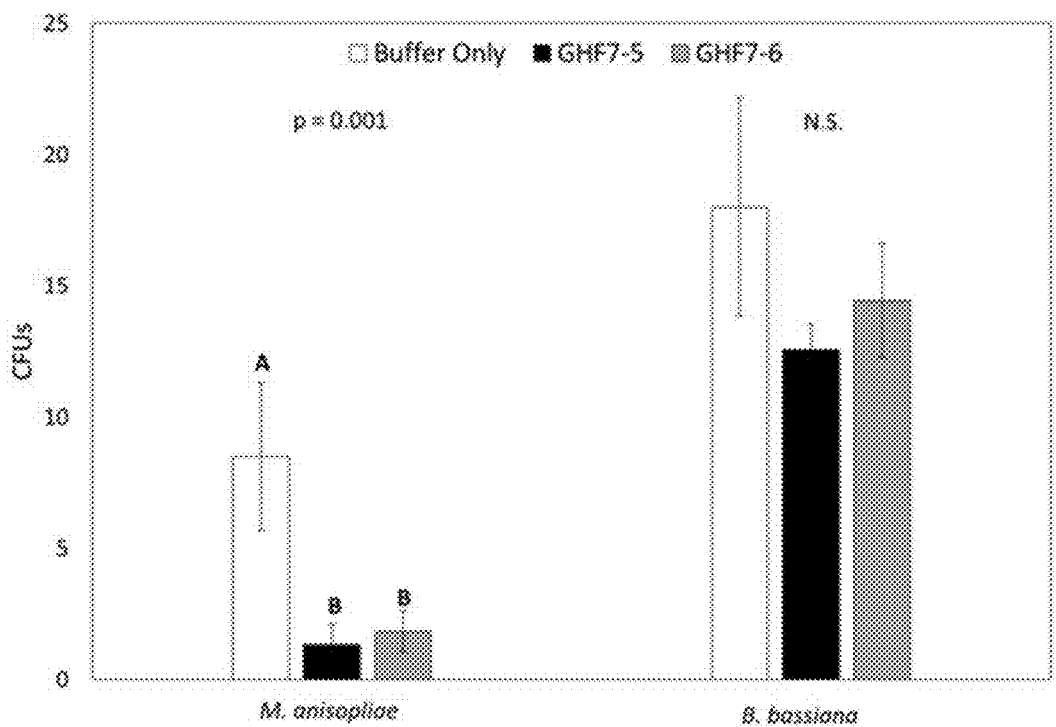
FIG. 9 is a bar graph illustrating fungal CFUs after pre-incubation with GHF7s with colony forming units counted 96-hours post-incubation with potential anti-fungal enzymes; white bars representative of buffer only controls, black bars representative of GHF7-5 treated conidia, and gray bars representative of GHF7-6 treated conidia (error bars represent SEM and bars with the same letter are not statistically different ($\alpha=0.05$))

While a number of assay conditions and substrates were tested, GHF7-5 and GHF7-6 only displayed strong activity with the substrate laminarin with sodium acetate buffer (see FIG. 8). This finding is notable due to the substrate laminarin's homology to fungal cell walls (i.e. the inclusion of β-1, 3 and β-1, 6 glucan linkages); indeed, laminarin has been used as an analog to trigger immune responses in vivo.

Figures 10, 11:
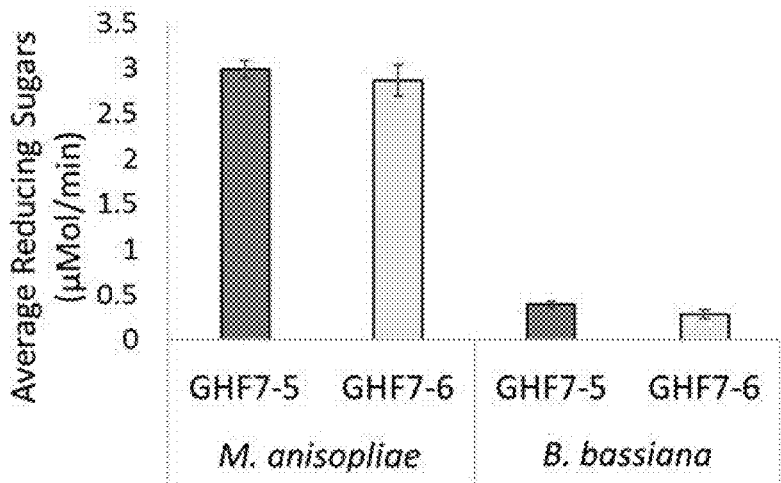
FIG. 10 shows a bar graph illustrating the amount of reducing sugars detected in in vitro assays, with average reducing sugars released during in vitro assays detected with DNSA.
FIG. 11 shows a multiple sequence alignment including termite protist and fungal GHF7 enzymes, specifically: GHF7-3, GHF7-5 and GHF7-6 from *R. flavipes*, *Holomastigotoides mirable* (Genbank: AB071012), *Trichoderma reesei* (Genbank: M15665 and P62694) and *Pseudotrichonympha grassii* (Genbank: AB071868) from *C. formosanus*.
Figure 12:
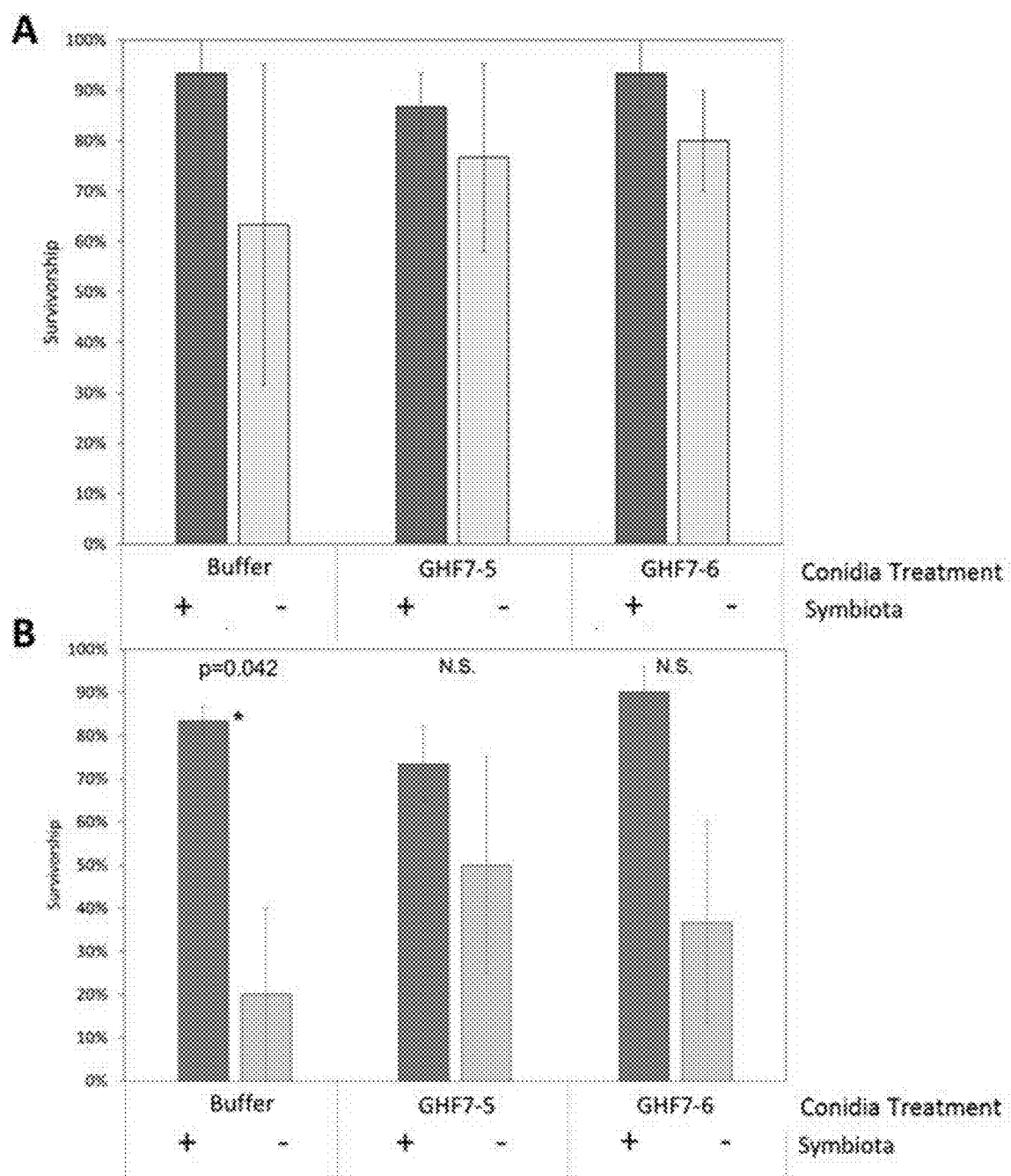
FIG. 12 illustrates two graphs representative of study results relating to termite survival following challenge with fungal conidia; portion [A] of FIG. 12 showing survivorship results of termite workers following treatment with *M. anisopliae* and portion [B] of FIG. 12 showing survivorship results of termite workers following treatment with *B. bassiana*, each subject to subsequent exposure to either buffer (control), GHF7-5, or GHF7-6, with dark bars representing termite workers with intact gut fauna and light bars representing termite workers pre-treated with kanamycin (error bars represent SEM and each paired treatment compared using a t-test to determine if conidial pre-treatment would rescue symbiont depletion ($\alpha=0.05$))

With respect to testing the two protist glycosyl hydrolases for antifungal activity, supernatant from in vitro assays of all enzyme-fungus combinations showed detectable levels of reducing sugars present therein that were absent from buffer controls (see FIG. 10). The presence of reducing sugars indicates the breakdown of polysaccharides in GHF-positive in vitro assays—namely, that reducing sugars are being liberated from fungal conidia. The cell walls of fungi have an anionic surface and a reliance on β-1, 3- and β-1, 4-linked polysaccharides as fibrous components. Branched β-1, 6 glucan is also present therein and links together the other components of the cellular wall (i.e. β-1, 3 and β-1, 6 glucans are latticed atop of a chitinous layer). Accordingly, the presence of reducing sugars in the test assays, and the complete absence of reducing sugars detectable in the no-enzyme control assays (<0.000 mMol total at endpoint as shown in FIG. 10), supports that GHF7-5 and 7-6 are responsible for the breakdown of the polysaccharides in the fungi cellular wall and, thus, are consistent with antifungal enzymes. While there was a marked difference in the abundance of reducing sugars present between species of fungi, this can likely be attributed to the vast differences in cell wall glucan composition across fungi species.

GHF7-5 and 7-6 also had varying impacts on the viability of conidia. Fungal conidia from both tested fungi exhibited some reduction in germination following incubation; however, as with the reducing sugars assay, *M. anisopliae* was significantly more inhibited by GH7 pre-treatment than *B. bassiana* (see FIG. 10). Another seemingly relevant feature of GHF7-5 and 7-6 is that, as shown in FIG. 11, their translated protein sequences have tunnel forming loops present that are lacking in closely-related protist GHF7 enzymes with greater activity against dietary cellulosic substrates. FIG. 11 shows a multiple alignment of termite protist and fungal GHF7 enzymes. Underlining denotes secretory signal peptides in the three *R. flavipes* proteins. Boxes enclose tunnel forming loops absent in GHF7 cellulases and present at analogous positions in GHF7s having β-1, 3 glucanase activity. Numbering indicates the likely catalytic motif consisting of a catalytic nucleophile (1), proton donor (2), secondary nucleophile (3), and substrate-binding tryptophan residues (4). The sequences aligned in FIG. 11 are as follows: GHF7-3, GHF7-5 and GHF7-6 from *R. flavipes*, *Holomastigotoides minable* (Genbank: AB071012), *Trichoderma reesei* (Genbank: M15665 and P62694) and *Pseudotrichonympha grassii* (Genbank: AB071868) from *C. formosanus*.

The practical application of these novel findings is significant. Indeed, in light of it being determined that protist symbiont enzymes GHF7-5 and 7-6 play a central role in protecting termites from fungal entomopathogens, recombinant forms of these enzymes can be utilized in connection with novel pharmaceutical compositions for the treatment of fungal infections. In at least one exemplary embodiment of the present disclosure, novel compositions comprising recombinant GHF7-5 and/or 7-6 and methods of administering the same may provide protein-based enzymatic treatments rather than the less organic approach provided by conventional drugs. Additionally or alternatively, the GHF7-5 and/or 7-6 enzymes hereof could be administered for antifungal purposes as recombinant proteins produced ex vivo, within recombinant microbes applied in vivo, within secretions present in recombinant microbe-incubation broths, as produced by crop plants or trees in vivo, and/or in any other manner as may be currently known or hereinafter determined that may prove beneficial in the treatment or prevention of fungal infections in plants, insects, and/or animals.

Nicotinoid-Pathogen Synergy Methods, Materials, and Results

To facilitate a complete understanding of the present disclosure, the underlying studies utilized in support of the novel concepts presented herein will now be described in detail. Detailed results of such studies are also provided below.

Termites

For the studies described herein, worker termites were used exclusively. Five established laboratory colonies isolated from field sites near Gainesville, Fla., USA were used: B1 #1(1 year in the lab); B2 (3 months in the lab); K2 (3 years in the lab); K5 (2 years in the lab); and K9 (3 months in the lab). All colonies were verified as R. flavipes by mitochondrial 16S rRNA sequencing. Colonies were maintained in darkness in sealed plastic boxes with wet pine wood shims and brown paper towel, within an environmental chamber kept at 22° C. and 60% RH. Preceding studies on three colonies (B2, K5 and K9) indicated significantly variable bacterial microbiota compositions between the colonies that are recalcitrant to change under different 7-day dietary regimes. On the contrary, the host and protist gut gene expression profiles of all five colonies responded significantly to dietary, hormonal, and social treatments.

Pathogen Bioassays

Separate assays were performed for microarray analysis and for assessing survivorship. For immune challenges, concentrations of fungal spores, bacterial cells, and imidacloprid were selected based on published findings and on results from preliminary screening assays. For fungal treatments, spores of Metharizium anisopliae (isolate Ma1630) were collected from in vitro cultures 10-12 days after inoculation onto McCoy's agar, suspended in 0.5% of aqueous Tween 20, counted in a hemacytometer, and diluted with water to a final concentration of $10^5$ spores/ml. Each replicate of 20 termites was placed in a steel mesh specimen basket (16 mm outer diameter, 8 mm high) and submerged in 5 ml of spore suspension for 20s. After removal of excess liquid with tissue paper, termites were gently tapped into the Petri dish.

Viability of fungal spores was around ≥94% and determined by spreading diluted aliquots of each suspension onto McCoy's agar and recording germination after 24 hours. For bacterial challenge, Serratia marcescens cells (isolate "New Zealand May 18") were harvested from nutrient broth cultures during exponential growth phase and centrifuged at 5,900×g for 10 min at 4° C. Broth was removed, cells were suspended in sterilized saline (0.85% NaCl), and cell concentration estimated spectrophotometrically (OD600) and adjusted to $6.5 \times 10^9$ cells/ml before 150 µl was applied to filter paper discs (final dosage=$2.35 \times 10^8$ cells/cm$^2$), which served as food substrate. Viability of bacterial cells was confirmed by spotting diluted aliquots of cell suspensions onto nutrient agar and counting colony-forming units (CFUs) after 24 h.

For insecticide treatments, filter paper discs were treated with a 0.0001% aqueous solution of imidacloprid (97.5% purity, Bayer, Pittsburgh, Pa.; initially dissolved at 1% w/v in dimethyl sulfoxide, DMSO) and allowed to air-dry before use. Termites in dual treatments were exposed to imidacloprid and either on M. anisopliae or S. marcescens. Discs for control treatments were pretreated with 0.0001% aqueous DMSO and moistened with 150 µl saline.

Protist and Bacterial Counts

To determine if imidacloprid indirectly or directly impacted protist and bacteria gut symbiont populations, post-hoc tests were performed using multiple independent termite colonies. Protist counts were made using five laboratory colonies as previously described. Bacterial CFU counts were done via aerobic culturing using two laboratory colonies; one that had been in the lab for >2 years ("colony 1") and one collected from the field 1 month earlier ("colony 2"). Groups of termites from two colonies were exposed to imidacloprid or to solvent control treatments for 48 hours. Whole guts dissected from individual termites were sonicated in 250 µL of PBS, serially diluted, and spotted (2 µL) onto nutrient agar plates.

After incubation at 26° C. for 24 hours, plates were examined—spots producing 3-10 CFUs were used to estimate the total number of aerobic culturable bacteria per termite. In addition, dilutions of gut homogenates were directly plated onto nutrient agar; discs loaded with serial dilutions of imidacloprid were added to these plates to examine its direct impact on the culturable bacteria. Quantitative polymerase chain reaction (qPCR) was performed to determine bacterial abundance in each sample used for CFU counts (i.e. colonies 1 and 2) with and without imidacloprid treatment.

DNA was isolated from termite whole guts following control or imidacloprid treatments in bioassays using the Epicentre Yeast DNA extraction kit, including RNase treatment (Madison, Wis.). Following isolation, DNA samples were subjected to phenol-chloroform cleanup and concentrated using sodium acetate-ethanol precipitation. qPCR reactions were performed in triplicate with SensiFast SYBR No ROX kit (Bioline; Taunton, Mass.), 50 ng of sample DNA, nuclease-free water, and degenerate 16S rDNA primers. Primers amplified a 291 bp fragment containing the V4 hypervariable region of the 16S rRNA gene. Host DNA was quantified using primers specific to an apparent single-copy host gene, Actin 5C-1. Data were normalized to Actin 5C-1 to determine the relative abundance of 16S amplicons in the control and imidacloprid-treated DNA preparations.

Gut Extraction and RNA Isolation

After two days, a subset of ten termites was removed from each of the replicate colony treatments (20 total samples), cold-immobilized, surface-sterilized by a serial rinse in 0.3% sodium hypochlorite (1×) and sterilized water (2×), and dissected on Parafilm to collect digestive tracts, including salivary glands. Digestive tracts were transferred into RLA Lysis Buffer (Promega, Fitchburg, Wis., USA) and stored at −70° C. until RNA isolation. RNA extraction and cDNA synthesis was performed.

Microarrays and Hybridization Protocols

Experiments were designed after MIAME guidelines. A type II microarray design was used with a common-reference strategy. The common reference consisted of a normalized blend of all RNA samples included in the experiment. This common reference was co-hybridized against each replicate sample on single microarrays. Dye swaps were performed between replicate samples and references to check for potential dye impacts on spot intensity. Twenty-five total microarray hybridizations were performed, which consisted of five colonies each treated with solvent controls (SC) or sublethal doses of fungi (Metharizium anisopliae) (F), bacteria (Serratia marcescens) (B) or imidacloprid (I), and dual challenges with fungi or bacteria+imidacloprid (F+I or B+I). cDNA microarrays containing a mix of host and protist symbiont oligonucleotides were then used to simultaneously assess termite and protist gene expression.

Figure 4:
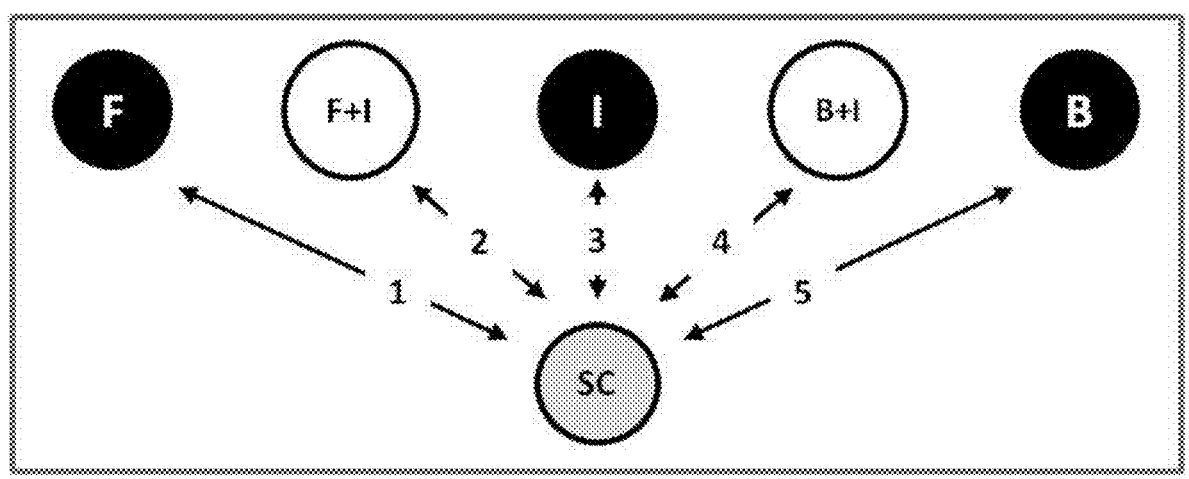
FIG. 4 shows a graphical summary of at least one embodiment of the microarray treatment utilized in the present disclosure with F (fungi), I (imidacloprid), B (bacteria), F+I (fungus+imidacloprid), B+I (bacteria+imidacloprid), and SC (solvent control) treatments.

Specifically, such microarrays contained a mix of ~14,500 cDNA oligonucleotides representing 10,500 host gut and protist/symbiont genes, including stereotypical immune response genes, thereby providing simultaneous assessments of host and protist gene expression. Reported analyses consisted of five pairwise comparisons to a common control as denoted by the numbers 1-5 in FIG. 4. More specific microarray data are provided in S15-S20 Tables of Sen et al. 2015, PLoS ONE 10(4): e0123391 (the "Sen Article"), which is hereby incorporated by reference herein in its entirety. These data are shown by array position for each treatment, normalized to mixed reference hybridizations, and include negative and positive controls. Genbank accession numbers for sequences at each microarray position are provided in S21-S23 Tables of the Sen Article.

Microarray Statistical Analyses

The Matlab statistics toolbox was used for statistical analysis of the intensity data of the 25 hybridizations from five different treatments (SC, F, B, I, F+I or B+I). Before comparative analysis, the individual signal intensity values obtained from the microarray probes were log-transformed (using 2 as the base) and normalized among all individual samples included in the study. Normalization was accomplished by scaling the individual log-transformed signal intensities so that each dataset had comparable lower, median, and upper quartile values. After the data were normalized, t-tests were used to make probe-by-probe comparisons among treatments. In each comparison, a p-value and fold change were computed for all microarray loci. In addition to p-values, q-values were computed. While the p-value measures the minimum statistical false-positive rate incurred when setting a threshold for test significance, the q-value measures the minimum false-discovery rate incurred when calling that test significant. A volcano plot for each comparison was generated that displays the negative $\log_{10}$-transformed p-value versus log 2-transformed fold change for each array locus.

Bioinformatic Analyses

For contig generation, all significantly differentially expressed array positions that met the fold-change criteria in each bioassay were selected and processed through Sequencher (Gene Codes Corporation, Ann Arbor, Mich.) with a minimum match percentage of about 95 to generate contigs. The generated contigs and the remaining orphan sequences were used for further analyses using the program BLAST2GO for identification and annotation. By using the inbuilt BLASTx algorithm, these sequences were used as queries in BLASTx searches against the Genbank nonredundant (nr) database with an e-value cut-off of ≤1e-03. The putative identification, annotation, and Gene Ontology (GO) terms for the sequences also were obtained through BLAST2GO. KEGG analyses were also performed.

Validation of Microarray Fold-Change Data by Quantitative Real-Time PCR

The fold-change data from the microarray results were validated by performing sets of quantitative real-time PCRs (qRT-PCR) with a CFX-96 Real-time System (Bio-Rad, Hercules, Calif.) using the SYBR-green detection method (SensiMix SYBR & Fluorescein one-step PCR reagent; Bioline, Taunton, Mass.). Thirty-four fungal-associated sequences (S6 Table of the Sen Article) with varying degrees of fold change were used to design primer sequences using the web-based tool Real-time Design (http://www.bio-searchtech.com/realtimedesign). The housekeeping gene lim-1 was used as a reference gene. Two µl of total RNA (from aliquots of 10 ng/µl) were taken from the original mRNA pools used for microarray hybridizations from all five colonies (5 treatments each) to synthesize cDNA using the iScript cDNA kit (Bio-Rad, Hercules, Calif.). Triplicate qRT-PCR reactions were performed for each of the biological replicate cDNA samples, along with a no-cDNA negative control, across the 34 primer sets (S14 Table of the Sen Article). Cycling conditions were an initial step of 95° C. for 3 minutes followed by 39 cycles of 95° C. for 20 seconds, 56° C. for 45 seconds, and 68° C. for 50 seconds. Quantification was performed by first generating a standard curve of primer amplification efficiency using whole-gut cDNA from colony #1 with a five-fold dilution series and then extrapolating the experimental samples onto the curve. Each triplicate sample was averaged to one data point for ease of graphical representation. The mean delta threshold cycle ($\Delta C_T$) was calculated for each data point by subtracting it from the average $C_T$ values of lim-1. Then, a $\Delta \Delta C_T$ value was calculated by subtracting average control (C) data points from F, B, I, FI, and BI treatments (see formula below using F as an example). These $\Delta \Delta C_T$ values were plotted against the corresponding fold-change levels from the microarray studies, and their associations determined non-parametrically by the Spearman rank correlation test.

$$\Delta \Delta C_T = \frac{1}{5} \sum_{j=1}^{5} \left( \frac{1}{3} \sum_{i}^{3} PF_i - \frac{1}{3} \sum_{i=1}^{3} \lim 1 F_i \right) - \frac{1}{5} \sum_{j=1}^{5} \left( \frac{1}{3} \sum_{i=1}^{3} PC_i - \frac{1}{3} \sum_{i=1}^{3} \lim 1 F_i \right)$$

where: j=number of biological replicates, I=number of technical replicates, P=given primer, lim1=lim1 primer; $F_i=C_T$ value of the ith technical replicate from the fungal-treated termite gut cDNA; and $C_i=C_T$ value of the ith technical replicate from the control treated termite gut cDNA.

Beta 1, 3 Glycosidase Activity by GHF7 Proteins

The GHF7-5 and GHF7-6 enzymes were specifically tested against a variety of substrates containing β-1, 3 and β-1, 6 glycosidic bonds—namely, laminarin (β-1, 3 and (3-1, 6), pustulan (β-1, 6), carboxymethylcellulose (β-1, 4), and carboxymethylcurdlan (β-1, 3), at a range of concentrations using 100 mM, filter sterilized HEPES buffer pH 7.0. Enzymes (0.5 µg) and substrates (0-1.25%) were incubated for about 1 hour at or near 30° C. Then 10 µL of enzyme/substrate solutions was combined with 90 µL of 3, 5-dinitorsalicyclic acid (DNSA) stop solution in a microplate, accompanied by a glucose standard curve. The plate was submerged in boiling water for about 10 minutes and an endpoint reading was taken at 540 nm.

Additionally, the enzymes of interest were tested for activity against four nitrophenol model substrates: o-nitrophenol-glucoside (oNPG), o-nitrophenol-cellobioside (oNPC), p-nitrophenol-glucoside (pNPG), and p-nitrophenol-cellobioside (pNPC) at 6 mM concentrations in 100 nM, pH 7.0 HEPES buffer. These assays contained about 95 µL of substrate in bugger and 5 µL (1 µg/µL) enzyme and were read kinetically for about 1 hour at around 30° C.

The laminarin assays were performed by testing GHF7-5 and GHF7-6 with 0.75% laminarin in about 100 mM sodium phosphate buffer at pH 7.0. Unlike previously, 0.5 µg of each enzyme and the substrate were incubated for about 10 minutes at 50° C. Thereafter, the samples were developed and measured as with the previous DNSA assay.

Finally, to test the efficacy recombinant GHF7-5 and GHF7-6 as antifungal enzymes, 1500 of 1×10⁴ conidia/mL of either *B. bassiana* or *M. anisopliae* were suspended in 0.5% Tween 20, no conidia controls contained only 0.5% Tween 20. These conidia were combined with 300 with 0.03 µg/µL recombinant protein in HEPES (no enzyme controls contained only buffer) and 2004, 5 mg/mL ampicillin in a 5 mL Eppendorf tube with the cap sealed with Parafilm® (Beemis) and each sample type was repeated in triplicate. These suspensions were incubated at about room temperature (~25° C.±2° C.) for about 24 hours shaking at about 50 rpms. Thereafter, 1004, of each suspension plate is transferred to potato dextrose agar plates containing 5 mg/mL ampicillin in triplicate. After about 96 hours at room temperature in the dark, the plates were counted for CFUs. Supernatants of theses assays were also subject to DNSA assays to assess the presence/abundance of reducing sugars in assays following incubation with GHF7s. For these assays, a mixture of 1004, of conidia-free in vitro assay supernatant and 1004, of DNSA reagent was incubated and analyzed as described above. Three technical replicates were performed for each sample type. Additionally, conidia suspensions were used to challenge termites to determine conidial potency following incubation. Groups of 10 termite works, pre-treated with 5% kanamycin or water for about 48-hours, were submerged in 1504, of one of the suspensions. Termite mortality was scored at 7 days post-inoculation.

Results

Impacts on Termite and Symbiont Behavior and Survival

Figure 5:
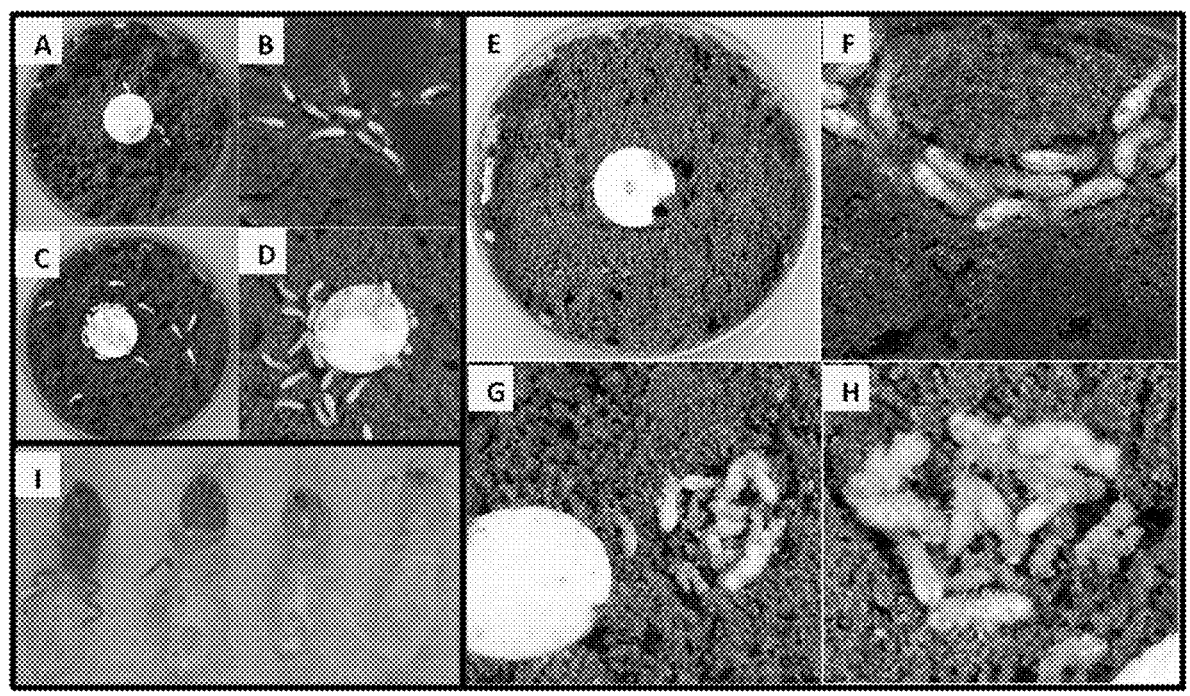
FIG. 5 shows representative examples of normal and infected termites following a treatment in accordance with the summary shown in FIG. 4, with control termites (SC) displaying normal behaviors labeled A, B; imidacloprid treated termites (I) labeled C, D; termites treated with a sublethal fungal dose (F) labeled E, F; termites treated with fungi+imidacloprid (F+I) labeled G, H; and termites treated with a combination of bacteria+imidacloprid (B+I) labeled I.

Seemingly normal behaviors such as grooming, tunneling, and light repellency, as well as no mortality, were displayed by solvent controls (SC) (see labels A and B in FIG. 5). Termites exposed to a sublethal imidacloprid concentration neither produced tunnels nor were repelled by light (labels C and D of FIG. 5), thus displaying mild intoxication effects. Termites treated with fungi or bacteria alone displayed normal behaviors (labels E and F of FIG. 5), while those exposed to combined F+I (labels G and H of FIG. 5) or B+I (label I of FIG. 5) treatments displayed clear pathology—i.e. mycosis or varying degrees of *Serratia* infection, respectively.

Figure 3A:
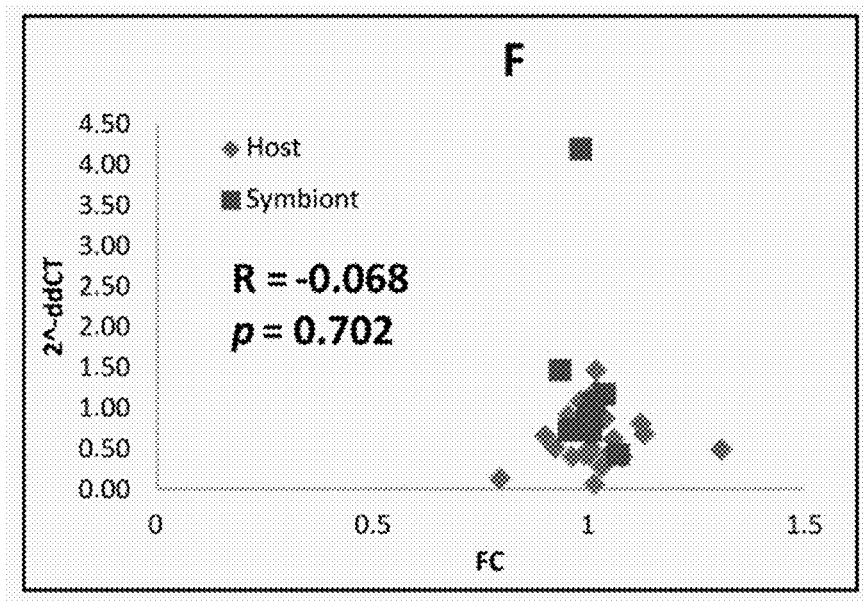
FIGS. 3A-3C show graphical results illustrating the correlation between microarray fold-change (FC) and qRT-PCR fold-change ($2^{-ddcT}$) values in genes representing a subset of 35 array-positives from F+I treatments to verify the robustness of microarray results, with a statistically significant correlation found for FI and I treatments (FIGS. 3B and 3C), but not fungi treatments (FIG. 3A), as expected (results were determined non-parametrically using the Spearman rank correlation test)
Figure 3B:
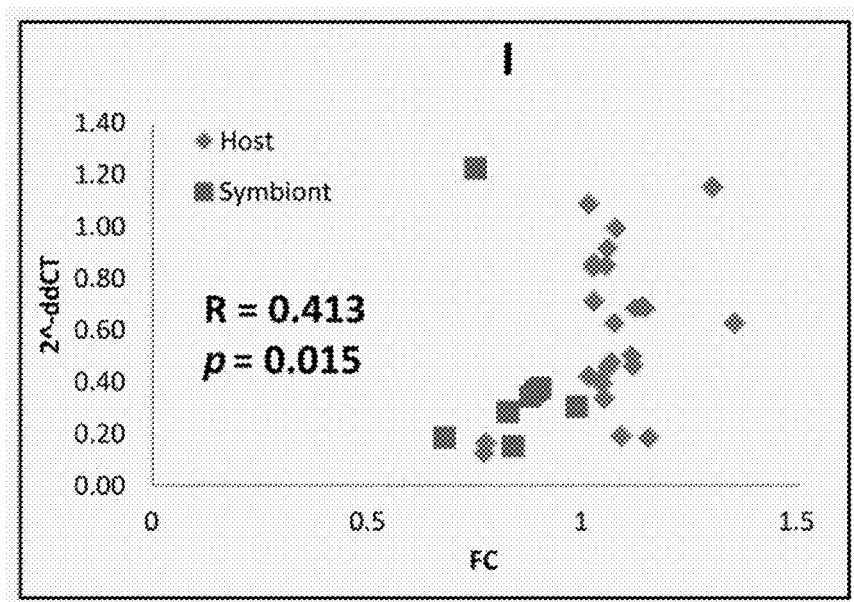
Figure 3C:
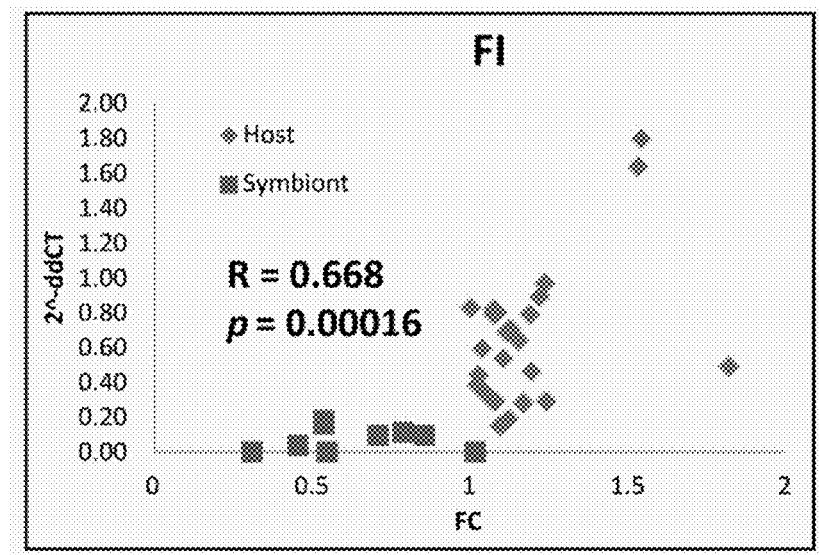

Mortality at 2 days, the time at which termites were sampled for microarray assessment, was not different among the 6 treatments (p=0.2609; Avg=7.0%, range=1-22%). By 7 days, however, imidacloprid greatly synergized the virulence of fungi, causing 100% mortality (FIG. 3), which is significantly greater than would be predicted by summation of the F and I single treatment mortalities (p=0.0182). Mortality caused by the B+I combination was more than that from B or I alone (see FIG. 6), but it was less than the F+I combination and was not synergistic (p=0.5947).

Figure 2B:
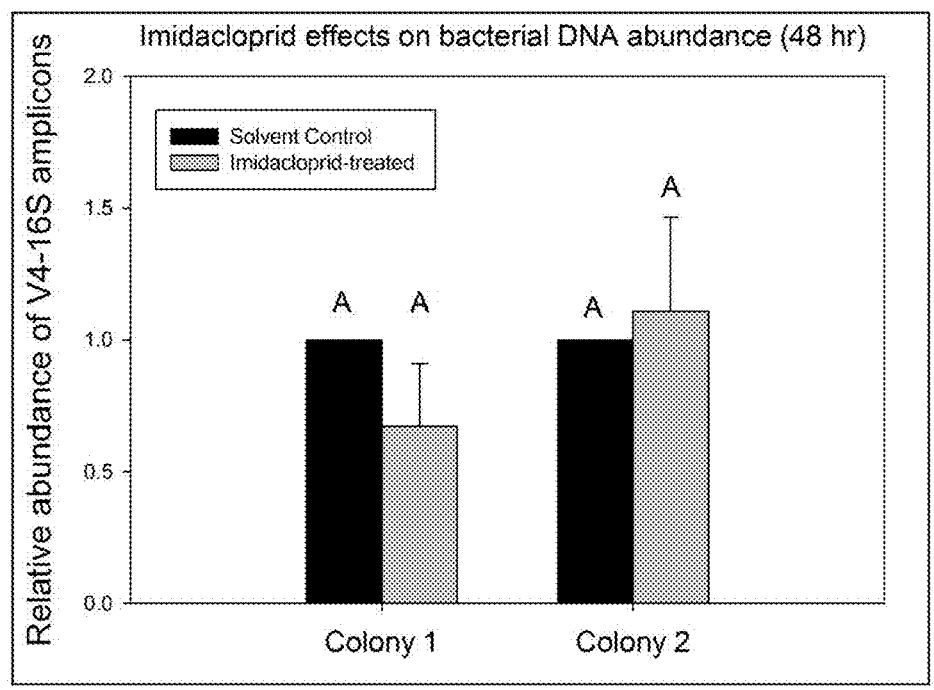

With respect to the post-hoc investigations of imidacloprid treatment on protist and bacterial gut symbiota, regardless of the variation in initial densities, imidacloprid exposure reduced protist populations in 5 of 6 treated termite colonies (see FIG. 1). The morphology and motility of the protists from treated and control termites were similar. Treatment did not seem to target any specific protist clade, but instead resulted in about a 25-50% reduction of representative protist groups. Conversely, based on two independent measures, gut bacterial populations were not affected by imidacloprid exposure. These independent bacterial measures included (i) quantitation based on culturable colony-forming units (FIG. 2A) and (ii) 16S rDNA abundance (FIG. 2B).

General Transcriptome Level Impacts

The microarray analyses were conducted to identify treatment impacts at the transcriptome level. Arrays contained 14,500 cDNA oligonucleotides representing a blend of ~10,500 host gut and protist-symbiont genes, with positions annotated accordingly as being from host, symbiont, or mixed origins. RNA of whole guts from 5 replicate colonies was sampled 2 days post-exposure to each of the six treatments. Gene expression for the F, B, I, F+I or B+I exposed guts was normalized individually to the common solvent control (SC) treatment. Only positions changing by +/−1.2-fold and p<0.05 were considered further. qRT-PCR was used to validate microarray results for a subset of 34 F+I passing genes, using the original F+I, F, and I cDNA samples as qRT-PCR templates. Consistent with microarray studies conducted in parallel with the current study, these validations revealed a significant correlation between microarray and qPCR results (see FIGS. 3A-3C).

Figure 6:
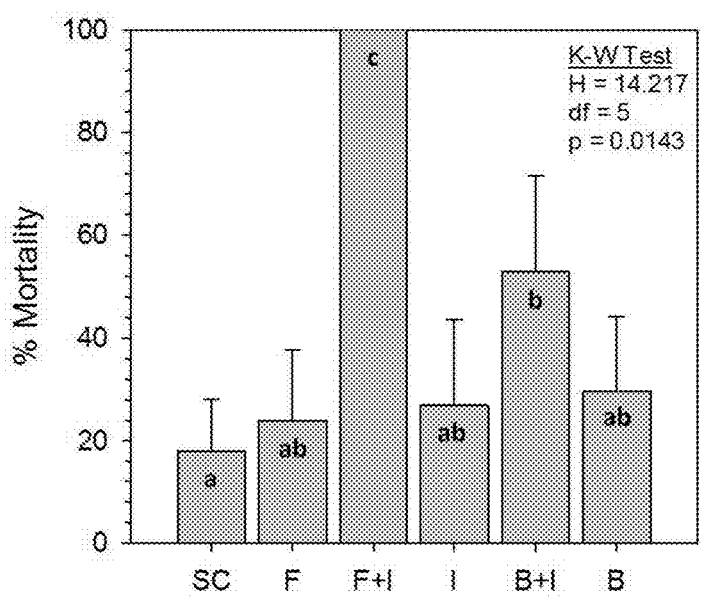
FIG. 6 represents bioassay mortality results after 7-day exposures to six treatments in accordance with the summary shown in FIG. 4, with the highest mortality occurring in combination treatments of fungi+imidacloprid (F+I) and bacteria+imidacloprid (B+I); Kruskal-Wallis (K-W) test statistics are also provided indicating the significance of the entire model and bars with the same letters (a, b, c) are not different by Mann-Whitney U-tests ($p<0.05$)
Figure 7:
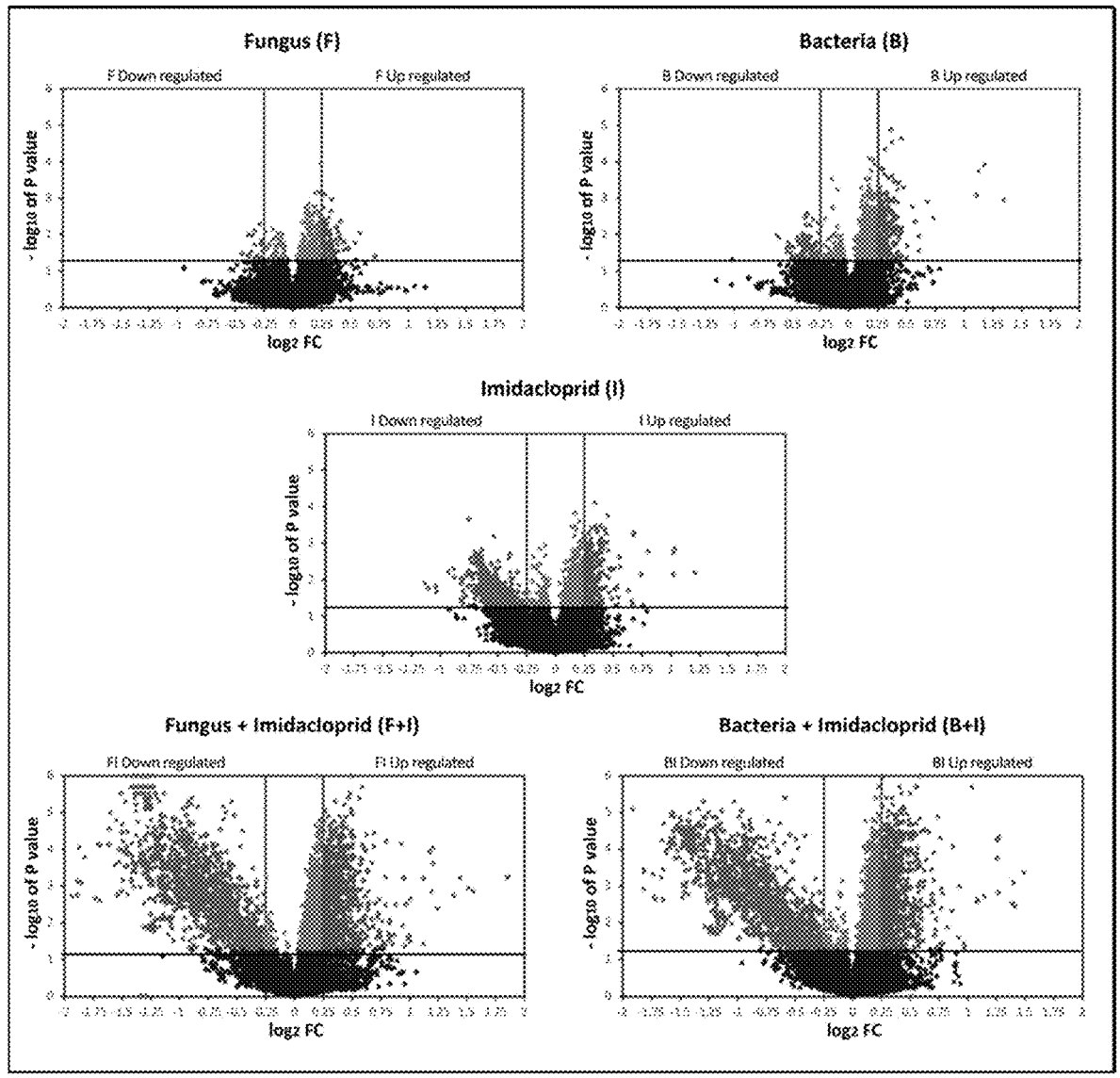
FIG. 7 shows microarray volcano plots showing differing numbers of passing array positions in F (fungi), I (imidacloprid), B (bacteria), F+I (fungus+imidacloprid), B+I (bacteria+imidacloprid) treatments; spots located in the upper right quadrant of each plot indicate significant upregulated array positions and spots located in the upper left quadrant indicate downregulated array positions with +/−2-fold change (FC) upregulation and downregulation, respectively.

In agreement with the bioassay results represented in FIG. 6, the microarray volcano plots of FIG. 7 show larger numbers of array positions responding in the dual F+I and B+I treatments compared with the single F, B, and I treatments. Exposure to the bacterial or fungal propagules alone induced comparatively minor changes in the gut metatranscriptome. In comparison, exposure to sublethal concentrations of the nicotinoid (I) caused greater gene downregulation than did B and F treatments—likely a result of the nicotinoid's impact on the chemistry of the hindgut protist community. Venn diagrams showing passing array positions shared among treatment categories are provided in FIGS. 13A-13C. The F, B, and I treatments upregulated 85, 214, and 260 transcripts in the array, respectively, and downregulated 16, 89, and 504 array positions, respectively. Treatments that combined the B or F with I led to synergized increases in both upregulated and downregulated array positions. Overall, more array positions are shared among the F+I and B+I dual treatments than among the single F, B, and I treatments, indicating that imidacloprid plays a key role in altering gene expression.

After forming sequence contigs at the 90% similarity level from only passing array positions, the host or symbiont origins of the contigs and remaining "singlets" were tallied across treatments (Table 1; S1-S5 Tables of the Sen Article). In total, 3,187 genes were differentially (p<0.05) expressed across all comparisons, with 79% occurring in the F+I and B+I combination treatments. Among the single-challenge treatments, imidacloprid had the largest impact on transcript expression profile (393), followed by bacteria (196) and fungi (83). Finally, the majority of upregulated genes across all treatments were of host origin, and conversely, the majority of downregulated genes were of symbiont origin (Table 1).

TABLE 1

Summary table showing up- and down-regulated contigs and "singletons" from host and symbiont in each treatment category (F, B, I, F + I and B + I). Overall, greater numbers of host genes were upregulated and symbiont genes were downregulated by the various treatments. "Mixed" refers to genes that were sampled from both host and symbiont libraries.

|   | UPREGULATED | | | | DOWNREGULATED | | | | |
|---|---|---|---|---|---|---|---|---|---|
|   | Host | Symbiont | Mixed | Totals | Host | Symbiont | Mixed | Totals | Overall |
| F | 56 | 12 | 1 | 69 | 6 | 8 | 0 | 14 | 83 |
| B | 142 | 13 | 1 | 156 | 6 | 34 | 0 | 40 | 196 |
| I | 157 | 19 | 1 | 177 | 8 | 205 | 3 | 216 | 393 |
| F + I | 568 | 48 | 3 | 619 | 42 | 567 | 7 | 616 | 1235 |
| B + I | 634 | 63 | 4 | 701 | 26 | 545 | 8 | 579 | 1280 |
| Totals | 1557 | 155 | 10 | 1722 | 88 | 1359 | 18 | 1465 | 3187 |

Gene Ontology and Pathway Analyses

Figure 14A:
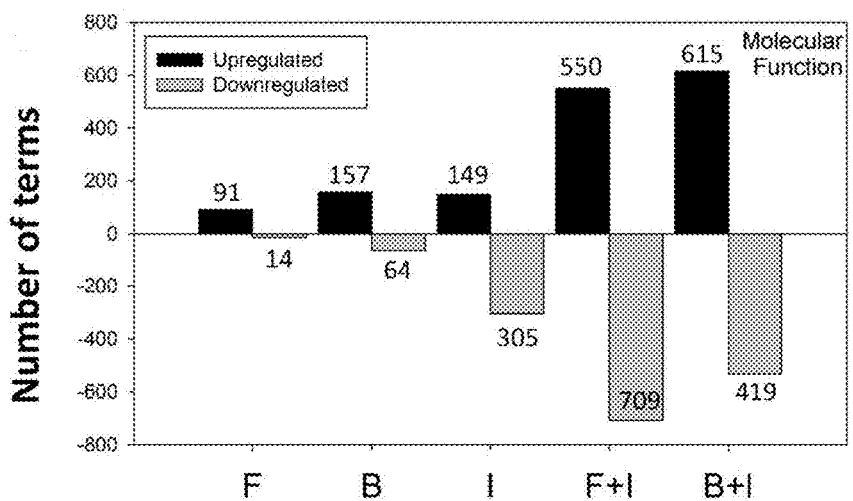
FIGS. 14A-14C illustrate graphical representations of the total number of upregulated (black) and downregulated (gray) GO terms across the treatment categories F, B, I, F+I, and B+I, in the GO categories of Molecular Function (FIG. 14A), Biological Process (FIG. 14B), and Cellular Location (FIG. 14C), with greater numbers of GO terms occurring in the paired F+I and B+I treatments than in the single F, B, or I treatments.
Figure 14B:
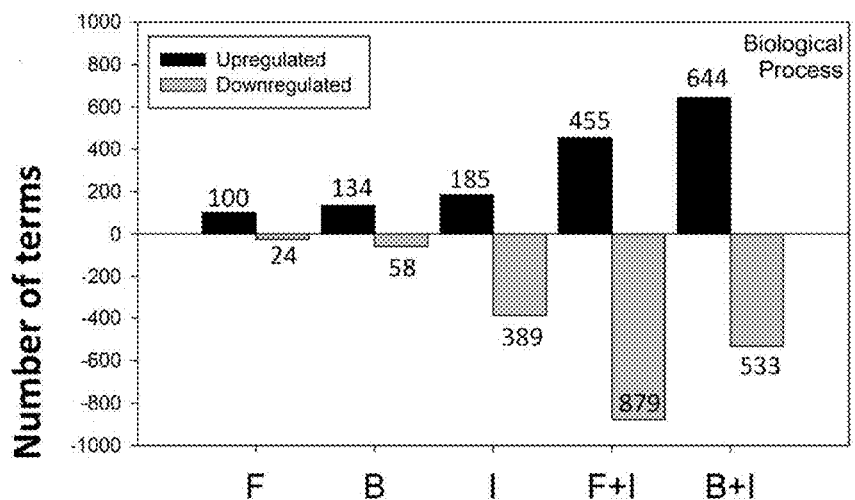
Figure 14C:
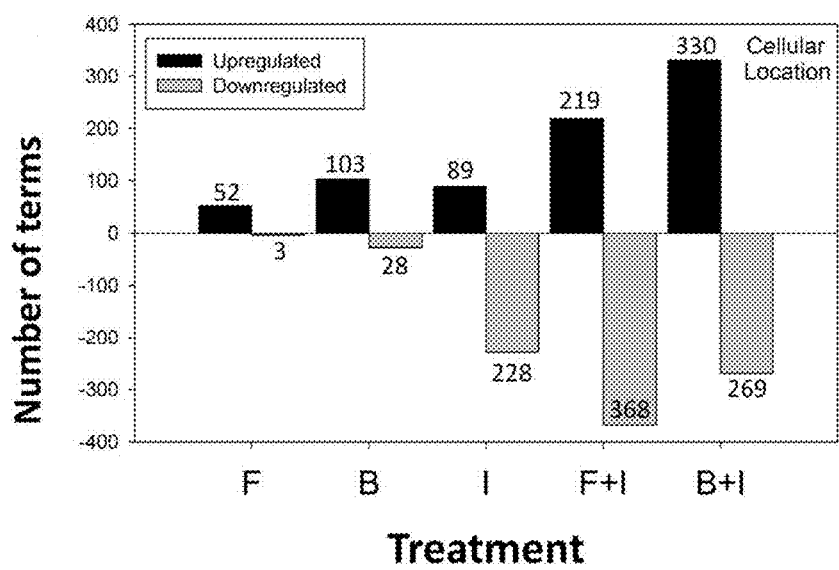

All passing contig and singleton sequences from microarrays were subject to analysis by KEGG and BLAST2GO (see Methods and Materials above for details). First, KEGG analyses revealed impacts on general housekeeping pathways, evidencing that they are downregulated in I, F+I, and B+I treatments (S6-S10 Tables of the Sen Article). These downregulated KEGG pathways include glycolysis and gluconeogenesis, the TCA cycle, purine and amino sugar metabolism, and others. BLAST2GO analyses were also conducted, which included the three gene ontology (GO) analyses Molecular Function (MF), Biological Process (BP), and Cellular Location (CL). Consistent with the general results summarized above, the paired F+I and B+I treatments had larger numbers of terms in all three GO categories than did the single treatments (see FIGS. 14A-14C). Overall, the F+I treatment had more GO terms in each category, followed closely by B+I. Also, the majority of terms in the I and F+I treatments were downregulated (S11-S13 Tables of the Sen Article). Top MF terms included hydrolase activity and various types of binding (i.e. nucleotide, protein, ATP, GTP, and broad-spectrum). Top BP terms included cellular and nucleobase-containing metabolic processes, transmembrane and intracellular protein transport, GTPase-mediated signal transduction, and anatomical structure morphogenesis. Top CL terms included intracellular, cytosol, cytoplasm, protein complex, ribosome, and membrane locations.

Due to the observed synergy with F+I treatments, this category was considered in additional detail. In the F+I category, the top upregulated MF terms all included binding (protein, ATP, zinc ion, and nucleotide), but the most downregulated terms also included binding (GTP, ATP, and protein). The top upregulated BP terms were proteolysis, oxidation-reduction and carbohydrate metabolic processes; the most downregulated were GTP catabolism, microtubule-based movement, and protein polymerization. In the CL category, the top upregulated terms were extracellular region, membrane, nucleus, and intracellular locations, whereas the most downregulated terms were cytoplasm, microtubule, and integral to membrane.

Candidate Genes

A subset of 79 responsive genes from 9 categories is summarized in Table 2. A complete summary of all 3,187 responsive genes across all treatments is provided in S1-S5 Tables of the Sen Article, which is incorporated by reference herein. Categories considered in detail included antimicrobial, carbohydrate-active, chemosensory, detoxification, JH-responsive, neuropeptide, cytochrome P450, transcription factor, and "other." Most antimicrobial genes from the list were upregulated in either the F+I or B+I treatment (Table 2). Key antimicrobial genes identified include lysozyme, PRPs, termicin, transferrins, and leucine-rich repeat proteins. Many carbohydrate-active genes were differentially expressed among treatments, but the most notable are the GHF7 cellulases, which were all significantly downregulated in the F+I treatment, including one isoform that was downregulated over 1000x. Several of the same GHF7s downregulated in the F+I treatment were upregulated with the less impactful B+I treatment. Several chemosensory-related genes from the takeout family were also upregulated with various treatments and particularly in F+I.

TABLE 2

A subset of upregulated (values >1) and downregulated (values <1) candidate genes identified across all microarray treatment categories (F, B, I, F + I and B + I) and their origins from either host or symbiont (see text for details). See S1-S5 Tables of the Sen Article for a full listing of significant responsive genes from each treatment category.

| Category | Candidate genes | Fold change (by treatment) | | | | | Origin |
|---|---|---|---|---|---|---|---|
|  |  | F | B | I | F + I | B + I |  |
| Antimicrobial | antimicrobial peptide 7848 |  |  |  | 1.41 |  | Host |
|  | cathepsin b |  |  |  | 0.423 |  | Symbiont |
|  | ferric-chelate reductase 1 |  |  |  | 1.34 |  | Host |
|  | heat shock protein |  |  |  | 0.271 |  | Symbiont |
|  | heat shock protein |  |  |  | 0.261 | 2.59 | Symbiont |
|  | heat shock protein 90 |  |  |  |  | 2.67 | Symbiont |
|  | laccase 2 |  |  |  | 1.37 |  | Host |
|  | lysozyme p |  |  |  | 1.43 |  | Host |

TABLE 2-continued

A subset of upregulated (values >1) and downregulated (values <1) candidate genes identified across all microarray treatment categories (F, B, I, F + I and B + I) and their origins from either host or symbiont (see text for details). See S1-S5 Tables of the Sen Article for a full listing of significant responsive genes from each treatment category.

| Category | Candidate genes | F | B | I | F + I | B + I | Origin |
|---|---|---|---|---|---|---|---|
| | lysozyme precursor | | | | 1.67 | | Host + Symbiont |
| | peptidoglycan recognition partial | | | | 1.77 | | Host |
| | peptidoglycan-recognition protein s2 | | | | 1.81 | | Host |
| | termicin | | | | 1.39 | | Host |
| | transferrin | | | | 1.31 | | Host |
| | transferrin 3 | | | | 1.50 | | Symbiont |
| | alpha amylase | | | | 1.69 | | Host |
| | cell surface leucine-rich repeat-containing protein | | 1.23 | 1.25 | | | Host |
| | leucine-rich repeat-containing protein | | | 0.68 | | 2.08 | Symbiont |
| | leucine rich repeat family | | | 0.74 | | 1.46 | Symbiont |
| | leucine-rich repeat-containing protein 48 | | | 0.73 | | 1.88 | Symbiont |
| | leucine rich repeat protein 1 | | | 0.64 | | 1.44 | Symbiont |
| | leucine rich repeat family protein | | | 0.71 | | 1.72 | Symbiont |
| | leucine rich repeat family | | | | | 1.49 | Symbiont |
| | leucine-rich repeat-containing protein 56 | | | | | 1.74 | Symbiont |
| | leucine rich repeat family | | | | | 1.48 | Symbiont |
| Carbohydrate-active | alpha- -mannosyl-glycoprotein 2-beta-n-acetyl-glucosaminyltransferase | 1.36 | | | | | Host |
| | beta-galactosidase-like | 1.33 | | 1.29 | 1.48 | | Host |
| | GHF 1 (beta-glucosidase) | | | 1.28 | 1.32 | | Symbiont |
| | beta-lactamase | | | | 0.550 | | Symbiont |
| | brain chitinase and chia | | | | 1.24 | | Host |
| | carbohydrate-binding protein | | | | 0.715 | | Host |
| | chitinase-like protein idgf4-like | 1.19 | | | | | Host |
| | c-type lectin precursor | | | | | 0.66 | Host |
| | dockerin | | | 0.77 | 0.545 | 1.57 | Symbiont |
| | endo- -beta-d-glucanase | | | | 1.33 | | Symbiont |
| | GHF 3 | | | | 0.466 | | Symbiont |
| | GHF 3 N-terminal domain protein | | | 0.67 | | 1.78 | Symbiont |
| | GHF 10 | | | | 0.733 | | Symbiont |
| | GHF 7 (GHF7-5) | | 0.80 | 0.76 | 0.001 | 1.61 | Symbiont |
| | GHF 7 | | | | 0.480 | 1.71 | Symbiont |
| | GHF 7 | | | | 0.572 | 1.51 | Symbiont |
| | GHF 7 | | | | 0.552 | 1.51 | Symbiont |
| | GHF 7 | | | | 0.508 | | Symbiont |
| | GHF 7 | | | | 0.832 | | Symbiont |
| | GHF 7 | | | | 0.786 | | Symbiont |
| | GHF 7 | | | | 0.536 | | Symbiont |
| | GHF 13 (maltase 2) | 1.22 | | | | | Host |
| | maltase a2 | 1.26 | | | | | Host |
| Chemo-sensory | takeout family protein | | 1.20 | 1.21 | | | Host |
| | takeout family protein | | | 1.20 | | | Host |
| | takeout family protein | | | | 1.23 | | Host |
| | takeout family protein | | | | 1.20 | | Host |
| | takeout family protein (JHBP like) | | | | 1.25 | | Host |
| Detoxification | abc transporter family protein | | | | 0.551 | 1.54 | Symbiont |
| | abc transporter family protein | | | | 0.545 | 1.68 | Symbiont |
| | catalase | | | 1.20 | | | Host |
| | epoxide hydrolase 4-like | | | | | 0.81 | Host |
| | multidrug resistance protein 2 | | | | | 2.46 | Symbiont |
| | peroxidase ppod1 | | | | | 2.39 | Symbiont |
| JH-Responsive | 50 Kda midgut protein | | 2.09 | 1.95 | 2.30 | | Host |
| | insulin receptor | | | | 1.36 | 1.29 | Host |
| | JH-inducible protein | | 1.50 | 1.46 | | | Host |
| | nli interacting factor-like phosphatase family protein | | | | 2.37 | 0.36 | Host |
| | tyramine beta hydroxylase | | | | 1.42 | | Host |
| | arylsulfatase j-like | | | 1.24 | | | Host |
| Neuropeptide | allatostatin neuropeptide precursor | 1.27 | | | 1.50 | | Host |
| | neuropeptide f | | | | 1.26 | | Host |
| Cytochrome P450 (CYP) | CYP304A1-like | | 1.23 | | 1.43 | | Host |
| | CYP4C1-like | | 1.24 | 1.24 | 1.25 | | Host |
| | Cyp4C1-like | | | 1.21 | 1.25 | | Host |
| | CYP6AM1-like | | 1.26 | 1.27 | 1.35 | | Host |
| | CYP6K1-like | | | | 1.22 | | Host |

TABLE 2-continued

A subset of upregulated (values >1) and downregulated (values <1) candidate genes identified across all microarray treatment categories (F, B, I, F + I and B + I) and their origins from either host or symbiont (see text for details). See S1-S5 Tables of the Sen Article for a full listing of significant responsive genes from each treatment category.

| Category | Candidate genes | Fold change (by treatment) | | | | | Origin |
| --- | --- | --- | --- | --- | --- | --- | --- |
| | | F | B | I | F + I | B + I | |
| | CYP9E2-like | | | 1.30 | 1.34 | | Host |
| | CYP9E2-like | | | | 1.20 | | Host |
| | CYP15F1 (R. flavipes) | | | 1.19 | | | Host |
| | CYP4U3V1 (R. flavipes) | | | | 1.22 | | Host |
| Transcription factor | EF hand family protein | | | | | 2.48 | Symbiont |
| | fork head | | | | 1.22 | | Host |
| | RNA-binding protein luc7-like 2-like | | 1.60 | 1.47 | | | Host |
| Other | cysteine synthase a | | | 0.46 | 0.301 | | Symbiont |

Two inter-related groups are the detoxification and P450 categories. Key detoxification genes included ABC transporters (downregulated in F+I; upregulated in B+I), catalase, and epoxide hydrolase. Nine P450s from the CYP4, 6, 9, 15, and 304 families were all upregulated in response to various treatments, but mostly in the F+I treatment. Several genes occurring in the JH-responsive category were initially identified in a prior study specifically investigating JH impacts on caste differentiation and gut gene expression: 50 kDa Midgut protein, insulin receptor, nli phosphatase, tyramine beta hydroxylase, and arylsulfatase. Two neuropeptide-encoding genes were also upregulated that included allatostatin and neuropeptide F. Three transcription factors were all upregulated with I, F+I and/or B+I treatments; one (EF Hand family protein) was previously identified in association with dietary phenolics and potentially phenolic-mediated melanization processes. Lastly, in the "other" category, a gene that was significantly downregulated in I and F+I treatments (cysteine synthase a) was previously upregulated by cellulose feeding (the substrate used in the current study). In at least one exemplary embodiment of the present disclosure, and as described below in additional detail, these findings can be leveraged (either alone or in conjunction with additional strategies) to control termite populations. The genes/transcripts that were upregulated in the experiments and studies described herein were presumably turned on as a response to pathogen infection and conferred defense against the pathogen. In at least one embodiment of a method for controlling termite populations, at least one of the above-identified antimicrobial host genes (or the proteins they encode) may be downregulated using a technique such as RNA interference, inhibited with pharmacological agents or pesticides (i.e. to eliminate the protists/bacteria themselves that induce upregulation of the antimicrobial host genes), or using other methodologies known in the art to prevent and/or decrease the observed upregulation, thereby increasing the termite's susceptibility to natural or introduced pathogens. While such host genes may comprise any of the antimicrobial host genes identified herein, in at least one exemplary embodiment, one or more of the upregulated antimicrobial host genes may be selected from the following group: allatostatin, neuropeptide F, lysozyme, pathogen-recognition proteins, termicin, leucine-rich repeat proteins, and/or transferrins.

GHF7-5 and 7-6 Activity Against β-1, 3 and/or β-1, 6-Glycosidic Bonds

As described above, GHF7-5 and 7-6 activity was tested on a variety of substrates with varying incubation times and buffers. Ultimately, the best activity of this enzyme was with sodium acetate buffer at pH 7.0 incubated at 50° C. for about 10 minutes on 0.75% laminarin. The other reducing sugar assays did not show enzyme activity scaled with substrate concentration. Nitrophenol assays with HEPES buffer also failed to show activity.

GHF7-5 and 7-6 Antifungal Activity

Following in vitro incubation of fungal conidia with recombinant GHF7-5 and 7-6 enzymes, M. anisopliae show significant reductions in fungal colony forming units relative to a buffer control as shown in FIG. 9. *B. bassiana* showed some decrease in conidial success, however, there was a large amount of variation across replicates. Additionally, supernatant from in vitro assays of all enzyme-fungus combinations had detectable levels of reducing sugars present, which were absent from buffer controls, thus indicating the breakdown of polysaccharides in GHF-positive in vitro assays (see FIG. 10).

Pre-Treatment of Fungal Pathogenic Agents with GHF7s

The effect of pre-treatment of fungal conidia with GHF7s on subsequent termite survival was also evaluated (see FIG. 12). Defaunated termites that were subsequently challenged with GHF7 pre-treated *B. bassiana* had higher survival rates than those challenged with buffer pre-treated *B. bassiana* conidia (i.e. shown as light bars). Accordingly, *B. bassiana* pre-treatment with GHF7-5 or 7-6 appear to positively impact defaunated termite survival, whereas there was no statistical effect of pre-treatment in *M. anisopliae*. Such results may be attributable to the considerable variability across termite colonies that may impede the interpretation of the results.

Bacterial Metatranscriptome

The function of bacteria in *R. flavipes* guts was also evaluated to shed light on the extent to which host-prokaryote collaboration(s) plays a role in defense against fungal entomopathogens. Specifically, *R. flavipes* termite colonies (collected on the Purdue University campus in West Lafayette, Ind.) were reared in darkness at 22±2° C. with ~40% relative humidity and provided with pine wood shims and brown paper towels as a food source. The pathogen *B. bassiana* isolate #5477 was cultured in darkness on PDA at room temperature. To collect conidia for bioassays, 10 to 12-day old *B. bassiana* culture plates were flooded with 5 mL of filter sterilized 0.5% Tween-20. Conidial concentration was determined via hemocytometer and diluted to $1.25\times10^4$ conidia/mL for termite inoculation.

In sum, the data disclosed herein provides the most complete gut metatranscriptome from *R. flavipes* to date, especially with respect to bacterial contributions. The practical effects of these findings are significant and may be exploited to attenuate host responses and, thus, effectively increase pathogen virulence. For example, in at least one embodiment, novel methods for controlling termite populations are provided. Based on a concept similar to the previously described methods that focus on the downregulation of known antimicrobial host genes/contigs themselves, these methods increase termite susceptibility to natural or introduced pathogens by targeting the specific bacterial groups that upregulate the genes and/or contigs identified in the present disclosure as encoding symbiont-mediated immunity.

In at least one exemplary embodiment of such a method, the method may be based on the new mechanism for bacterial-mediated anti-fungal defense by means of bacterial-mediated anti-fungal enzyme action identified by the investigations described herein. There, the method comprises at least the step of targeting one or more specific bacterial groups that produce bacterial-mediated anti-fungal enzymes using antimicrobial drugs, other pharmacological agents, or other methods known in the art. In addition to amidohydrolase 2 enzyme, 15 additional symbiont contigs (6 protist and 9 bacterial) are identified that exhibit significant fold-changes over the respective baseline levels in response to *B. bassiana* pathogen challenge and, thus, would be affected by the elimination or reduction of such bacterial group. Reducing or eliminating the specific bacterial groups that produce such enzymes increases the termite's susceptibility to natural or introduced pathogens.

Ribo-Depletion Produces a Quality Metatranscriptome Assembly

One of the goals of the investigations described herein was the identification of candidate genes facilitating symbiont-mediated fungal pathogen defense in *R. flavipes*. A unique transcriptome preparation and analysis approach was used that allowed for the ribodepletion of rRNA from total RNA rather than enriching (and potentially biasing) for mRNAs. A commercial library preparation kit was modified to efficiently deplete all total RNA samples of anticipated prokaryotic and eukaryotic rRNAs. This strategy resulted in low rRNA content in the sequenced libraries and yielded a robust assembly of over 2 million contigs, >30,000 of which were annotated through our annotation pipeline.

The contig annotation pipeline took a conservative (and, thus, reliable) approach to identifying termite, bacterial, protist, and archaeal sequences from a custom termite consortium database built from publicly available sequence data (see Table 3 below). Additionally, identifying 9,730 best reciprocal hits, out of the 14,610 annotated genes in the *Z. nevadensis* official gene set (OGS), from gut tissue of worker termites in a different taxonomic family of Isoptera, speaks to the quality of the assembly. In contrast, the reference sequences for protist and archaeal symbionts proved inadequate for the purposes of these investigations. With only 248 and 174 RBH respectively, undoubtedly important protist and archaeal contributions to this system were under-sampled, both generally and in reference to fungal defense specifically. However, the termite and bacterial libraries were significantly more complete, thus providing a more complete picture of bacterial contributions to their termite host and the gut consortium as a whole. Compared to previous metatranscriptomic efforts using mRNA enrichment in this system, the present assembly identified many more bacterial contributions, emphasizing the advantages of a ribodepletive strategy.

Similar to studies in higher termites that lack protist symbionts, this assembly showcases a diversity of carbohydrate active genes including over 200 glycosyl hydrolases of bacterial origin. As shown in Table 5 below, the investigations of the present disclosure also support that bacterial symbionts possess a complete amino acid biosynthetic toolkit and the presence of nitrogen metabolism genes like nitrogenases, nitroreductases, and ureases corroborate the importance of bacterial symbionts for nitrogen recycling and fixation in the lower termite gut. Additionally, the results of the investigations described herein support that bacteria in the *R. flavipes* gut express a diversity of carbohydrate metabolism transcripts, which include cellulases and hemicellulases, glycosyl transferases, carboxylesterases, and polysaccharide lyases and appear to be both complementary and redundant to those encoded by the host termite (see Table 5). This further supports that bacteria of lower termites like *R. flavipes* play an active role in wood digestion and that carbohydrate metabolism is not restricted to flagellate/protist digestive vacuoles precluding bacterial catabolism.

In addition to anabolic and catabolic potential, the termite gut metatranscriptome is rich in bacterial transporters. These transporters, particularly ABC transporters, shed light on a practical aspect of the termite gut symbiosis. With a total of 787 annotated bacteria-derived transporters, including those responsible for transporting all types of organic molecules and metal ions, the idea of a hypercollaborative *R. flavipes* gut environment with influx and efflux of all types of compounds between members of the consortium is supported. ABC transporters have been noted as playing important roles in other insect-microbe relationships, particularly where metabolic partitioning is involved. Taken together, the complementary nature of the bacterial and termite contigs found in the gut metatranscriptome provides the foundation for a more complete view of this tripartite symbiosis.

*B. bassiana* Challenge Results in Oxidative Stress

Figure 18A:
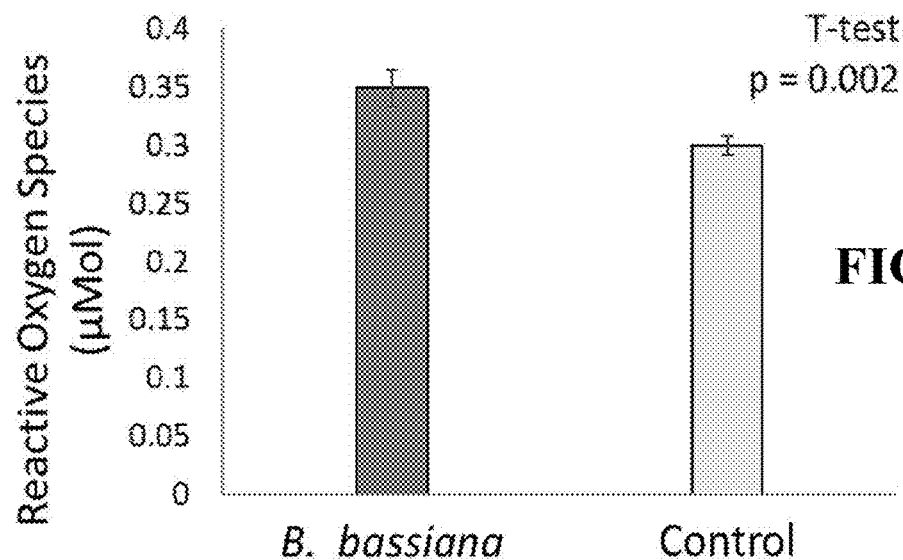
FIGS. 18A and 18B are bar graphs showing results of post-hoc experiments representative of oxidative stress, with FIG. 18A indicative of detection of ROS in termite worker guts following *B. bassiana* challenge (bars represent measured ROS in *B. bassiana* (dark bar) and no treatment control (light bar)) and FIG. 18B indicative of detection of glutathione S-transferase (GST) activity following *B. bassiana* challenge (bars represent measured GST specific activity in *B. bassiana* treatments (dark bar) and negative controls (light bar) for termite worker guts normalized to blanks that received no reduced glutathione); error bars represent SEM.

The results of the presently described investigations support that, 48-hours post inoculation with *B. bassiana* conidia, the termite gut experiences general oxidative stress. ROS estimation indicates a significant increase in oxidative stress in pathogen challenged guts (FIG. 18A). Additionally, up-regulation in host antioxidant enzyme-coding genes for peroxiredoxin (SEQ ID No. 4) and GST (SEQ ID No. 5) occurred at the protein-level with increases in GST enzyme activity (Table 7, FIG. 18B). The transcriptome data supports that the origin of the observed increase in ROS is the up-regulation of OXPHOS complexes I, III, and IV without corresponding up-regulation of ATP synthase, which may result in uncoupling-related proton leakage. Production of ROS in response to pathogen challenge is a common defense strategy in eukaryotes and, coupled with more traditional immune-associated pathways, may serve as a mechanism for endogenous termite anti-fungal defense.

In line with the increased oxidative stress that was observed, many up-regulated symbiont contigs were also associated with response to this type of damage. Two protist transcripts encoding signaling kinases, CAMKII (SEQ ID No. 18) and MAPK1 (SEQ ID No. 19), were up-regulated and likely involved in triggering cascades responsible for coordinating stress responses like oxidative stress and pathogen challenge. Additionally, two 3'-5' exonuclease genes were also up-regulated (SEQ ID Nos. 16 and 17). These genes encode enzymes like DNA Pol I, which is responsible for DNA repair and has been shown to be responsive to oxidative stress.

Amidohydrolase 2, a candidate Symbiont Mediated Anti Fungal Response Mechanism

At least one new candidate mechanism of symbiont-mediated anti-fungal defense was discovered as a result of the presently described investigations. The specific hypothesis tested was that bacteria collaborate with the rest of the holobiont to combat invaders, with an ideal candidate gene being up-regulated in response to pathogen presence and its product possessing putative functions that might contribute to defense. Following these criteria, one candidate was identified: amidohydrolase 2 (SEQ ID. No. 3).

As supported by the data provided below, amidohydrolase 2 is a bacterial gene up-regulated 3.4×48-hours post-inoculation with *B. bassiana*. Amidohydrolases are a large family of diverse enzymes which are catalytically promiscuous. These activities include hydrolysis, isomerization, and decarboxylation of diverse substrates. Amidohydrolases are found across domains of life and are particularly of note in bacteria due to their role in antibiotic resistance. Beta-lactamases, enzyme class 3.5.2.6, catalyze the deactivation of beta-lactam antibiotics like penicillin. While *B. bassiana* does not produce penicillins, it is known to produce ooconidiain which it uses to evade insect anti-fungal defenses like PPO and antifungal peptides. Notably, hydrolysis of quinone oocondiain would significantly contribute to *B. bassiana* defense in the termite gut. Accordingly, the findings of the present disclosure support that the transcript for amidohydrolase 2 catabolize fungal metabolites that inhibit insect immune responses and have antibiotic activity.

These findings were further supported by independent post-hoc experiments. Specifically, antibiotic treatment with 5% kanamycin (an antimicrobial drug) mitigated both the *B. bassiana*-mediated induction of amidohydrolase 2 (i.e. downregulates the amidohydrolase target gene) and results in a 3-fold increase in termite worker susceptibility to *B. bassiana* (see FIGS. 19A and 19B). These findings strongly support the importance of symbiont-mediated protection against *B. bassiana* and further implicate amidohydrolase 2 as a bacteria-contributed mechanism of protection. Coupled with previous findings of protist-derived anti-fungal defenses, the presently described model of antifungal defense in the termite hindgut 2000 highlights the collaborative nature of immune physiology within the termite holobiotic system (FIG. 20). FIG. 20 shows a model depiction of the termite hindgut 2000 that includes endogenous antifungal enzymes, encapsulation, and phagocytic mechanisms (collectively labelled 2002) to defend against pathogens, protists 2004 that contribute β-1,3-glucanases that have been shown to reduce conidial germination, and bacterial amidohydrolase 2006 that is up-regulated in response to fungal pathogen challenge In addition to amidohydrolase, there are 15 symbiont (6 protist and 9 bacterial) contigs that exhibit significant fold-changes (as compared to baseline levels) in response to *B. bassiana* pathogen challenge (see Tables 6 and 7, and also described in further detail in Peterson & Scharf, *BMC Genomics,* 17:772 (2016) (the "Peterson & Scharf Article"), which is incorporated by reference herein in its entirety). While these genes do not have any conventionally-known functions, the present disclosure supports that they possess important anti-fungal properties and may be targeted either through the downregulation methodologies previously described or by reducing or eliminating the bacterial groups that produce such enzymes.

The investigations and methodologies employed in connection with the herein described metatranscriptome analysis will now be described in detail.

Bioassay Setup & Dissections

Groups of 30 termite workers were either submerged in a suspension of $1.25\times10^4$ conidia/mL in 0.5% filter sterilized Tween-20 or Tween-20 alone for one minute. Termites were transferred to 33 mm plastic dishes containing 2 $cm^2$ of Whatman filter paper wetted with 1004, of deionized water. Bioassays were held at 28±2° C. for 48 hours in complete darkness in a growth chamber. Paired treatment groups (control and pathogen challenged) from 3 distinct termite colonies served as biological replicates, for a total of 6 samples. After 48 hours in bioassay, termite whole guts were dissected from 25 workers per treatment, submerged in RNAlater (ThermoFisher Scientific) and stored at −80° C.

RNA Isolation & Library Preparation

Samples were thawed on ice and all RNA later aspirated leaving only termite gut tissue. This tissue was then homogenized in Promega SV Total RNA Isolation Kit lysis buffer and the manufacturer's protocol followed to extract total RNA from all samples. RNA concentration and relative purity was quantified using a NanoDrop 2000 spectrophotometer (ThermoFisher Scientific).

To reduce eukaryotic bias in library preparation, total RNA was ribodepleted rather than enriched for mRNA. The metatranscriptome libraries were prepared from total RNA using the Ovation Complete Prokaryotic RNA-Seq DR Multiplex System 1-8 (NuGEN) with the addition of custom oligos targeting the 18S rRNA from eukaryotic species anticipated to be in the samples (termite, protists, and fungal pathogen; Table S.1). Total RNA (250 ng) was used as starting material for the Ovation kit and cDNA was synthesized following manufacturer instructions. After second strand synthesis, cDNA samples were frozen overnight at −20° C.

After thawing, samples were sonicated using a Covaris E210 in Covaris #520045 6×16 mm microtubes using the parameters specified in the Ovation protocol (Intensity=5 not 5%) and transferred into fresh 200 uL microtubes and stored overnight at −20° C. cDNA purification, end repair, barcode ligation, first strand selection, and first strand purification were performed per manufacturer's protocol. At the strand selection II step, 1 μL of the 100 μM custom oligo mix was added to 164, of Solution SS5 to deplete eukaryotic rRNAs from samples. Adapter cleavage was performed as specified in the kit manual. Library amplification master mix was made fresh per protocol instructions, but the thermocycler program was modified from the manufacturer's protocol as follows: 95° C. for 2 min, 20 cycles of 95° C. for 30s, 60° C. for 90s, and 65° C. for 5 min. Bead purification of the amplified library was performed with a multi-channel pipet to minimize incubation bias of the libraries. Each sample type (control or fungal pathogen challenged) and biological rep (1-3) were indexed separately for a total of 6 prepped libraries for sequencing.

Metatranscriptome Sequencing, Assembly, Annotation, and Analysis

A workflow summarizing the major steps in the metatranscriptome analysis is shown in FIG. 15 (with numbers 1502 on the left representative of the number of contigs removed during that step and numbers 1504 on the right representative of the number of contigs exiting the step). Purified, indexed libraries were submitted to the PUGC facility for quality control screening and sequenced in 1 lane on the Illumina HiSeq2500 platform to produce 2×100 paired-end reads. Contigs of one control library containing the least rRNA reads were assembled de novo using Trinity 2.1.1 by PUGC; all other libraries were mapped to this assembly to produce a read count table. Any contigs with less than 10 reads across samples or identified by homology search as rRNA were filtered out.

In an effort to annotate the contigs in a taxon-specific way, a custom termite consortium database was built from existing data in the NCBI refseq protein database (bacteria, archaea, select protists, see Table 3) and the *Zootermopsis nevadensis* (OGS), as this was the only lower termite genome available at the time. Reciprocal best hits (RBHs) were determined by using BLAST to identify best hits with our assembly as the query and the custom termite consortium database as the subject (BLASTx) and vice versa (tBLASTn). Contigs that were RBHs with entries in this database at an e-value 1e-5, or less, were carried through for additional analysis, thus ensuring a conservative annotation of contigs in this assembly.

To associate contigs with GO terms, the Genbank identifiers from the list of RBH for each taxon group (bacteria, archaea, protists, and termite) were analyzed using the Uniprot retrieve/ID mapping function. Using the Bioconductor package in R statistical software, edgeR differential expression analyses were done on read counts for all contigs to detect responses to the fungal pathogen (a and FDR=0.05). To determine if any biological processes or molecular functions were enriched in a taxon group, lists of GO terms from each taxon group were compared to all GO terms in the gene set and enrichment was determined with a two-sided Fisher's exact test using the top GO function in the Bioconductor package.

TABLE 3

Database constructed to annotate the metatranscriptome in a taxon specific manner.
Composition of Custom Termite Consortium Database

| Group | Source | No. of Seqs. |
|---|---|---|
| Archaea | NCBI Archaea RefSeq | 851,375 |
| Bacteria | NCBI Bacteria RefSeq | 44,100,533 |
| Protist | NCBI RefSeq for Parabasalia, Oxymonadida, Diplomonadida, and Gregarinasina | 72,948 |
| Termite | OGS for *Zootermopsis nevadensis* | 14,610 |
| | Total Sequences | 45,039,466 |

Metatranscriptome Validation qPCR was used as an independent validation of read count values used to generate contigs for differential expression analysis. Contigs representing termite, bacteria, protist, up-regulated, down-regulated, and no change groups were selected for qPCR validation (see Table S.2 of the Peterson & Scharf Article. Using the cDNA samples generated as described previously, 14, of cDNA, 1 µL each of contig-specific forward/reverse primers, 7 µL nuclease-free water, and 10 µL of SensiFast SYBR no ROX master mix (Bioline) were combined for qPCR using a Bio-Rad CFX-96 system. After an initial denaturation step (10 min. at 95° C.), 45 cycles of denaturing (30 sec. at 95° C.), annealing (30 sec. at 50° C.), and extension (30 sec. at 72° C.) were performed with a real-time scan of fluorescence taken after each cycle. The log ratio CT values were regressed against log ratio of metatranscriptome counts per million values as a measure of congruency. Regression data were analyzed by the Spearman correlation method.

Post-Hoc Assays of Reactive Oxygen Species Abundance, Glutathione S-Transferase Activity, and Amidohydrolase Expression Metatranscriptome findings were further validated using additional biochemical assays to test the potential for oxidative stress and increased antioxidant enzyme activity in the termite gut following *B. bassiana* challenge. Reactive oxygen species (ROS) were detected using a modified FOX1A assay and bioassays were repeated on new termites and guts dissected as described above. A mixture of 100 µL of termite gut homogenate containing 10 termite gut equivalents in 100 mM sodium phosphate buffer was combined with 100 µL, nanopure water and 100 µL, of FOX1A reagent and then incubated for 40 minutes in the dark. Endpoint absorbance was measured at 580 nm and compared to a hydrogen peroxide standard curve to estimate reactive oxygen species concentration. This was repeated in triplicate for control and pathogen-challenged groups and all biological replicates.

GST activity was measured kinetically using CDNB as the substrate. Freshly prepared 1 mM CDNB in 100 mM sodium phosphate buffer (pH 7.0) was combined with 10 µl of gut homogenate with or without 5 mM reduced L-glutathione for a total reaction volume of 235 µl. Absorbance was read kinetically for 10 minutes and mean velocity for all samples were calculated. The mean velocity of glutathione-plus samples was blank-corrected with their corresponding glutathione-minus controls. Specific activity was calculated using the extinction coefficient of CDNB of 9.5 mM$^{-1}$ cm$^{-1}$. Both ROS and GST assays measurements were normalized per milligram of protein in each sample and the protein concentrations thereof were estimated using the Pierce Coomassie Plus Bradford Assay Kit (Thermo-Fisher Scientific).

To investigate whether symbiont removal reduced amidohydrolase expression, groups of 10 workers from three independent colonies were subjected to a treatment of 5% kanamycin (controls received water only) for 48-hours and subsequently challenged with a low dose of *B. bassiana* conidia (as above). 5% Kanamycin was used for bacterial symbiont removal based on extensive preliminary research. These bioassays were held for 48-hours before termite guts were dissected for RNA extraction. cDNA was synthesized using the Bioline SensiFast cDNA Synthesis kit using 1 µg total RNA as template. qPCR was performed using the SensiFast no ROX SYBR Master Mix (Bioline) and amidohydrolase 2 gene specific primers as well as Actin 5C as a reference gene (see Table S.2 of the Peterson & Scharf Article).

Similarly, post-hoc bioassays were performed to determine if 5% kanamycin treatment was sufficient to increase termite susceptibility to *B. bassiana*. As above, groups of 10 termites were treated with 5% kanamycin or water (controls) for 48-hours, and then inoculated with a low dose of *B. bassiana* conidia suspended in 0.5% Tween-20 or a blank of 0.5% Tween-20 solution (controls). All together, these four groups allowed the investigators to account for any baseline mortality caused by antibiotic treatment. These bioassays were held for 7 days before scoring survivorship.

Results

Ribodepletion Effectively Removes rRNA from the Hyper-Diverse Termite Gut

Figure 16A:
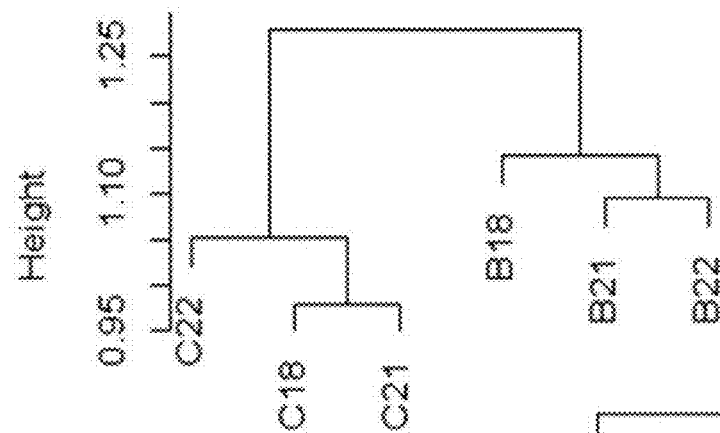
FIGS. 16A-16D show graphical data resulting from quality control analyses of the metatranscriptome sequence, with FIG. 16A showing a cluster dendrogram based on a Pearson distribution of all contigs following normalization (samples labeled with letters indicating their treatment (C=control; B=*Beauveria*) and colony number), FIG. 16B showing a plot of biological coefficient of variation vs. average log CPM (each spot representative of an individual contig), FIG. 16C showing a multiple dimension scaling plot representative of distances in gene expression profiles across biological replicates and treatment groups, FIG. 16D showing the results of a validation experiment showing the correlation between log CT from qPCR analyses (CT of treatment/CT of control) vs. log FC (counts per million of treatment/counts per million of control) and Spearman's correlation coefficient rho ($\rho$) reported shows a significant, strong negative correlation ($\rho$=0.008) and each data point representative of a single gene (n=14)
Figure 16B:
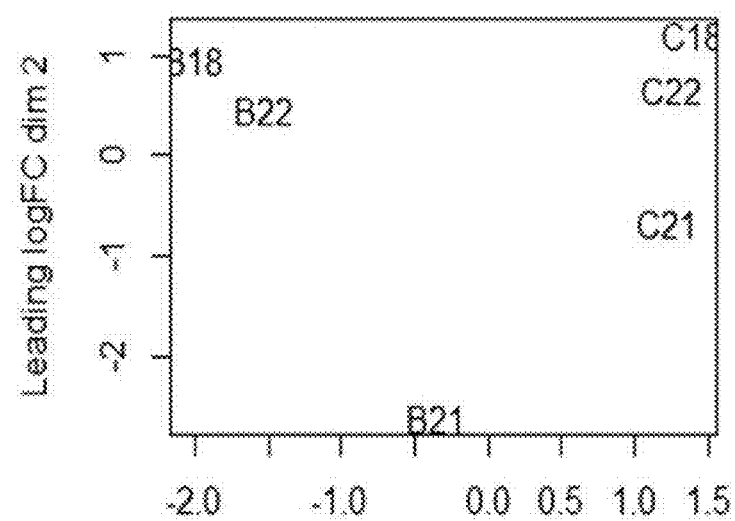
Figure 16C:
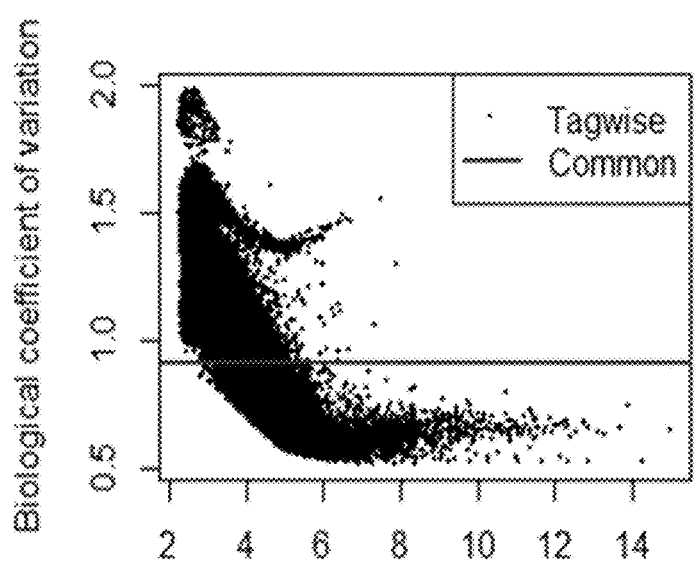

In total, 2,107,824 contigs were assembled de novo from a control termite gut holotranscriptome (see column B of Table 4 below). The analyzed sequences contained 1.2% rRNA reads and the average rRNA contamination across all samples was estimated to be 12.33% (see column A of Table 4 below). It should be noted that pathogen challenged samples had lower read count numbers and higher rRNA than that of the control samples, which is likely due to inefficiency in ribodepletion for fungal rRNAs. Of the assembled contigs, 258,251 had an $N_{50}$ length of 652 bases and average length of 704 bases (column B of Table 2). After filtering out rRNA and contigs with <10 reads across samples, 1,511,386 contigs remained. Additionally, a cluster dendrogram based on a Pearson distribution and a multiple dimension scaling plot both agree in that samples cluster together based on treatment type (control vs. *B. bassiana* challenge) rather than by termite colony (colonies nos. 18, 21, or 22) (see FIGS. 16A and 16C).

TABLE 4

Summary of sequencing and assembly statistics, with A) being a summary of sequencing statistics and * indicating the library used for Trinity assembly which was selected because of low rRNA contamination, and B) being a summary of de novo Trinity assembly. Samples labeled with a letter indicating their treatment (C = control, B = Beauveria) and colony number.

| A Sequencing Statistics | | | B Assembly Statistics | | |
|---|---|---|---|---|---|
| Sample | # Reads | rRNA | All | No. Contigs | 2,107,824 |
| C18 | 97,357,292 | 3.0% | | N50 | 356 |
| C21 | 96,954,778 | 6.3% | | Avg. Length | 361 |
| C22* | 95,291,086 | 1.2% | | | |
| B18 | 75,834,616 | 21.5% | >500 bases | No. Contigs | 258,251 |
| B21 | 83,141,808 | 14.9% | | N50 | 652 |
| B22 | 58,954,982 | 27.3% | | Avg. Length | 704 |

Summary of the Holotranscriptome

Figure 15:
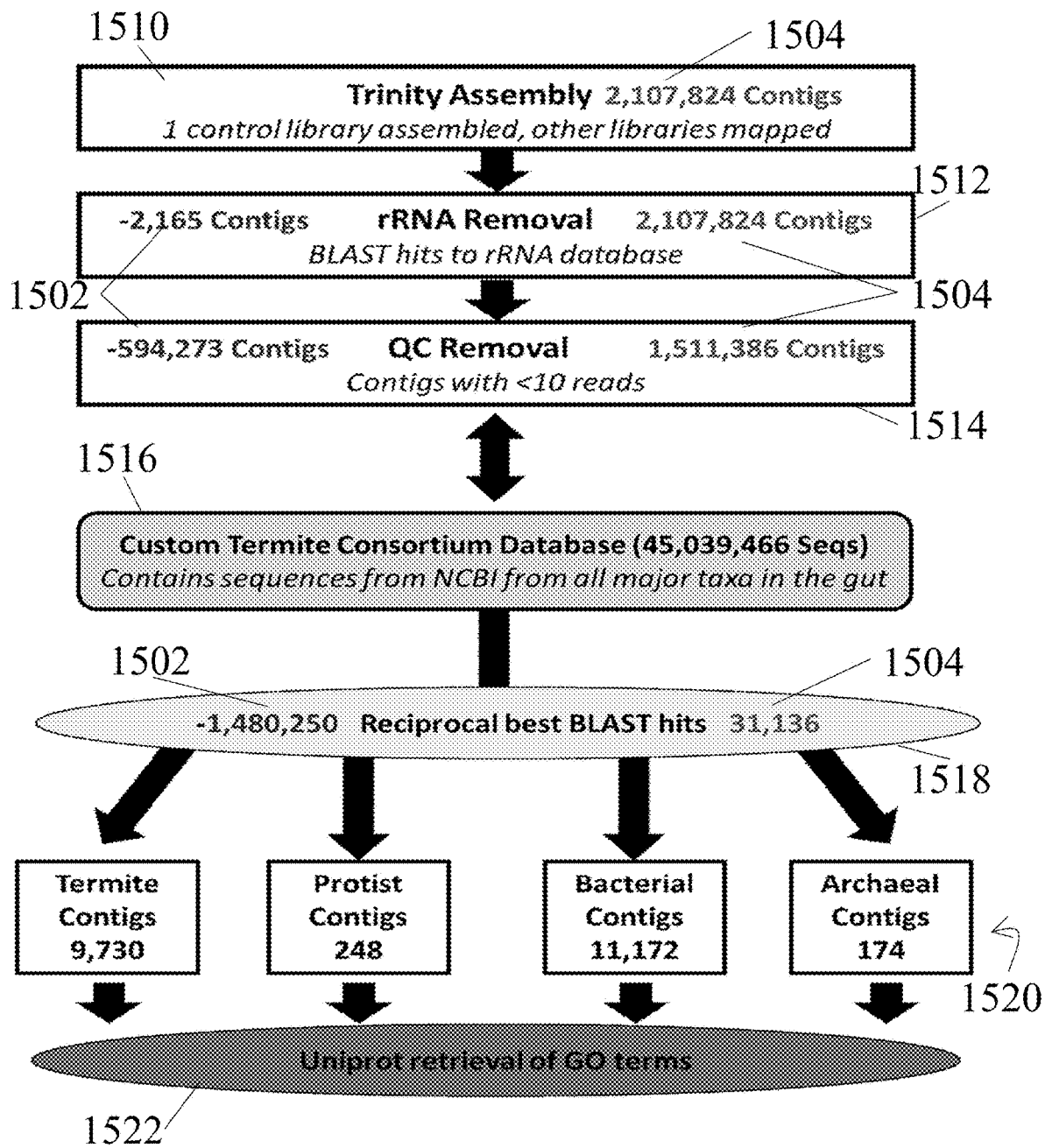
FIG. 15 shows a workflow chart of metatranscriptome annotation, with numbers on the left representative of the number of contigs removed during that step and numbers on the right representative of the n umber of contigs exiting the step.
Figure 17:
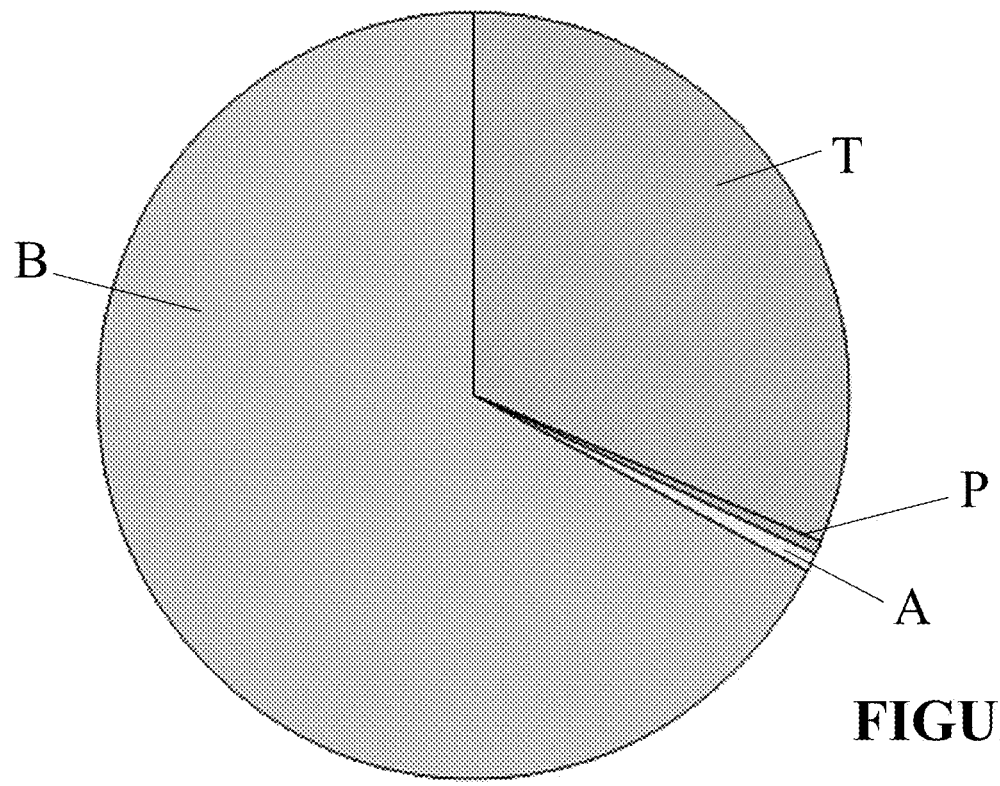
FIG. 17 shows a pie chart demonstrating taxon distributions for the annotated contigs, with total proportions of the contigs from the metatranscriptome annotated as belonging to each taxonomic group (T=termite; P=protist; A=archaea; and B=bacteria) and only those contigs having reciprocal blast hits (RBH) included.

To assign annotations to the genes of interest, all assembled, filtered contigs were reciprocally BLASTed to determine putative function and taxonomic assignment (step 1518 of FIG. 15). A total of 31,136 contigs had RBHs with entries in the custom termite consortium database with an e-value of 1e-5 or less. Each of these annotations was associated with a taxonomic group: termite, protist, bacteria, or archaea (see step 1520 of FIG. 15 and FIG. 17). Of these, 21,269 contigs had hits in the Uniprot ID matching database. It should be noted that the protist (P) and archaeal (A) annotations are more incomplete due to a lack of information available in the NCBI RefSeq database regarding termite symbiont groups (archaea, bacteria, and specific protists).

The bacterial (B) and termite (T) contigs, however, are considerably more complete with annotations in many critical biosynthetic, catabolic, transport, and stress response processes. Table 5 lists identified putative bacterial and termite contig functions based on reciprocal best hits and GO molecular function. Some of these categories, like amino acid biosynthesis for example, appear to have signatures of complementation between the host termite and bacterial symbionts (Table 5).

TABLE 5

Summary of select putative bacterial and termite contig functions (asome candidates possess multi-functional annotations).
Functional Annotations of Contigs

| Category | Bacterial | Termite | Category | Bacterial | Termite |
|---|---|---|---|---|---|
| Biosynthesis | | | Metabolism | | |
| Amino Acid | *143 | 11 | Carbohydrate | 276 | 88 |
| Alanine | 2 | 0 | Glycosyl Hydrolases | 204 | 34 |
| Arginine | 15 | 0 | Glycosyl Transferase | 67 | 39 |
| Asparagine | 3 | 1 | Polysaccharide Lyase | 3 | 7 |
| Cysteine | 3 | 0 | Carbohydrate Esterase | 2 | 8 |
| Glutamine | 2 | 1 | Chitin | 2 | 33 |
| Glycine | 2 | 1 | Nitrogen | 32 | 7 |
| Histidine | 28 | 0 | Amidohydrolase | 14 | 3 |
| Isoleucine | 7 | 0 | Nitrogenase | 6 | 0 |
| Leucine | 6 | 0 | Nitroreductase | 9 | 0 |
| Lysine | 16 | 0 | Urease | 9 | 0 |
| Methionine | 18 | 3 | Other | 8 | 4 |
| Phenylalanine | 2 | 0 | Protein | *207 | *228 |
| Proline | 9 | 1 | Aminopeptidases | 15 | 9 |
| Pyrrolysine | 1 | 0 | Aspartic-type Peptidases | 6 | 9 |
| Serine | 5 | 1 | Carboxypeptidases | 18 | 30 |
| Threonine | 5 | 0 | Cysteine-type Peptidases | 12 | 24 |
| Tryptophan | 6 | 0 | Dipeptidase | 11 | 12 |
| Tyrosine | 3 | 0 | Metallopeptidases | 43 | 61 |
| Valine | 5 | 0 | Serine-type Peptidases | 76 | 81 |
| Other | 22 | 3 | Threonine-type Peptidases | 1 | 12 |
| Vitamin | 29 | 0 | Other Peptidases | 31 | 19 |
| Thiamine | 27 | 0 | Transport | | |
| B6 | 2 | 0 | ABC Transporters | 355 | 2 |
| Fatty Acid | 33 | 12 | Amino Acid | 27 | 0 |
| Lipid | 5 | 2 | Urea | 4 | 0 |
| Cellular Structure | 50 | 8 | Carbohydrate | 42 | 0 |
| Phospholipid | 16 | 8 | Metal Ion | 26 | 0 |
| Peptidoglycan | 34 | 0 | C4-dicarboxylate | 5 | 0 |
| | | | Multidrug | 13 | 0 |
| | | | Excinuclease | 6 | 0 |
| | | | Other | 232 | 2 |
| | | | Other MFS Transporters | 37 | 11 |
| | | | Other Transporters | 163 | 191 |
| | | | Stress Regulation | | |
| | | | Antioxidant/Detoxification Enzymes | 69 | 71 |
| | | | Aldo/Keto Reductase | 7 | 1 |
| | | | Alkyl Hydroperoxide Reductase | 8 | 0 |
| | | | Catalase | 1 | 1 |
| | | | Cytochrome Oxidase P450s | 0 | 31 |
| | | | Desulfoferrodoxin | 4 | 0 |

TABLE 5-continued

Summary of select putative bacterial and termite contig functions (asome candidates possess multi-functional annotations).
Functional Annotations of Contigs

| Category | Bacterial | Termite | Category | Bacterial | Termite |
|---|---|---|---|---|---|
| | | | Ferredoxin | 27 | 0 |
| | | | Glutaredoxin | 0 | 3 |
| | | | Glutathione Peroxidase | 1 | 2 |
| | | | Glutathione S-Transferase | 5 | 6 |
| | | | Peroxidase | 0 | 6 |
| | | | Peroxidasin | 0 | 3 |
| | | | Superoxide Dismutase | 0 | 3 |
| | | | Thioredoxin | 7 | 14 |
| | | | Other | 9 | 1 |
| | | | Chaperonin | 15 | 16 |
| | | | Other | 3 | 4 |

Differential Gene Expression Analysis

Figure 16D:
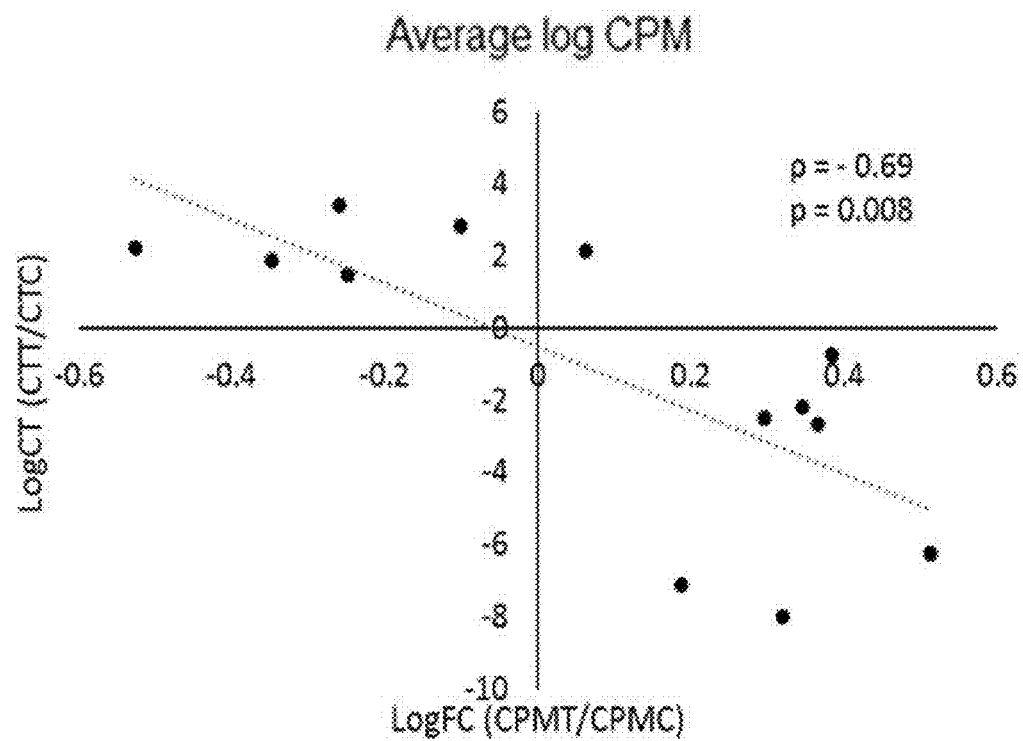

Using edgeR analysis, a total of 563 contigs exhibited significant differential expression in response to fungal pathogen challenge (FDR p<0.05). Most of these contigs were annotated as host-origin, but some symbiont contigs were also impacted (see Table 6). In total, 162 contigs were up-regulated and 401 were down-regulated (Table 6). Of the differentially expressed contigs, only 223 contained Uniprot ID matches and 225 had annotated GO terms. Relative expression observed in the metatranscriptome was validated by qPCR. Log CT ratios were correlated to Log CPM ratios between treatment and control samples (see FIG. 16D). Spearman's correlation coefficient rho (p=−0.69) shows a significant negative correlation (p=0.008), as anticipated.

TABLE 6

Summary of differentially expressed contigs from each taxon based on RBH annotations. Significantly up- and down-regulated contigs from each taxon were determined at α/FDR = 0.05.
Summary Statistics Table for Metatranscriptome RNAseq

| Taxon | Number Up-regulated | No Change | Number Down-regulated |
|---|---|---|---|
| Termite | 134 | 9,339 | 258 |
| Protist | 18 | 228 | 2 |
| Bacteria | 10 | 20,852 | 141 |
| Archaea | 0 | 174 | 0 |
| Total | 162 | 30,593 | 401 |

In general, the termite contigs up-regulated in response to *B. bassiana* challenge reveal the hallmarks of oxidative stress (Table 7). Thirty-one ribosomal proteins were up-regulated, which was associated with slowed or inhibited protein translation. Additionally, a mitochondrial peroxiredoxin (SEQ ID No. 4) and a GST (SEQ ID No. 5) were up-regulated 2.8-fold and 5.1-fold respectively. Stress and immune-associated 10 kDa heat shock protein (SEQ ID No. 7) and ferritin (SEQ ID No. 6) were up-regulated as well. Calcium ($Ca^{2+}$), iron (Fe'), zinc ($Zn^{2+}$), and other generic metal ion binding GO terms were abundant in the pathogen up-regulated termite contigs. Also notably, several components of the OXPHOS pathway were up-regulated (subunits of complex I, complex III, and complex IV and cytochrome c, SEQ ID Nos. 8-15), however; ATP synthase contigs were not differentially expressed. All of these upregulated genes and their protein products are considered viable targets for enhancing termite susceptibility to fungal pathogens for population control purposes.

TABLE 7

Summary of contigs that were significantly up-regulated at 48-h post-inoculation with *B. bassiana*. Annotation and taxon based on RBH to the custom termite consortium database. Fold-change represents $Log_2$ CPM Treatment/CPM Control as calculated by edgeR.
Up-Regulated Contigs in Response to *B. bassiana* Challenge

| Annotation | Fold-Change | Taxon |
|---|---|---|
| Amidohydrolase 2 | 3.43 | Bacteria |
| Peroxiredoxin-mitochondrial | 2.81 | Termite |
| Glutathione S-transferase (GST) | 5.10 | Termite |
| Ferritin | 2.85 | Termite |
| 10 kDa Heat shock protein | 3.40 | Termite |
| Cytochrome b-c1 subunit 10 | 3.91 | Termite |
| Cytochrome b-c1 subunit 7 | 3.04 | Termite |
| Cytochrome b-c1 subunit 9 | 4.30 | Termite |
| Cytochrome c | 2.83 | Termite |
| Cytochrome c oxidase subunit 6B | 2.98 | Termite |
| Cytochrome c oxidase subunit 6C | 3.13 | Termite |
| Cytochrome c oxidase subunit 7C | 2.93 | Termite |
| NADH dehydrogenase 1 alpha subunit | 3.60 | Termite |
| 3'-5' exonuclease | 2.82 | Protist |
| 3'-5' exonuclease/DNA Polymerase I | 3.25 | Protist |
| Ca2+/calmodulin dependent kinase II (CAMKII) | 4.15 | Protist |
| Mitogen-activated protein kinase 1 (MAPK1) | 3.49 | Protist |

Up-regulated protist contigs also have annotations associated with oxidative stress, as well as general stress responses. Of note, two up-regulated protist contigs were annotated as 3'-5' exonucleases/DNA Pol I (SEQ ID Nos. 16 and 17), which is associated with oxidative stress-linked DNA repair. The signal cascade initiators $Ca^{2+}$/CAMKII and MAPK1 (SEQ ID Nos. 18 and 19) were also up-regulated, and have links to oxidative stress response. The only bacterial contig in the up-regulated category with a named annotation is an amidohydrolase family 2 member. These enzymes have a wide-variety of catalytic capabilities, including activity against fungal metabolites.

*Beauveria bassiana* Challenge Results in Oxidative Stress

Figure 18B:
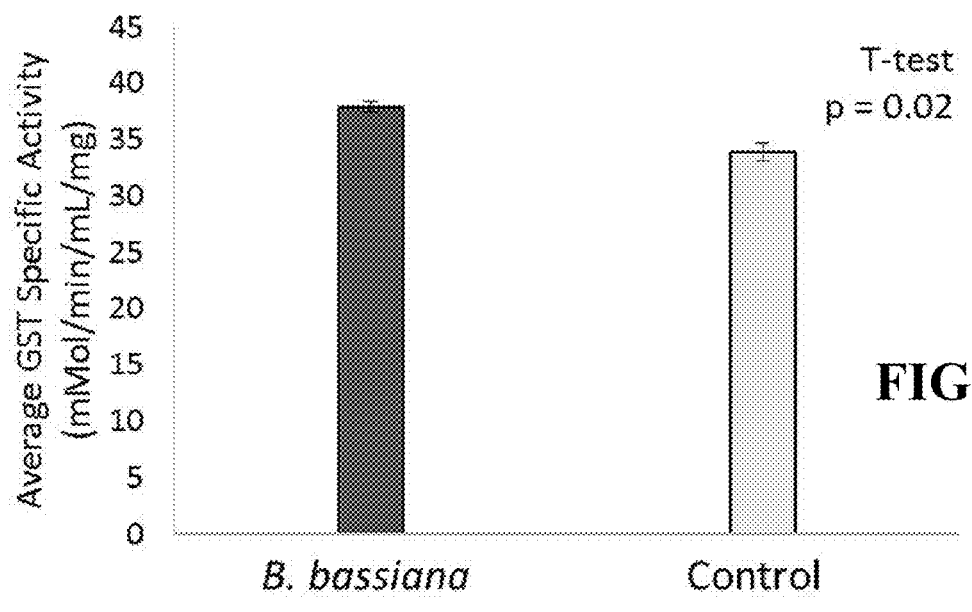

In addition to the up-regulation of genes related to oxidative stress response, following the 48-hour challenge with *B. bassiana*, termite guts exhibited increased ROS present (see FIG. 18A). Additionally, as shown in FIG. 18B, GST activity is significantly higher by 1.15× in pathogen challenged guts than control guts. While the origin of ROS and antioxidant/detoxification activity cannot be identified using this method, it can still be concluded that the termite gut is under oxidative stress 48-hours after inoculation with *B. bassiana*.

Symbiont Reduction Results in Increased *B. bassiana* Susceptibility and Reduced Amidohydrolase Induction by *B. bassiana*

Notably, antibiotic treatment also impacted the expression of the amidohydrolase 2 gene, which was induced by *B. bassiana* challenge in the metatranscriptome dataset. As shown in FIG. 19A, following treatment with kanamycin, an antimicrobial drug, amidohydrolase 2 gene expression was reduced~5× in pathogen challenged termites compared to water treated controls. Finally, in agreement with the amidohydrolase result above, treatment with kanamycin resulted in a 3× increase in termite susceptibility to *B. bassiana* (see FIG. 19B) underscoring the apparent relevance of the amidohydrolase gene as a mechanism of bacterial-mediated fungal defense.

Methods for Controlling Termite Populations

The methods for controlling termite populations of the present disclosure leverage the findings presented herein. FIG. 21 shows a flow-chart representative of at least one embodiment of a method 2100 for controlling termite populations by attenuating a termite host response to increase pathogen virulence with respect thereto. In at least one such embodiment, the method 2100 comprises the steps of administering a composition to a termite to promote symbiont dysbiosis in the gut of the termite (step 2102) and exposing the termite to one or more pathogens (step 2104). The pathogen may comprise any natural or introduced pathogen that is capable of attacking the termite (for example, an entomopathogenic fungi or bacteria).

As described in detail above, because symbiont activity plays a significant role in a termite's innate defense mechanisms, gut dysbiosis can have a significant deleterious effect on the termite's antibacterial and/or antifungal defense mechanisms. Accordingly, by facilitating symbiont dysbiosis in the termite's gut (step 2102), performance of the method 2100 renders the termite more susceptible to pathogenic attack, which may then be used (step 2104) to control termite population either in addition to, or in lieu of, administering a neonicotinoid or other insecticide.

Method 2100 may additionally comprise the step of compromising the immunity-related social behaviors of the termite (optional step 2106). For example, in at least one embodiment, step 2106 may comprise administering a neonicotinoid or another insecticide. Even if the neonicotinoid or other pesticide comprises a concentration equivalent to a nonlethal dosage, performance of the method 2100 is effective to control termite populations because the administered composition successfully compromises the termite's defense mechanisms through symbiont dysbiosis at step 2102.

Now referring to FIG. 22, as the experimental data and results of the present disclosure support, there are numerous ways to perform step 2102. In at least one embodiment, step 2102 comprises targeting specific bacterial groups within the termite gut that upregulate one or more of the identified genes and/or contigs that encode symbiont-mediated immunity (step 2202). For example, symbiont dysbiosis may be facilitated by reducing or eliminating the bacterial group(s) that encode mechanisms of symbiont-mediated immunity, thereby preventing or decreasing the bacterial contributions to the termite's defense mechanisms. In such cases, the composition administered at step 2102 may comprise drugs or pesticides selected to reduce or eliminate the bacterial group(s) of interest (see FIG. 22 for a graphical representation of step 2102).

Additionally or alternatively, step 2102 may comprise downregulating at least one symbiont gene, protein, or contig present within the termite (step 2204), which may be achieved using techniques such as RNA interference or the like and/or through the administration of pharmacological agents such as kanamycin (which may be included with or separate from the composition administered to the termite). Numerous genes (both host and symbiont) and the proteins or contigs they encode are identified herein as being associated with nicotinoid-pathogen synergy and/or exhibiting a significant fold-change in response to pathogen challenge (i.e. are part of the innate defense mechanism present within insects and termites). By suppressing and/or downregulating the expression of one or more of these identified genes, proteins, and/or contigs at step 2204, symbiont dysbiosis is achieved and the termite's innate defense mechanism is dismantled, thereby enhancing the termite's susceptibility to the pathogen at step 2104. Exemplary examples of such antimicrobial host genes include (without limitation): allatostatin, neuropeptide F, lysozyme, pathogen-recognition proteins, termicin, leucine-rich repeat proteins, and/or transferrins. Likewise, examples of such proteins that are associated with anti-fungal defense may include (without limitation: amidohydrolase 2, peroxiredoxin, glutathione s-transferase, ferritin, heat shock protein, cytochrome b-c1 subunits 79, and 10, cytochrome c, cytochrome c oxidase subunits 6B, 6C, and 7C, NADH dehydrogenase 1 alpha subunit, 3'-5' exonuclease, 3'-5' exonuclease-DNA polymerase I, calcium-calmodulin dependent kinase II CAMKII, and mitogen-activated protein kinase 1 MAPKI.

It will be appreciated that the gene, contig, or protein downregulated at step 2204 may be selected to coordinate with the pathogen used in step 2104—for example, if a bacterial pathogen is utilized, step 2204 may comprise downregulating an antimicrobial host gene/protein/contig, whereas if a fungi pathogen is utilized, step 2204 may comprise downregulating an anti-fungal symbiont gene/protein/contig. Additionally, any combination of the foregoing may be employed.

The composition to be administered in step 2102 may be specifically formulated to perform the steps of the method 2100 described herein. For example, the composition may be formulated to alter antimicrobial transcripts present within the termite's gut and/or to eliminate or reduce one or more symbionts (protists or bacteria) present within the gut of the termite that induce the upregulation of an antimicrobial host gene. Additionally or alternatively, the composition may comprise a pesticide, insecticide, and/or pharmacological agents in functional amounts to achieve the results described herein.

Because the methods and compositions hereof increase the termite population's susceptibility to pathogen attack, the novel methods and compositions provided herein are effective at controlling and/or eliminating termite populations without the (or with the reduced and/or lower dosage) use of synthetic compositions (insecticides, for example).

While various embodiments of compositions and methods for the control of termites and/or fungal infections have been described in considerable detail herein, such embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments of the present disclosure, the specification may have presented the method and/or process of the present disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present disclosure should not be limited to the performance of their steps in the order written, and one skilled in the art can readily appreciate that the sequences may be varied and still remain within the spirit and scope of the present disclosure.

The invention claimed is:

1. A method for controlling termite populations, the method comprising the steps of:
   administering a composition to a termite, the composition formulated to promote symbiont dysbiosis in a gut of the termite and comprising an RNA interference construct comprising at least one double stranded RNA region, at least one strand of which comprises a nucleotide sequence that is complementary to a portion of a nucleotide sequence of any one of SEQ ID NOs. 3-19; and
   exposing the termite to a pathogen;
   wherein administering the composition increases the susceptibility of the termite to the pathogen.

2. The method of claim 1, wherein the pathogen comprises an entomopathogenic fungi.

3. The method of claim 1, wherein at least one strand of the RNA interference construct comprises a nucleotide sequence that is complementary to a portion of a symbiont nucleotide sequence of any one of SEQ ID NOs. 3 and 16-19.

4. The method of claim 1, wherein the composition further comprises a sublethal dose of neonicotinoid.

5. The method of claim 4, wherein the neonicotinoid comprises at or near 0.0001% imidacloprid in solution.

6. The method of claim 1, further comprising the step of downregulating at least one symbiont gene present within the termite, and wherein the step of exposing the termite to a pathogen upregulates at least one antimicrobial host gene of the termite and the expression of a protein encoded by such at least one antimicrobial host gene.

7. The method of claim 6, wherein at least one downregulated symbiont gene comprises a gene that encodes a protist glycosyl hydrolase family 7 cellulase, wherein beta 1, 3-glycosidase activity is reduced by such downregulation.

8. The method of claim 6, wherein the protein is selected from the group consisting of: allatostatin, neuropeptide F, lysozyme, pathogen-recognition proteins, termicin, leucine-rich repeat proteins, and/or transferrins; and
   the method further comprises the step of decreasing expression of one or more transcripts that encode the protein using an RNA interference technique.

9. A method for controlling termite populations comprising the steps of:

manipulating expression of one or more targeted genes to promote symbiont dysbiosis in a gut of a termite by administering a composition to the termite, the composition comprising:
- an RNA interference construct comprising at least one double stranded RNA region, at least one strand of which comprises a nucleotide sequence that is complementary to a portion of a nucleotide sequence of any one of SEQ ID NOs. 3-19; and exposing the termite to at least one pathogen;
wherein manipulating the expression of the one or more targeted genes increases the susceptibility of the termite to the pathogen and the nucleotide sequence of any one of SEQ ID NOs. 3-19 corresponds with one of the one or more targeted genes.

10. The method of claim 9, wherein the symbiont comprises a protist symbiont population or a bacteria symbiont population present within the gut of the termite and the targeted gene comprises a gene of the symbiont.

11. The method of claim 9, wherein the step of manipulating the expression a targeted gene is further to compromise one or more defense mechanisms of the termite, wherein at least one of the one or more defense mechanisms of the termite comprises a social behavior.

12. The method of claim 10, wherein the step of manipulating the expression of one or more targeted genes comprises downregulating at least one symbiont gene of a protist present within the protist symbiont population and wherein the composition further comprises a sublethal dose of a neonicotinoid, and the at least one strand of the RNA interference construct comprises a nucleotide sequence that is complementary to a portion of a nucleotide sequence of any one of SEQ ID NOs. 3 or 16-19.

13. The method of claim 12, wherein the at least one symbiont gene comprises a gene that encodes a protist glycosyl hydrolase family 7 cellulase and the at least one pathogen comprises an entomopathogenic fungi.

14. The method of claim 9, wherein:
the symbiont comprises a bacteria symbiont population present within the gut of the termite;
the at least one pathogen comprises a bacteria and an entomopathogenic fungi;
the one or more targeted genes comprises at least a gene that encodes a protein selected from a group consisting of: amidohydrolase 2, peroxiredoxin-mitochondrial, glutathione s-transferase, ferritin, 10 kDa heat shock protein, cytochrome b-c1 subunits 7, 9, and 10, cytochrome c, cytochrome c oxidase subunits 6B, 6C, and 7C, NADH dehydrogenase 1 alpha subunit, 3'-5' exonuclease, 3'-5' exonuclease/DNA polymerase I, calcium-calmodulin dependent kinase II, and mitogen-activated protein kinase 1; and
the step of manipulating the expression of a targeted gene further comprises downregulating the targeted gene.

15. The method of claim 14, wherein the composition further comprises kanamycin.

16. The method of claim 9, wherein the composition further comprises at least a sublethal dose of a neonicotinoid, the sublethal dose being at or near 0.0001% imidacloprid in solution, wherein the sublethal dose is sufficient to reduce hindgut protist symbiont populations in the termite without directly killing the termite or modifying the hindgut structure.

* * * * *